US009499865B2

(12) United States Patent
Faham et al.

(10) Patent No.: US 9,499,865 B2
(45) Date of Patent: Nov. 22, 2016

(54) DETECTION AND MEASUREMENT OF TISSUE-INFILTRATING LYMPHOCYTES

(71) Applicant: Adaptive Biotechnologies Corp., Seattle, WA (US)

(72) Inventors: Malek Faham, Pacifica, CA (US); Mark Klinger, San Francisco, CA (US)

(73) Assignee: ADAPTIVE BIOTECHNOLOGIES CORP., Seattle, WA (US)

( * ) Notice: Subject to any disclaimer, the term of this patent is extended or adjusted under 35 U.S.C. 154(b) by 0 days.

(21) Appl. No.: 13/688,414

(22) Filed: Nov. 29, 2012

(65) Prior Publication Data

US 2013/0150252 A1  Jun. 13, 2013

Related U.S. Application Data

(60) Provisional application No. 61/570,192, filed on Dec. 13, 2011.

(51) Int. Cl.
*C12Q 1/68* (2006.01)
*C12Q 1/06* (2006.01)
*C12P 19/34* (2006.01)
*G01N 33/50* (2006.01)

(52) U.S. Cl.
CPC .............. *C12Q 1/6881* (2013.01); *C12Q 1/06* (2013.01); *G01N 33/5091* (2013.01); *G01N 33/5094* (2013.01)

(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 4,474,754 A | 10/1984 | Shimizu et al. |
| 4,683,195 A | 7/1987 | Mullis et al. |
| 4,683,202 A | 7/1987 | Mullis |
| 4,751,188 A | 6/1988 | Valet |
| 4,800,159 A | 1/1989 | Mullis et al. |
| 4,876,189 A | 10/1989 | Schetters |
| 4,942,124 A | 7/1990 | Church |
| 4,965,188 A | 10/1990 | Mullis et al. |
| 5,075,217 A | 12/1991 | Weber |
| 5,126,022 A | 6/1992 | Soane et al. |
| 5,149,625 A | 9/1992 | Church et al. |
| 5,168,038 A | 12/1992 | Tecott et al. |
| 5,189,147 A | 2/1993 | Saito et al. |
| 5,210,015 A | 5/1993 | Gelfand et al. |
| 5,213,960 A | 5/1993 | Chang |
| 5,231,012 A | 7/1993 | Mosmann et al. |
| 5,296,351 A | 3/1994 | Morley et al. |
| 5,298,396 A | 3/1994 | Kotzin et al. |
| 5,326,696 A | 7/1994 | Chang |
| 5,336,598 A | 8/1994 | Kotzin et al. |
| 5,364,759 A | 11/1994 | Caskey et al. |
| 5,399,491 A | 3/1995 | Kacian et al. |
| 5,418,134 A | 5/1995 | Morley |
| 5,449,752 A | 9/1995 | Fujii et al. |
| 5,498,392 A | 3/1996 | Wilding et al. |
| 5,506,126 A | 4/1996 | Seed et al. |
| 5,587,128 A | 12/1996 | Wilding et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,698,396 A | 12/1997 | Pfreundschuh |
| 5,699,798 A | 12/1997 | Hochman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,854,033 A | 12/1998 | Lizardi |
| 5,858,195 A | 1/1999 | Ramsey |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

Sing et al., Hepatology, 33 (5):2001, 1288-98.*
Sfanos et al., Clin Cancer Res 2008;14:3254-3261.*
Liu et al, Journ of Exp Med, vol. 203, No. 7, 2008, pp. 1701-1711.*
Bene, et al. How and why minimal residual disease studies are necessary in leukemia: a review from WP10 and WP12 of the European LeukaemiaNet. Haematologica. Aug. 2009;94(8):1135-50. Epub Jul. 7, 2009.
Benichou, et al. Rep-Seq: uncovering the immunological repertoire through next-generation sequencing. Immunology. Mar. 2012;135(3):183-91. doi: 10.1111/j.1365-2567.2011.03527.x.
Biggerstaff, et al. Enumeration of leukocyte infiltration in solid tumors by confocal laser scanning microscopy. BMC Immunol. Jul. 21, 2006;7:16.
Boyce, et al. Human regulatory T-cell isolation and measurement of function. BD Biosciences. Mar. 2010; 1-20.
Boyd, et al. Individual variation in the germline Ig gene repertoire inferred from variable region gene rearrangements. J Immunol. Jun. 15, 2010;184(12):6986-92. Epub May 21, 2010.

(Continued)

*Primary Examiner* — David Thomas
(74) *Attorney, Agent, or Firm* — Cooley LLP

(57) ABSTRACT

The present invention is drawn to methods for measuring numbers, levels, and/or ratios of cells, such as lymphocytes, infiltrated into a solid tissue, such as a tumor or a tissue affected by an autoimmune disease, and to methods for making patient prognoses based on such measurements. In one aspect, methods of the invention comprise sorting lymphocytes from an accessible tissue, such as peripheral blood, into functional subsets, such as cytotoxic T cells and regulatory T cells, and generating clonotype profiles of each subset. An inaccessible disease-affected tissue is sampled and one or more clonotype profiles are generated. From the latter clonotype profiles, levels lymphocytes in each of the functional subsets are determined in the disease-affected tissue by their clonotypes, which are identified from lymphocytes sorted into subsets from the accessible tissue.

29 Claims, 7 Drawing Sheets

(56) References Cited

U.S. PATENT DOCUMENTS

| | | |
|---|---|---|
| 5,925,517 A | 7/1999 | Tyagi et al. |
| 5,935,793 A | 8/1999 | Wong |
| 5,969,108 A | 10/1999 | McCafferty et al. |
| 5,981,176 A | 11/1999 | Wallace |
| 5,981,179 A | 11/1999 | Lorinez et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,087,096 A | 7/2000 | Dau |
| 6,090,592 A | 7/2000 | Adams et al. |
| 6,143,496 A | 11/2000 | Brown et al. |
| 6,172,214 B1 | 1/2001 | Brenner |
| 6,174,670 B1 | 1/2001 | Wittwer et al. |
| 6,258,540 B1 | 7/2001 | Lo et al. |
| 6,258,568 B1 | 7/2001 | Nyren |
| 6,300,070 B1 | 10/2001 | Boles et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seeger |
| 6,569,627 B2 | 5/2003 | Wittwer et al. |
| 6,596,492 B2 | 7/2003 | Avery et al. |
| 6,605,272 B2 | 8/2003 | Novak et al. |
| 6,613,525 B2 | 9/2003 | Nelson et al. |
| 6,667,159 B1 | 12/2003 | Walt |
| 6,753,147 B2 | 6/2004 | Vogelstein et al. |
| 6,787,308 B2 | 9/2004 | Balasubramanian et al. |
| 6,794,499 B2 | 9/2004 | Wengel et al. |
| 6,806,079 B1 | 10/2004 | McCafferty et al. |
| 6,858,412 B2 | 2/2005 | Willis et al. |
| 6,919,434 B1 | 7/2005 | Goto et al. |
| 6,964,850 B2 | 11/2005 | Bevilacqua et al. |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham et al. |
| 8,628,927 B2 | 1/2014 | Faham et al. |
| 8,685,678 B2 | 4/2014 | Casbon |
| 8,691,510 B2 | 4/2014 | Faham et al. |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham et al. |
| 8,759,036 B2 | 6/2014 | Wang |
| 8,795,970 B2 | 8/2014 | Faham et al. |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0033490 A1 | 2/2004 | Laird et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |

(56) References Cited

U.S. PATENT DOCUMENTS

| | | |
|---|---|---|
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Woudenberg |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0330571 A1 | 12/2010 | Robins et al. |
| 2011/0003291 A1 | 1/2011 | Pasqual |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham et al. |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2013/0005584 A1 | 1/2013 | Faham et al. |
| 2013/0017957 A1 | 1/2013 | Faham et al. |
| 2013/0065768 A1 | 3/2013 | Zheng et al. |
| 2013/0116130 A1 | 5/2013 | Fu |
| 2013/0123120 A1 | 5/2013 | Zimmermann et al. |
| 2013/0136799 A1 | 5/2013 | Faham at al. |
| 2013/0150252 A1 | 6/2013 | Faham et al. |
| 2013/0196328 A1 | 8/2013 | Pepin et al. |
| 2013/0196861 A1 | 8/2013 | Quake |
| 2013/0202718 A1 | 8/2013 | Pepin et al. |
| 2013/0236895 A1 | 9/2013 | Faham et al. |
| 2013/0253842 A1 | 9/2013 | Sherwood et al. |
| 2013/0267427 A1 | 10/2013 | Faham et al. |
| 2013/0288237 A1 | 10/2013 | Robins et al. |
| 2013/0302801 A1 | 11/2013 | Asbury et al. |
| 2013/0324422 A1 | 12/2013 | Faham et al. |
| 2013/0344066 A1 | 12/2013 | Faham et al. |
| 2014/0057799 A1 | 2/2014 | Johnson et al. |
| 2014/0094376 A1 | 4/2014 | Han |
| 2014/0127699 A1 | 5/2014 | Han |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0234835 A1 | 8/2014 | Pepin et al. |
| 2014/0235454 A1 | 8/2014 | Faham et al. |
| 2014/0255929 A1 | 9/2014 | Zheng |
| 2014/0255944 A1 | 9/2014 | Carlton et al. |
| 2014/0256567 A1 | 9/2014 | Robins et al. |
| 2014/0256592 A1 | 9/2014 | Faham et al. |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham |
| 2014/0356339 A1 | 12/2014 | Faham et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham |
| 2015/0051089 A1 | 2/2015 | Robins et al. |
| 2015/0065352 A1 | 3/2015 | Faham et al. |
| 2015/0167080 A1 | 6/2015 | Moorhead et al. |
| 2015/0203897 A1 | 7/2015 | Robins et al. |
| 2015/0218656 A1 | 8/2015 | Kirsch et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0299785 A1 | 10/2015 | Livingston et al. |

FOREIGN PATENT DOCUMENTS

| | | |
|---|---|---|
| EP | 0303459 A2 | 2/1989 |
| EP | 0799897 A1 | 10/1997 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088432 A1 | 8/2009 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008099588 A | 5/2008 |
| WO | WO 93/01838 A1 | 2/1993 |
| WO | WO 2005/059176 A1 | 6/1995 |
| WO | WO 95/28481 A1 | 10/1995 |
| WO | WO 97/13877 A1 | 4/1997 |
| WO | WO 97/18330 A1 | 5/1997 |
| WO | WO 97/46706 A1 | 12/1997 |
| WO | WO 98/01738 A1 | 1/1998 |
| WO | WO 98/44151 A1 | 10/1998 |
| WO | WO 99/19717 A1 | 4/1999 |
| WO | WO 99/20798 A1 | 4/1999 |
| WO | WO 02/24322 A2 | 3/2002 |
| WO | WO 03/008624 A2 | 1/2003 |
| WO | WO 03/044225 A2 | 5/2003 |

(56) References Cited

FOREIGN PATENT DOCUMENTS

| | | |
|---|---|---|
| WO | WO 03/052101 A1 | 6/2003 |
| WO | WO 03/059155 A2 | 7/2003 |
| WO | WO 03/044225 A3 | 12/2003 |
| WO | WO 2004/003820 A2 | 1/2004 |
| WO | WO 03/059155 A3 | 3/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/033728 A3 | 8/2004 |
| WO | WO 2004/046098 A3 | 8/2004 |
| WO | WO 2004/096985 A2 | 11/2004 |
| WO | WO 2005/005651 A2 | 1/2005 |
| WO | WO 2004/063706 A3 | 5/2005 |
| WO | WO 2005/042774 A2 | 5/2005 |
| WO | WO 2005/042774 A3 | 6/2005 |
| WO | WO 2005/053603 A2 | 6/2005 |
| WO | WO 2005/056828 A1 | 6/2005 |
| WO | WO 2004/003820 A3 | 7/2005 |
| WO | WO 2005/084134 A2 | 9/2005 |
| WO | WO 2005/005651 A3 | 11/2005 |
| WO | WO 2005/111242 A2 | 11/2005 |
| WO | WO 2005/113803 A1 | 12/2005 |
| WO | WO 2004/096985 A3 | 3/2006 |
| WO | WO 2004/034031 A3 | 7/2006 |
| WO | WO 2006/076205 A2 | 7/2006 |
| WO | WO 2005/053603 A3 | 9/2006 |
| WO | WO 2006/110855 A2 | 10/2006 |
| WO | WO 2006/116155 A2 | 11/2006 |
| WO | WO 2006/138284 A2 | 12/2006 |
| WO | WO 2006/116155 A3 | 11/2007 |
| WO | WO 2007/134220 A2 | 11/2007 |
| WO | WO 2008/026927 A2 | 3/2008 |
| WO | WO 2008/026927 A3 | 4/2008 |
| WO | WO 2008/039694 A2 | 4/2008 |
| WO | WO 2008/039694 A3 | 4/2008 |
| WO | WO 2008/108803 A2 | 9/2008 |
| WO | WO 2008/108803 A3 | 12/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2005/084134 A3 | 4/2009 |
| WO | WO 2006/076205 A3 | 4/2009 |
| WO | WO 2009/045898 A2 | 4/2009 |
| WO | WO 2009/070767 A2 | 6/2009 |
| WO | WO 2009/019657 A3 | 8/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/070767 A3 | 10/2009 |
| WO | WO 2009/108866 A3 | 10/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/158521 A2 | 12/2009 |
| WO | WO 2009/108860 A3 | 1/2010 |
| WO | WO 2009/137255 A3 | 1/2010 |
| WO | WO 2010/011894 A1 | 1/2010 |
| WO | WO 2009/151628 A3 | 2/2010 |
| WO | WO 2009/137832 A3 | 4/2010 |
| WO | WO 2010/036352 A1 | 4/2010 |
| WO | WO 2009/158521 A3 | 5/2010 |
| WO | WO 2010/053587 A2 | 5/2010 |
| WO | WO 2010/151416 A1 | 12/2010 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2011/106738 A3 | 12/2011 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/048340 A3 | 6/2012 |
| WO | WO 2012/083069 A2 | 6/2012 |
| WO | WO 2012/083225 A2 | 6/2012 |
| WO | WO 2012/142213 A2 | 10/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2015/002908 A1 | 1/2015 |
| WO | WO 2015/013461 A2 | 1/2015 |
| WO | WO 2015/058159 A1 | 4/2015 |

OTHER PUBLICATIONS

Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.

Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.

Campana. Minimal residual disease in acute lymphoblastic leukemia. Semin Hematol. Jan. 2009;46(1):100-6.

Choi, et al. Relapse in children with acute lymphoblastic leukemia involving selection of a preexisting drug-resistant subclone. Blood. Jul. 15, 2007;110(2):632-9. Epub Mar. 19, 2007.

Deschoolmeester, et al. Tumor infiltrating lymphocytes: an intriguing player in the survival of colorectal cancer patients. BMC Immunol Apr. 12, 2010;11:19. doi: 10.1186/1471-2172-11-19.

Dunn, et al. Focus on TILs: Prognostic significance of tumor infiltrating lymphocytes in human glioma. Cancer Immun. Aug. 2007 13;7:12.

Han, et al. Immunorepertoire analysis by multiplex PCR amplification and high throughput sequencing . The Journal of Immunology, 2009; 182, 42.6. Abstract only.

Heger, M. Studies Highlight Challenges of Immune Repertoire Sequencing's Clinical Applicability. Available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.

International search report and written opinion dated Feb. 26, 2013 for PCT Application No. US2012/069310.

Jalla, et al. Enumeration of lymphocyte subsets using flow cytometry: Effect of storage before and after staining in a developing country setting. Indian J Clin Biochem. Jul. 2004;19(2):95-9. doi: 10.1007/BF02894264.

(56) References Cited

OTHER PUBLICATIONS

Jochems, et al. Tumor-infiltrating immune cells and prognosis: the potential link between conventional cancer therapy and immunity. Exp Biol Med (Maywood). May 1, 2011;236(5):567-79. doi: 10.1258/ebm.2011.011007. Epub Apr. 12, 2011.
Kato, et al. Analysis of accumulated T cell clonotypes in patients with systemic lupus erythematosus. Arthritis Rheum. Dec. 2000;43(12):2712-21.
Koch, et al. Tumor infiltrating T lymphocytes in colorectal cancer: Tumor-selective activation and cytotoxic activity in situ. Ann Surg. Dec. 2006;244(6):986-92; discussion 992-3.
Langerak, et al. Polymerase chain reaction-based clonality testing in tissue samples with reactive lymphoproliferations: usefulness and pitfalls. A report of the BIOMED-2 Concerted Action BMH4-CT98-3936. Leukemia. Feb. 2007;21(2):222-9. Epub Dec. 14, 2006.
Lee, et al. Prognostic implications of type and density of tumour-infiltrating lymphocytes in gastric cancer. Br J Cancer. Nov. 18, 2008;99(10):1704-11. doi: 10.1038/sj.bjc.6604738. Epub Oct. 21, 2008.
Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.
Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.
Meleshko, et al. Rearrangements of IgH, TCRD and TCRG genes as clonality marker of childhood acute lymphoblastic leukemia. Exp Oncol. Dec. 2005;27(4):319-24.
Naito, et al. CD8+ T cells infiltrated within cancer cell nests as a prognostic factor in human colorectal cancer. Cancer Res. Aug. 15, 1998;58(16):3491-4.
Neale, et al. Comparative analysis of flow cytometry and polymerase chain reaction for the detection of minimal residual disease in childhood acute lymphoblastic leukemia. Leukemia. May 2004;18(5):934-8.
Nelson. CD20+ B cells: the other tumor-infiltrating lymphocytes. J Immunol. Nov. 1, 2010;185(9):4977-82. doi: 10.4049/jimmunol.1001323.
Nosho, et al. Tumour-infiltrating T-cell subsets, molecular changes in colorectal cancer, and prognosis: cohort study and literature review. J Pathol. Dec. 2010;222(4):350-66. doi: 10.1002/path.2774.
Oble, et al. Focus on TILs: prognostic significance of tumor infiltrating lymphocytes in human melanoma. Cancer Immun. Apr. 2, 2009;9:3.
Ohtani. Focus on TILs: prognostic significance of tumor infiltrating lymphocytes in human colorectal cancer. Cancer Immun. Feb. 21, 2007;7:4.
Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.
Reddy, et al. Systems analysis of adaptive immunity by utilization of high-throughput technologies. Curr Opin Biotechnol. Aug. 2011;22(4):584-9. Epub May 12, 2011.
Robins, et al. Ultra-sensitive detection of rare T cell clones. Immunol Methods. Jan. 31, 2012;375(1-2):14-9. Epub Sep. 10, 2011.
Sato, et al. Intraepithelial CD8+ tumor-infiltrating lymphocytes and a high CD8+/regulatory T cell ratio are associated with favorable prognosis in ovarian cancer. Proc Natl Acad Sci U S A. Dec. 20, 2005;102(51):18538-43. Epub Dec. 12, 2005.
Schreiber, et al. Cancer immunoediting: integrating immunity's roles in cancer suppression and promotion. Science. Mar. 25, 2011;331(6024):1565-70. doi: 10.1126/science.1203486.
Sehouli, et al. Epigenetic quantification of tumor-infiltrating T-lymphocytes. Epigenetics. Feb. 2011;6(2):236-46. Epub Feb. 1, 2011.

Sramkova, et al. Detectable minimal residual disease before allogeneic hematopoietic stem cell transplantation predicts extremely poor prognosis in children with acute lymphoblastic leukemia. Pediatr Blood Cancer. Jan. 2007;48(1):93-100.
Straten, et al. T-cell clonotypes in cancer. J Transl Med. Apr. 8, 2004;2(1):11.
Uppaluri, et al. Focus on TILs: prognostic significance of tumor infiltrating lymphocytes in head and neck cancers. Cancer Immun. Dec. 4, 2008;8:16.
Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.
Wang, et al. High throughput sequencing reveals a complex pattern of dynamic interrelationships among human T cell subsets. Proc Natl Acad Sci U S A. Jan. 26, 2010; 107(4): 1518-1523.
Warren, et al. Exhaustive T-cell repertoire sequencing of human peripheral blood samples reveals signatures of antigen selection and a directly measured repertoire size of at least 1 million clonotypes. Genome Res. Feb. 24, 2011. [Epub ahead of print].
Westermann, et al. Distribution of lymphocyte subsets and natural killer cells in the human body. Clin Investig. Jul. 1992;70(7):539-44.
Zaliova, et al. Quantification of fusion transcript reveals a subgroup with distinct biological properties and predicts relapse in BCR/ABL-positive ALL: implications for residual disease monitoring. Leukemia. May 2009;23(5):944-51. Epub Jan. 22, 2009.
Zhou, et al. Isolation of purified and live Foxp3+ regulatory T cells using FACS sorting on scatter plot. J Mol Cell Biol. Jun. 2010;2(3):164-9. doi:10.1093/jmcb/mjq007. Epub Apr. 29, 2010.
U.S. Appl. No. 61/045,586, filed Apr. 16, 2008, Han et al.
U.S. Appl. No. 12/945,678, filed Nov. 12, 2010, Faham et al.
U.S. Appl. No. 13/174,086, filed Jun. 30, 2011, Faham et al.
U.S. Appl. No. 13/196,885, filed Aug. 2, 2011, Moorhead et al.
U.S. Appl. No. 13/369,031, filed Feb. 8, 2012, Faham et al.
U.S. Appl. No. 13/627,497, filed Sep. 26, 2012, Faham et al.
U.S. Appl. No. 13/763,978, filed Feb. 11, 2013, Faham et al.
U.S. Appl. No. 13/861,941, filed Apr. 12, 2013, Pepin et al.
U.S. Appl. No. 13/905,406, filed May 30, 2013, Faham et al.
U.S. Appl. No. 13/908,813, filed Jun. 3, 2013, Faham et al.
Alatrakchi, et al. T-cell clonal in patients with B-cell lymphoproliferative disorders. J Immunother. Sep. 1998;21(5):363-70.
Altman, et al. Phenotypic analysis of antigen-specific T lymphocytes. J Immunol. Jul. 1, 2011;187(1):7-9.
Arstila et al., "A direct estimate of the human αβ T cell receptor diversity," Science 286:958-961 (1999).
Arstila, et al. A direct estimate of the human alphabeta T cell receptor diversity. Science. Oct. 29, 1999;286(5441):958-61.
Ateya, et al. The good, the bad, and the tiny: a review of microflow cytometry. Anal Bioanal Chem. Jul. 2008;391(5):1485-98. doi: 10.1007/s00216-007-1827-5. Epub Jan. 29, 2008.
Bagnara, et al. IgV gene intraclonal diversification and clonal evolution in B-cell chronic lymphocytic leukaemia. Br J Haematol. Apr. 2006;133(1):50-8.
Batzoglou. The many faces of sequence alignment. Briefings in Bioinformatics. 2005; 6:6-22.
Becker-Andre, et al. Absolute mRNA quantification using the polymerase chain reaction (PCR). A novel approach by a PCR aided transcript titration assay (PATTY). Nucleic Acids Res. Nov. 25, 1989;17(22):9437-46.
Becton-Dickinson CD marker handbook. bdbiosciences.com/go/mousecdmarkers. 2010. p. 1-48.
Becton-Dickinson T-cell research tools. 2009. p. 1-16.
Beishuizen, et al. Analysis of Ig and T-cell receptor genes in 40 childhood acute lymphoblastic leukemias at diagnosis and subsequent relapse: implications for the detection of minimal residual disease by polymerase chain reaction analysis. Blood. Apr. 15, 1994;83(8):2238-47.
Ben-Ezra, et al. Effect of fixation on the amplification of nucleic acids from paraffin-embedded material by the polymerase chain reaction. J Histochem Cytochem. Mar. 1991;39(3):351-4.

(56) References Cited

OTHER PUBLICATIONS

Bentley, et al. Accurate whole human genome sequencing using reversible terminator chemistry. Nature. Nov. 6, 2008;456(7218):53-9. doi: 10.1038/nature07517.
Bereczki, et al. Optimization of PCR amplification for B- and T-cell clonality analysis on formalin-fixed and paraffin-embedded samples. Pathol Oncol Res. 2007;13(3):209-14. Epub Oct. 7, 2007.
Berget, et al. Detection of clonality in follicular lymphoma using formalin-fixed, paraffin-embedded tissue samples and BIOMED-2 immunoglobulin primers. J Clin Pathol. Jan. 2011;64(1):37-41. doi: 10.1136/jcp.2010.081109. Epub Oct. 28, 2010.
Bonarius, et al. Monitoring the T-Cell Receptor Repertoire at Single-Clone Resolution. PLoS One. Dec. 20, 2006;1:e55.
Boria, et al. Primer sets for cloning the human repertoire of T cell receptor variable regions. BMC Immunology. 2008; 9:50.
Boyd et al. Measurement and clinical monitoring of human lymphocyte clonality by massively parallel VDJ pyrosequencing. Sci Transl. Med. 1(12):12ra23 (2009).
Brehm-Stecher, et al. Single-cell microbiology: tools, technologies, and applications. Microbiology and molecular biology reviews. 2004; 68(3):538-559.
Bruggemann, et al. Standardized MRD quantification in European ALL trials: proceedings of the Second International Symposium on MRD assessment in Kiel, Germany, Sep. 18-20, 2008. Leukemia. Mar. 2010;24(3):521-35. doi:10.1038/leu.2009.268. Epub Dec. 24, 2009.
Campbell et al., "Subclonal phylogenetic structures in cancer revealed by ultra-deep sequencing," PNAS 105(35):13081-13086 (2008).
Chen, A novel approach for the analysis of T-cell reconstitution by using a T-cell receptor beta-based oligonucleotide microarray in hematopoietic stem cell transplantation. Exp Hematol. May 2007;35(5):831-41.
Choi, et al. Clonal evolution in B-lineage acute lymphoblastic leukemia by contemporaneous VH-VH gene replacements and VH-DJH gene rearrangements. Blood. Mar. 15, 1996;87(6):2506-12.
Chute, et al. Detection of immunoglobulin heavy chain gene rearrangements in classic hodgkin lymphoma using commercially available BIOMED-2 primers. Diagn Mol Pathol. Jun. 2008;17(2):65-72. doi: 10.1097/PDM.0b013e318150d695.
The International Search Report for PCT Application PCT/US2009/006053 dated Jun. 15, 2010.
Costabile, et al. Molecular approaches in the diagnosis of primary immunodeficiency diseases. Hum Mutat. Dec. 2006;27(12):1163-73.
Cronn, et al. Multiplex sequencing of plant chloroplast genomes using Solexa sequencing-by-synthesis technology. Nucleic Acids Res. Nov. 2008;36(19):e122.
Curran et al., "Nucleotide sequencing of psoriatic arthritis tissue before and during methotrexate administration reveals a complex inflammatory T cell infiltrate with very few clones exhibiting features that suggest they drive the inflammatory process by recognizing autoantigens," J Immunol 172:1935-1944 (2004).
Currier, et al. Spectratype/immunoscope analysis of the expressed TCR repertoire. Current Protocols in Immunology. 2000; Supplement 38:10.28.1-10.28.24.
Davi, et al. Lymphocytic progenitor cell origin and clonal evolution of human B-lineage acute lymphoblastic leukemia. Blood. Jul. 1996 15;88(2):609-21.
Davis, et al. Staining of cell surface human CD4 with2-F-pyrimidine-containing RNA amptamers for flow cytometry. Nucleic Acids Research. 1998; 26(17):3915-3924.
Dean, et al. Rapid amplification of plasmid and phage DNA using Phi 29 DNA polymerase and multiply-primed rolling circle amplification. Genome Res. Jun. 2001;11(6):1095-9.
Dedhia, et al. Evaluation of DNA extraction methods and real time PCR optimization on formalin-fixed paraffin-embedded tissues. Asian Pac J Cancer Prev. Jan.-Mar. 2007;8(1):55-9.

Deng et al., "Gene profiling involved in immature CD4+ T lymphocyte responsible for systemic lupus erythematosus," Molecular Immunology 43:1497-1507 (2006).
Dohm, et al. Substantial biases in ultra-short read data sets from high throughput DNA sequencing. Nucleic Acids Research. 2008; 36:e105.
Dou, et al. Analysis of T cell receptor Vbeta gene usage during the course of disease in patients with chronic hepatitis B. J Biomed Sci. 1998 Nov-Dec;5(6):428-34.
Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.
Du et al., "TCR spectratyping revealed T lymphocytes associated with graft-versus-host disease after allogeneic hematopoietic stem cell transplantation," Leukemia & Lymphoma 48(8):1618-1627 (2007).
Edd, et al. Controlled encapsulation of single cells into monodisperse picoliter drops. Lap Chip. 2008; 8(8):1262-1264.
Eid, et al. Real-time DNA sequencing from single polymerase molecules. Science. Jan. 2, 2009;323(5910):133-8. doi: 10.1126/science.1162986. Epub Nov. 20, 2008.
European office action dated Mar. 28, 2012 for EP Application No. 09764927.1.
Freeman, et al. Profiling the T-cell receptor beta-chain repertoire by massively parallel sequencing. Genome Res. Oct. 2009;19(10):1817-24. doi: 10.1101/gr.092924.109. Epub Jun. 18, 2009.
Fridman, et al. Prognostic and predictive impact of intra- and peritumoral immune infiltrates. Cancer Res. Sep. 1, 2011;71(17):5601-5. doi: 10.1158/0008-5472.CAN-11-1316. Epub Aug. 16, 2011.
Fritz et al., "Alterations in the spinal cord T cell repertoire during relapsing experimental autoimmune encephalomyelitis," J Immunol 164:6662-6668 (2000).
Garcia-Castello, et al. Detection of clonal immunoglobulin and T-cell receptor gene recombination in hematological malignancies: monitoring minimal residual disease. Cardiovascular & Haematological Disorders—Drug Targets. 2009; 9:124-135.
Gerlinger, et al. How Darwinian models inform therapeutic failure initiated by clonal heterogeneity in cancer medicine. Br J Cancer. Oct. 12, 2010;103(8):1139-43. doi: 10.1038/sj.bjc.6605912. Epub Sep. 28, 2010.
Germano, et al. Clonality profile in relapsed precursor-B-ALL children by GeneScan and sequencing analyses. Consequences on minimal residual disease monitoring. Leukemia. Aug. 2003;17(8):1573-82.
Gilbert, et al. The isolation of nucleic acids from fixed, paraffin-embedded tissues—which methods are useful when? PLoS One. Jun. 20, 2007;2(6):e537.
Giuggio, et al. Evolution of the intrahepatic T cell repertoire during chronic hepataitis C virus infection. Viral Immunol. 2005;18(1):179-89.
Golembowski, et al. Clonal evolution in a primary cutaneous follicle center B cell lymphoma revealed by single cell analysis in sequential biopsies. Immunobiology. Apr. 2000;201(5):631-44.
Gonzalez, et al. Incomplete DJH rearrangements as a novel tumar target for minimal residual disease quantitation in multiple myeloma using real-time PCR. Leukemia. 2003; 17:1051-1057.
Gonzalez, et al. Incomplete DJH rearrangements of the IgH gene are frequent in multiple myelioma patients: immunobiligcal characteristics and clinical applications. Leukemia. 2003; 17:1398-1403.
Gorski, et al. Circulating T cell repertoire complexity in normal individuals and bone marrow recipients analyzed by CDR3 size spectratyping. Correlation with immune status. J Immunol. May 15, 1994;152(10):5109-19.
Gratama, et al. Flow cytometric enumeration of antigen-specific T lymphocytes. Cytometry A. Mar. 2004;58(1):79-86.
Green, et al. Clonal diversity of Ig and T-cell-receptor gene rearrangements identifies a subset of childhood B-precursor acute lymphoblastic leukemia with increased risk of relapse. Blood. Aug. 1, 1998;92(3):952-8.

(56) References Cited

OTHER PUBLICATIONS

Guo, et al. Sequence changes at the V-D junction of the VH1 heavy chain of anti-phosphocholine antibodies alter binding to and protection against Streptococcus pneumoniae. Int Immunol. May 1997;9(5):665-77.
Gurrieri, et al. Chronic lymphocytic leukemia B cells can undergo somatic hypermutation and intraclonal immunoglobulin V(H)DJ(H) gene diversification. J Exp Med. Sep. 2, 2002;196(5):629-39.
Halldorsdottir, et al. Application of BIOMED-2 clonality assays to formalin-fixed paraffin embedded follicular lymphoma specimens: superior performance of the IGK assays compared to IGH for suboptimal specimens. Leuk Lymphoma. Jul. 2007;48(7): 1338-43.
He, et al. IgH gene rearrangements as plasma biomarkers in Non-Hodgkin's lymphoma patients. Oncotarget. Mar. 2011;2(3):178-85.
Holt, "Q &A: BC cancer agency's Robert Holt on sequencing the immune repertoire in immune reconstitution," Genome Web (www.genomeweb.com) Jun. 30, 2009.
Hosono, et al. Unbiased whole-genome amplification directly from clinical samples. Genome Res. May 2003;13(5):954-64. Epub Apr. 14, 2003.
Howe, et al. T cell receptor clonotype analysis of T cell responses: Diagnostic application of a clonotypic database. Blood. 2003; 102:Abstract 3918.
Huijsmans, et al. Comparative analysis of four methods to extract DNA from paraffin-embedded tissues: effect on downstream molecular applications. BMC Res Notes. Sep. 14, 2010;3:239. doi: 10.1186/1756-0500-3-239.
Illumina. Data Sheet: Sequencing. Genomic Sequencing. Pub. No. 770.2008-016 Copyright 2010. Reference states: "Current as of Jan. 30, 2009."
International search report and written opinion dated Sep. 22, 2011 for PCT Application No. US11/000791.
International search report and written opinion dated Oct. 19, 2011 for PCT Application No. US11/000792.
Ishii et al., "Isolation and expression profiling of genes upregulated in the peripheral blood cells of systemic lupus erythematosus patients," DNA Research 12:429-439 (2005).
Jacobi et al., "Activated memory B cell subsets correlate with disease activity in systemic lupus erythematosus: delineation by expression of CD27, IgD, and CD95," Arthritis & Rheumatism 58(6):1762-1773 (2008).
Jacobi et al., "Correlation between circulating CD27high plasma cells and disease activity in patients with systemic lupus erythematosus," Arthritis & Rheumatism 48(5):1332-1342 (2003).
Jena, et al. Amplification of genes, single transcripts and cDNA libraries from one cell and direct sequence analysis of amplified products derived from one molecule. J. Immunol. Methods. 1996; 190:199-213.
Kato et al., "Analysis of accumulated T cell clonotypes in patients with systemic lupus erythematosus," Arthritis & Rheumatism 43(12):2712-2721 (2000).
Kedzierska, et al. Tracking phenotypically and functionally distinct T cell subsets via T cell repertoire diversity. Mol Immunol. Feb. 2008;45(3):607-18. Epub Aug. 24, 2007.
Kim, et al An efficient and reliable DNA extraction method for preimplantation genetic diagnosis: a comparison of allele drop out and amplification rates using different single cell iysis methods. Fertility and Sterility. 2009; 92: 814-818.
Kim, et al. Polony multiplex analysis of gene expression (PMAGE) in mouse hypertrophic cardiomyopathy. Science. Jun. 8, 2007;316(5830):1481-4.
Kneba, et al. Analysis of rearranged T-cell receptor beta-chain genes by polymerase chain reaction (PCR0 DNA sequencing and automated high resolution PCR fragment analysis. Blood. 1995; 86:3930-3937.
Kobari, et al. T cells accumulating in the inflamed joints of a spontaneous murine model of rheumatoid arthritis become restricted to common clonotypes during disease progression. Int Immunol. Jan. 2004 ;16(1):131-8.

Langerak, et al. Immunoglobulin/T-cell receptor clonality diagnostics. Exoert Opin. Med. Diagn. 2007; 1(3):451-461.
Laplaud et al., "Blood T-cell receptor β chain transcriptome in multiple sclerosis. Characterization of the T cells with altered CDR3 length distribution," Brain 127:981-995 (2004).
Laplaud et al., "Serial blood T cell repertoire alterations in multiple sclerosis patients; correlation with clinical and MRI parameters," J Neroimmunol 177:151-160 (2006).
Lassmann, et al. Application of BIOMED-2 primers in fixed and decalcified bone marrow biopsies: analysis of immunoglobulin H receptor rearrangements in B-cell non-Hodgkin's lymphomas. J Mol Diagn. Nov. 2005;7(5):582-91.
Leisner, et al. One-pot, mix-and-read peptide-MHC tetramers. PLoS One. Feb. 27, 2008;3(2):e1678. doi: 10.1371/journal.pone.0001678.
Leone, et al. Molecular beacon probes combined with amplification by NASBA enable homogeneous, real-time detection of RNA. Nucleic Acids Res. May 1, 1998;26(9):2150-5.
Li, et al. An improved one-tube RT-PCR protocol for analyzing single-cell gene expression in individual mammalian cells. Anal. Bioanal. Chem. 2010; 397: 1853-1859.
Li, et al. Clonal rearrangements in childhood and adult precursor B acute lymphoblastic leukemia: a comparative polymerase chain reaction study using multiple sets of primers. Eur J Haematol. Oct. 1999;63(4):211-8.
Li, et al. Detailed clonality analysis of relapsing precursor B acute lymphoblastic leukemia: implications for minimal residual disease detection. Leukemia Research. 2001; 25:1033-1045.
Li, et al. Sequence analysisn of clonal immunoglobulin and T-cell receptor gene rearrangements in children with acute lymphoblastic leukemia at diagnosis and at relapse: implications for pathogenesis and for the clinical utility of PCR-based methods of minimal residual disease detection. Blood. 2003; 102:4520-4526.
Liedtke, et al. A comparison of methods for RNA extraction from lymphocytes for RT-PCR. PCR Methods Appl. Dec. 1994;4(3):185-7.
Lovisa, et al. IGH and IGK gene rearrangements as PCR targets for pediatric Burkitt's lymphoma and mature B-ALL MRD analysis. Lab Invest. Oct. 2009;89(10):1182-6. Epub Aug. 10, 2009.
Luo et al., "Analysis of the interindividual conservation of T cell receptor α- and β-chain variable regions gene in the peripheral blood of patients with systemic lupus erythematosus," Clin Exp Immunol 154:316-324 (2008).
Margulies, et al. Genome sequencing in microfabricated high-density picolitre reactors. Nature. Sep. 15, 2005;437(7057):376-80. Epub Jul. 31, 2005.
Mato et al., "Correlation of clonal T cell expansion with disease activity in systemic lupus erythematosus," Int Immunol 9(4):547-554 (1997).
Matolcsy, et al. Clonal evolution of B cells in transformation from low- to high-grade lymphoma. Eur J Immunol. Apr. 1999;29(4):1253-64.
Matsumoto et al., "CDR3 spectratyping analysis of the TCR repertoire in myasthenia gravis," J Immunol 176:5100-5107 (2006).
Matsumoto et al., "Complementarity-determining region 3 spectratyping analysis of the TCR repertoire in multiple sclerosis," J Immunol 170:4846-4853 (2003).
Menezes et al., "A public T cell clonotype within a heterogeneous autoreactive repertoire is dominant in driving EAE," J Clin Invest 117(8):2176-2185 (2007).
Michalek, et al. Detection and long-term in vivo monitoring of individual tumor-specific T cell clones in patients with metastatic melanoma. J Immunol Jun. 1, 2007;178(11):6789-95.
Moody, et al. Antigen-specific B cell detection reagents: use and quality control. Cytometry A. Nov. 2008;73(11):1086-92. doi: 10.1002/cyto.A.20599.
Moss, et al. The human T cell reeptor in health and disease. Annu. Rev. Immunol. 1992; 10:71-96.
Muraro et al., "Molecular tracking of antigen-specific T cell clones in neurological immune-mediated disorders," Brain 126:20-31 (2003).
Nardi, et al. Quantitative monitoring by polymerase colony assay of known mutations resistant to ABL kinase inhibitors. Oncogene. Jan. 31, 2008;27(6):775-82. Epub Aug. 6, 2007, 1-8.

(56) References Cited

OTHER PUBLICATIONS

Nguyen, et al. Identification of errors introduced during high throughput sequencing of the T cell receptor repertoire. BMC Genomics. Feb. 11, 2011;12:106.
Notification of Grant dated Jul. 26, 2011 for patent serial No. GB 2467704.
Novak, et al. Single-cell multiplex gene detection and sequencing with microfluidically generated agarose emulsions. Angewandte Chemie. 2011; 50: 390-395, with supplemental material.
Office action dated Mar. 13, 2013 for U.S. Appl. No. 13/763,978.
Office action dated Apr. 22, 2013 for U.S. Appl. No. 13/214,111.
Office action dated May 9, 2012 for U.S. Appl. No. 13/100,395.
Office action dated Jun. 6, 2013 for U.S. Appl. No. 13/100,365.
Office action dated Jun. 6, 2013 for U.S. Appl. No. 13/100,389.
Office action dated Jun. 20, 2013 for U.S. Appl. No. 13/214,111.
Office action dated Sep. 15, 2011 for U.S. Appl. No. 12/615,263.
Office action dated Dec. 6, 2012 for U.S. Appl. No. 13/100,395.
Ogle, et al. Direst measurement of lymphocyte receptor diversity. Nucleic Acids Research. 2003; 31(22):e139.
Okajima et al., "Analysis of T cell receptor Vβ diversity in peripheral CD4+ and CD8+ T lymphocytes in patients with autoimmune thyroid diseases," Clin Exp Immunol 155:166-172 (2008).
Packer et al., "Optimized clonotypic analysis of T-cell receptor repertoire in immune reconstitution," Exp. Hematol 35(3):516-521 (2007).
Pan, et al. A new FACS approach isolates hESC derived endoderm using transcription factors. PLoS One. Mar. 9, 2011;6(3):e17536. doi: 10.1371/journal.pone.0017536.
Pels, et al. Clonal evolution as pathogenetic machanism in relapse of primary CNS lymphoma. Neurology. Jul. 13, 2004;63(1):167-9.
Pira, et al. Human naive CD4 T-cell clones specific for HIV envelope persist for years in vivo in the absence of antigenic challenge. J Acquir Immune Defic Syndr. Oct. 1, 2005;40(2):132-9.
Pop, et al. Bioinformatics challenges of new sequencing technology. Trends Genet. Mar. 2008;24(3):142-9.
Ray, et at. Single cell multiplex PCR amplification of five dystrophin gene exons combined with gender determination. Molecular Human Reproduction. 2001; 7(5): 489-494.
Reinartz, et al. Massively parallel signature sequencing (MPSS) as a tool for in-depth quantitative gene expression profiling in all organisms. Brief Funct Genomic Proteomic. Feb. 2002;1(1):95-104.
Ria, et al. Collagen-specific T-cell repertoire in blood and synovial fluid varies with disease activity in early rheumatoid arthritis. Arthritis Res Ther. 2008;10(6):R135. Epub Nov. 17, 2008.
Rickison, et al. Human cytotoxic T lymphocyte responses to Epstein-Barr virus infection. Annu Rev Immunol. 1997;15:405-31.
Risitano et al., "In-vivo dominant immune responses in aplastic anaemia: molecular tracking of putatively pathogenetic T-cell clones by TCR β-CDR3 sequencing," Lancet 364:355-364 (2004).
Robins et al., "Comprehensive assessment of T-cell receptor beta-chain diversity in alphabeta T cells," Blood 114(19):4099-4107 (2009).
Rosenquist, et al. Clonal evolution as judged by immunoglobulin heavy chain gene rearrangements in relapsing precursor-B acute lymphoblastic leukemia. Eur J Haematol. Sep. 1999;63(3):171-9.
Rougemont, et al. Probabilistic base calling of Solexa sequencing data. BMC Bioinformatics. 2008; 9:431.
Ryan, et al. Clonal evolution of lymphoblastoid cell lines. Lab Invest. Nov. 2006;86(11):1193-200. Epub Oct. 2, 2006.
Satoh, et al. Pretreatment with restriction enzyme or bovine serum albumin for effective PCR amplification of Epstein-Barr virus DNA in DNA extracted from paraffin-embedded gastric carcinoma tissue. J Clin Microbiol. Nov. 1998;36(11):3423-5.
Schaufelberger, et al. An uneven expression of T cell receptor V genes in the arterial wall and peripheral blood in giant cell arteritis. Inflammation. Dec. 2008;31(6):372-83.
Scholler, et al. Analysis of T cell receptor alpha beta variability in lymphocytes infiltrating melanoma primary tumours and metastatic lesions. Cancer Immunol Immunother. Oct. 1994;39(4):239-48.

Schwab et al., "CD8+ T-cell clones dominate brain infiltrates in Rasmussen encephalitis and persist in the periphery," Brain 132:1236-1246 (2009).
Schweiger, et al. Genome-wide massively parallel sequencing of formaldehyde fixed-paraffin embedded (FFPE) tumor tissues for copy-number- and mutation-analysis. PLoS One. 2009;4(5):e5548. doi: 10.1371/journal.pone.0005548. Epub May 14, 2009.
Shen, et al. Comparing platforms for C. elegans mutant identification using high-throughput whole-genome sequencing. PLoS One. 2008;3(12):e4012.
Skulina et al., "Multiple sclerosis: brain-infiltrating CD8+ T cells persist as clonal expansions in the cerebrospinal fluid and blood," PNAS 101(8):2428-2433 (2004).
Smith, et al. Comparison of biosequences. Advances in Applied Mathematics. 1981; 2:482-489.
Srinivasan, et al. Effect of fixatives and tissue processing on the content and integrity of nucleic acids. Am J Pathol. Dec. 2002;161(6):1961-71.
Steenbergen, et al. Distinct ongoing Ig heavy chain rearrangement processes in childhood B-precursor acute lymphoblastic leukemia. Blood. Jul. 15, 1993;82(2):581-9.
Steward, et al. A polymerase chain reaction study of the stability of Ig heavy-chain and T-cell receptor delta gene rearrangements between presentation and relapse of childhood B-lineage acute lymphoblastic leukemia. Blood. Mar. 1, 1994;83(5):1355-62.
Struyk, et al. T cell receptors in rheumatoid arthritis. Arthritis Rheum. May 1995;38(5):577-89.
Sumida et al., "T cell receptor repertoire of infiltrating T cells in lips of Sjögren's syndrome patients," J Clin Invest 89:681-685 (1992).
Sumida et al., "T cell receptor Vα repertoire of infiltrating T cells in labial salivary glands from patients with Sjögren's syndrome," J Rheumatol 21: 1655-1661 (1994).
Szczepanski, et al. Comparative analysis of Ig and TCR gene rearrangements at diagnosis and at relapse of childhood precursor-B-ALL provides improved strategies for selection of stable PCR targets for monitoring of minimal residual disease. Blood. Apr. 1, 2002;99(7):2315-23.
Szczepanski, et al. Why and how to quantify minimal residual disease in acute lymphoblastic leukemia? Leukemia. Apr. 2007;21(4):622-6. Epub Feb. 15, 2007.
Tackenberg et al., "Clonal expansions of CD4+ β helper T cells in autoimmune myasthenia gravis," Eur J Immunol 37:849-863 (2007).
Tajiri, et al. Cell-microarray analysis of antigen-specific B-cells: single cell analysis of antigen receptor expression and specificity. Cytometry Part A. 2007; 71A: 961-967.
Thornhill, et al. A comparison of different lysis buffers to assess allele dropout from single cells for preimplantation genetic diagnosis. Prenatal Diagnosis. 2001; 21: 490-497.
Tokimitsu, et al. Single lymphocyte analysis with a microwell array chip. Cytometry. 2007; Part A, 71A: 1003-1010.
UK Combined Search Report and Office action dated May 26, 2011 for UK application No. GB1105068.9.
UK office action dated May 25, 2011 for UK application No. GB1009641.0.
UK office action dated Oct. 20, 2010 for UK application No. GB1009641.0.
UK Search Report and office action dated Jan. 12, 2012 for UK application No. GB1120209.0.
Umibe et al., "Clonal expansion of T cells infiltrating in the airways of non-atopic asthmatics," Clin Exp Immunol 119:390-397 (2000).
Van Der Velden, et al. Analysis of minimal residual disease by Ig/TCR gene rearrangements: guidelines for interpretation of real-time quantitative PCR data. Leukemia. Apr. 2007;21(4):604-11. Epub Feb. 8, 2007.
Van Der Velden, et al. Detection of minimal residual disease in hematologic malignancies by real-time quantitative PCR: principles, approaches, and laboratory aspects. Leukemia. Jun. 2003;17(6):1013-34.
Wang, et al. Balanced-PCR amplification allows unbiased identification of genomic copy changes in minute cell and tissue samples. Nucleic Acids Res. May 21, 2004;32(9):e76.

(56) References Cited

OTHER PUBLICATIONS

Wang, et al. Quantitative measurement of pathogen-specific human memory T cell repertoire diversity using a CDR3 beta-specific microarray. BMC Genomics. Sep. 19, 2007;8:329.
Warren et al., "Profiling model T-cell metagenomes with short reads," Bioinformatics 25(4):458-464 (2009).
Weinstein et al., "High-throughput sequencing of the zebrafish antibody repertoire," Science 324:807-810 (2009).
Wells, et al. Strategies for preimplantation genetic diagnosis of single gene disorders by DNA amplification. Prenatal Diagnosis. 1998; 18: 1389-1401.
Wetmur, et al. An emulsion polymerase chain reaction-based method for molecular haplotyping. Methods in Molecular Biology. 1996; 410: 351-361.
Wetmur, et al. Linking emulsion PCR haplotype analysis. chapter 11, in Park (editor), PCR Protocols, Methods En Molecular Biology. 2011; 687: 165-175.
Wetmur, et al. Molecular haplotyping by linking emulsion PCR: analysis of paraoxonase 1 haplotypes and phenotypes. Nucleic Acids Research. 2005; 33(8):2615-2619.
Wlodarski, et al. Molecular strategies for detection and quantitation of the clonal cytotoxic T-cell responses in aplastic anemia and myelodysplastic syndrome. Blood. 2006; 108:2632-2641.
Wlodarski, et al. Pathologic clonal cytotoxic T-cell responses: nonrandom nature of the T-cell-receptor restriction in large granular lymphocyte leukemia. Blood. 2005; 106:2769-2779.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.
Wu, et al. High-throughput sequencing detects minimal residual disease in acute T lymphoblastic leukemia. Sci Transl Med. May 16, 2012;4(134):134ra63. doi: 10.1126/scitranslmed.3003656.
Yassai, et al. A clonotype nomenclature for T cell receptors. Immunogenetics. Jul. 2009;61(7):493-502. doi: 10.1007/s00251-009-0383-x. Epub Jul. 1, 2009.
Yin et al., "Antiretroviral therapy restores diversity in the T-cell receptor Vβ repertoire of CD4 T-cell subpopulations among human immunodeficiency virus type 1-infected children and adolescents," Clin Vac Immunol 16(9):1293-1301 (2009).
Yon, et al. Precise gene fusion by PCR. Nucleic Acids Research. 1989; 17(12):4895.
Yu, et al. Tumor-infiltrating T lymphocytes: friends or foes? Lab Invest. Mar. 2006;86(3):231-45.
Zeng, et al. High-performance single cell genetic analysis using microfluidic emulsion generator arrays. Anal. Chem. 2010; 82:3183-3190.
Zhou, et al. High throughput analysis of TCR-beta rearrangement and gene expression in single cells. 2006; 86:314-321.
Zimmerman, et al. Technical aspects of quantitative competitive PCR. Biotechniques. 1996; 21:268-279.
PCT/US2014/017416, Appln filed Feb. 20, 2014, Pepin et al.
U.S. Appl. No. 14/075,075, filed Nov. 8, 2013, Faham et al.
U.S. Appl. No. 14/089,517, filed Nov. 25, 2013, Han.
U.S. Appl. No. 14/173,712, filed Feb, 5, 2014, Faham et al.
U.S. Appl. No. 14/176,551, filed Feb. 10, 2014, Faham et al.
U.S. Appl. No. 14/185,846, filed Feb. 20, 2014, Pepin et al.
U.S. Appl. No. 14/197,615, filed Mar. 5, 2014, Carlton et al.
U.S. Appl. No. 14/202,990, filed Mar. 10, 2014, Zheng.
U.S. Appl. No. 14/242,520, filed Apr. 1, 2014, Klinger et al.
U.S. Appl. No. 14/343,286, filed Mar. 6, 2014, Faham et al.
U.S. Appl. No. 14/350,516, filed Apr. 8, 2014, Faham et al.
U.S. Appl. No. 14/350,785, filed Apr. 9, 2014, Faham et al.
Office action dated Mar. 20, 2013 for U.S. Appl. No. 13/487,980.
Brisco, et al. "Outcome prediction in childhood acute lymphoblastic leukaemia by molecular quantification of residual disease at the end of induction", Lancet, 343:196-200 (1994).
EP Application No. 12841014.9, Extended European Search Report dated May 4, 2015, 11 pages.
US 8,642,750, 02/2014, Faham et al. (withdrawn).
Abath et al. "Single-tubed nested PCR using immobilized internal primers", Biotechniques, 33(6): 1210-2, 1214 (2002).
Ahmadzadeh et al. "FOXP3 expression accurately defines the population of intratumoral regulatory T cells that selectively accumulate in metastatic melanoma lesions", Blood, 112(13): 4953-4960 (2008).
Altin et al. "The role of CD45 and CD45-associated molecules in T cell activation", Immunology and Cell Biology, 75: 430-445 (1997).
Arnaout. "Specificity and overlap in gene segment-defined antibody repertoires", BMC Genomics, 6: 148 (2005).
Baldauf, "Phylogeny for the faint of heart: a tutorial," Trends in Genetics, 19(6): 345-351 (2003).
Benichou, J. et al., "The restricted DH gene reading frame usage in the expressed human antibody repertoire is selected based upon its amino acid content", J Immunol., 190(11): 5567-77, 29 pages (2013).
Brochet et al. "IMGT/V-QUEST: the highly customized and integrated system for IG and TR standardized V-J and V-D-J sequence analysis", Nucleic Acids Research, vol. 36, Web Server issue W503-W508 (2008).
Boudinot et al. "New perspectives for large-scale repertoire analysis of immune receptors", Molecular Immunology, 45: 2437-2445 (2008).
Bradfield, et al. "Graft-versus-leukemia effect in acute lymphoblastic leukemia: the importance of tumor burden and early detection", Leukemia, 18(6): 1156-1158 (2004).
Brentjens, et al. "CD19-targeted T cells rapidly induce molecular remissions in adults with chemotherapy-refractory acute lymphoblastic leukemia", Sci Transl Med., 5(177): 177ra38 (2013). doi: 10.1126/scitranslmed.3005930.
Brockman et al, "Quality scores and SNP detection in sequencing-by-synthesis systems," Genome Research, 18: 763-770 (2008).
Brownie et al. "The elimination of primer-dimer accumulation in PCR", Nucleic Acids Research, 25(16): 3235-3241 (1997).
Brüggemann, et al. "Rearranged T-cell receptor beta genes represent powerful targets for quantification of minimal residual disease in childhood and adult T-cell acute lymphoblastic leukemia", Leukemia, 18(4): 709-719 (2004).
Carlson et al. "Profiling the repertoire of TCRB usage in induced and natural Treg cells", The Journal of Immunology, 186: 62.5, Abstract (2011).
Carlson, et al. "Immune Profiling Suggests an IGH Signaling-Dependent Subtype of Aggressive B-ALL", Blood, 120: 1428, Abstract (2012).
Carlson, et al. "Deep sequencing of the human TCRγ and TCRβ repertoires provides evidence that TCRβ rearranges after αβ, γδT cell commitment". Presented at the ASHG 2011 Conference. Oct., 2011. Poster. 1 page.
Carlson, et al. "Detection of tumor tagging clones in multiple myeloma via high throughput sequencing is robust to significant levels of SHM", Presented for the 2014 ASH Annual Meeting. Poster. 1 page. Dec. 5-9, 2014.
Chan et al. "Evaluation of Nanofluidics Technology for High-Throughput SNP Genotyping in a Clinical Setting", The Journal of Molecular Diagnostics, 13(3): 305-312 (2011).
Chen et al. "Identification of racehorse and sample contamination by novel 24-plex STR system", Forensic Science International: Genetics, 4:158-167 (2010).
Citri et al. "Comprehensive qPCR profiling of gene expression in single neuronal cells", Nature Protocols, 7(1): 118-127 (2012).
Clemente, et al. "Deep sequencing of the T-cell receptor repertoire in CD8+T-large granular lymphocyte leukemia identifies signature landscapes", Blood, 122(25): 4077-85 (2013). doi: 10.1182/blood-2013-05-506386. Epub Oct. 22, 2013.
Cooper, et al. "BRAF inhibition is associated with increased clonality in tumorin filtrating lymphocytes", Oncoimmunology, 2(10):e26615 (2013). Epub Oct. 15, 2013.
Dahl et al. "Multiplex amplification enabled by selective circularization of large sets of genomic DNA fragments", Nucleic Acids Res., 33(8): e71 (2005).

(56) References Cited

OTHER PUBLICATIONS

Damle et al. "B-cell chronic lymphocytic leukemia cells express a surface membrane phenotype of activated, antigen-experienced B lymphocytes", *Blood*, 99(11): 4087-93 (2002).
Davila, et al. Efficacy and toxicity management of 19-28z CART cell therapy in B cell acute lymphoblastic leukemia, Sci Transl Med., 6(224):224ra25 (2014). doi: 10.1126/scitranslmed.3008226.
De Bona et al. "Optimal spliced alignments of short sequence reads", *Bioinformatics*, 9(Suppl 10):07, 2 pages (2008).
Decoste et al. "Relative and Absolute Quantitative Real-Time PCR-Based Quantifications of hcnC and phlD Gene Transcripts in Natural Soil Spiked with *Pseudomonas* sp. Strain LBUM300", *Applied and Environmental Microbiology*, 77(1): 41-47 (2011).
DeKOSKY et al. "High-throughput sequencing of the paired human immunoglobulin heavy and light chain repertoire", *Nature Biotechnology*, 31(2): 166-169 (2013).
Delaney, et al. "Evolution and Clinical Implications of the T cell Repertoire Following Cord Blood Transplant", Biology of Blood and Marrow Transplant, vol. 19, Issue 2, S201-S202. Published Feb. 2013.
Desmarais, et al. "Deep profiling of the mouse TCR13 CDR3 region in thymus and spleen". Oct. 2010. Poster. 1 page.
Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.
Desmarais and Robins. "High-throughput sequencing of memory and naïve T cell receptor repertoires at the RNA and DNA levels reveals differences in relative expression of expanded TCR clones", The Journal of Immunology, 188: 178.12 (2012).
Dictor et al. "Resolving T-cell receptor clonality in two and genotype in four multiplex polymerase chain reactions", *Haematologica*, 90(11): 1524-1532 (2005).
Diluvio et al. "Identical TCRβ-chain rearrangements in streptococcal anginaand skin lesions of patients with psoriasis vulgaris", *J Immunol.*, 176(11 ): 7104-11 (2006).
Do and Batzoglou. "What is the expectation maximization algorithm'?", *Nature Biotechnology*, 26(8): 897-899 (2008).
Drossman, et al. "High-speed separations of DNA sequencing reactions by capillary electrophoresis", *Anal Chem.*, 62(9): 900-903 (1990).
Dudgeon, et al. "The evolution of thymic lymphomas in p53 knockout mice", Genes Dev., 28(23): 2613-20 (2014). doi: 10.1101/gad.252148.114.
Eisenstein. "Personalized, sequencing-based immune profiling spurs startups", Nat Biotechnol., 31(3):184-6 (2013). doi: 10.1038/nbt0313-184b.
Elkord et al. "T regulatory cells in cancer: recent advances and therapeutic potential", *Expert Opinion on Biological Therapy*, 10(11): 1573-1586 (2010).
Emerson, et al. "Correlation of TCR diversity with immune reconstitution after cord blood transplant", Presented at the American Society of Clinical Oncology's annual meeting. May 2012. Poster. 1 page.
Emerson, et al. "CD4+ and CD8+ T cell β antigen receptors have different and predictable V and J gene usage and CDR3 lengths", Presented at the Annual Meeting of the American Association of Immunologists 2012 in Boston, MA May 2012. Poster.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, et al. TCR repertoire diversity assessed with immunosequencing is associated with patient mortality following cord blood transplant. Presented for the 2014 ASH Annual Meeting. Poster. 1 page. Dec. 5-9, 2014.
Estorninho, et al. "A novel approach to tracking antigen-experienced CD4 T cells into functional compartments via tandem deep and shallow TCR clonotyping", J Immunol., 191(11): 5430-40 (2013). doi: 10.4049/jimmunol.1300622. Epub Oct. 25, 2013.
Erlich, et al. "Alta-Cyclic: a self-optimizing base caller for next-generation sequencing", *Nat Methods.*, 5(8): 679-682 (2008). doi: 10.1038/nmeth.1230. Epub Jul. 6, 2008.
European Application No. 09764927.1, Notice of Opposition dated Oct. 14, 2014, Reference# 547-7.
European Application No. 09764927.1, Notice of Opposition dated Oct. 14, 2014, Reference# BRO-0001EP.
European Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", *Lung Cancer*, 59(1): 32-40 (2008).
European Patent Application No. 12856834.2, Extended European Search Report dated Jul. 7, 2015, 8 pages.
European Patent Application No. 13195379.6, European Search Report and Opinion dated Mar. 13, 2014, 6 pages.
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated Nov. 23, 2015.
Ewing and Green, "Base-calling of automated sequencer traces using Phred. I. Accuracy Assessment," Genome Research, 8: 175-185 (1998).
Felsenstein, et al. "Evolutionary Trees from DNA Sequences: A Maximum Likelihood Approach", J Mol Evol, 17:368-376 (1981).
Ferradini et al. "Analysis of T Cell Receptor Variability in Tumor-infiltrating Lymphocytes from a Human Regressive Melanoma", *J. Clin. Invest.*, pp. 1183-190 (1993).
Fisher et al. "The Relation Between the Number of Species and the Number of Individuals in a Random Sample of an Animal Population", *Journal of Animal Ecology*, 12(1): 42-58 (1943).
Flicek and Birney, "Sense from sequence reads: methods for alignment and assembly," Nature Methods Supplement, 6(11s): S6-S12 (2009).
Frederiksson et al., Multiplex amplification of all coding sequences within 10 cancer genes by Gene-Collector, Nucleic Acids Research, 35(7): e47 (2007).
Furmanski, et al. "Public T cell receptor β-chains are not advantaged during positive selection", *The Journal of Immunology*, 180(2): 1029-39 (2008).
GIGA—Roche 454 FLX technology how it works. Fiche technique du Centre Interdisciplinaire de Genoproteomique Appliquee (Universite de Liege, Belgique). Accessed Oct. 15, 2014.
Gomes, et al. "Single-tube nested PCR using immobilized internal primers for the identification of dengue virus serotypes", *J Virol Methods.*, 145(1):76-9 (2007). Epub Jun. 15, 2007.
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Grupp, et al. "Chimeric antigen receptor-modified T cells for acute lymphoid leukemia", N Engl J Med., 368(16):1509-18 (2013). doi: 10.1056/NEJMoa1215134. Epub Mar. 25, 2013.
Grupp, et al. "Adoptive transfer of autologous T cells improves T-cell repertoire diversity and long-term B-cell function in pediatric patients with neuroblastoma", Clin Cancer Res., 18(24):6732-41 (2012). doi: 10.1158/1078-0432.CCR-12-1432. Epub Oct. 23, 2012.
Gupta, Pushpendra K. "Single-molecule DNA sequencing technologies for future genomics research", *Trends Biotechnol.*, 26(11): 602-611 (2008). doi: 10.1016/j.tibtech.2008.07.003. Epub Aug. 21, 2008.
Harris et al. "Single-Molecule DNA Sequencing of a Viral Genome", *Science*, 320: 106-109 (2008).
Hathcock, et al. "ATM influences the efficiency of TCRβ rearrangement, subsequent TCRβ-dependent T cell development, and generation of the pre-selection TCRβ CDR3 repertoire", PLoS One, 8(4):e62188 (2013). doi: 10.1371/joumal.pone.0062188. Print 2013.
Heger. "Roche's 454 Eyes Immune Repertoire Sequencing as Key Application for Long-Read Platform". Feb. 2, 2010. 4 pages. http://www.genomeweb.com/print/932624.

(56) References Cited

OTHER PUBLICATIONS

Holder and Lewis. "Phylogeny estimation: traditional and bayesian approaches", Nat Rev Genet., 4(4): 275-84 (2009).

Huse et al. "Accuracy and quality of massively parallel DNA pyrosequencing", Genome Biology, 8: R143 (2007).

Illumina. Data Sheet, "TruSeq™ exome enrichment kit", 5 pages (2011).

Illumina Systems & Software, Technology Spotlight, DNA Sequencing with Solexa® Technology, Illumina, Inc., Pub. No. 770-2007-002, 4 pages (2007).

Illumina. "Technical Note: Systems and Software. Calling sequencing SNPs", 3 pages (2010).

Jabara et al. "Accurate sampling and deep sequencing of the HIV-1 protease gene using a Primer ID", PNAS, 108(50): 20166-20171 (2011).

Jones, et al. "Human autoimmunity after lymphocyte depletion is caused by homeostatic T-cell proliferation", Proc Natl Acad Sci USA, 110(50) :20200-5 (2013). doi: 10.1073/pnas.1313654110. Epub Nov. 26, 2013.

Jurkat, Clone 6-1 (ATCC TIB-152) Webpage retrievable from the ATCC under http://www.lgcstandards-atcc.org/Products/ All MB-152. aspx#characteristics. Accessed Oct. 14, 2014.

Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt. 2012.06.005. Epub Jun. 12, 2012.

Kirsch, et al. "Defining immunoglobulin somatic hypermutation in de novo diffuse large b-cell lymphoma patients: potential application prognosis and risk stratification", Presented for the 2014 ASH Annual Meeting. Poster. 1 page. Dec. 5-9, 2014.

Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.

Kita, et al. "T cell receptor clonotypes in skin lesions from patients with systemic lupus erythematosus", Journal of Investigative Dermatology,110(1): 41-6 (1988).

Koboldt et al., "VarScan: variant detection in massively parallel sequencing of individual and pooled samples", Bioinformatics, 25(17): 2283-2285 (2009).

Kojima et al. "PCR amplification from single DNA molecules on magnetic beads in emulsion: application for high-throughput screening of transcription factor targets", Nucleic Acids Research, 33: 17, e150, 9 pages (2005).

Kou, et al. "T-Cell receptor Vbeta repertoire CDR3 length diversity differs within CD45RA and CD45RO T-cell subsets in healthy and human immunodeficiency virus-infected children", Clin Diagn Lab Immunol., 7(6):953-9 (2000).

Krause et al. "Epitope-Specific Human Influenza Antibody Repertoires Diversify by B Cell Intraclonal Sequence Divergence and Interclonal Convergence", The Journal of Immunology, 187: 3704-3711 (2011).

Kyu et al. "Frequencies of human influenza-specific antibody secreting cells or plasmablasts post vaccination from fresh and frozen peripheral blood mononuclear cells", Journal of Immunological Methods, 340: 42-47 (2009).

Landwehr-Kenzel, et al. "Novel GMP-compatible protocol employing an allogeneic B cell bank for clonal expansion of allospecific natural regulatory T cells", Am J Transplant., 14(3):594-606 (2014). doi: 10.1111/ajt.12629. Epub Jan. 27, 2014.

Lazareva-Ulitsky et al, "On the quality of tree-based protein classification," Bioinformatics, 21(9): 1876-1890 (2005).

Leiden, J.M. et al. "The Complete Primary Structure of the T-Cell Receptor Genes From an Alloreactive Cytotoxic Human T-Lymphocyte Clone", Immunogenetics, 24(1): 17-23 (1986).

Li et al, "Mapping short DNA sequencing reads and calling variants using mapping quality scores," Genome Research, 18: 1851-1858 (2008).

Lin, et al. "Multiplex genotype determination at a large number of gene loci", Proc Natl Acad Sci USA, 93(6): 2582-2587 (1996).

Lo, et al. "T cell immunodominance is dictated by the positively selecting self-peptide", Elife, 3:e01457 (2014). doi: 10.7554/eLife. 01457. Epub Jan. 14, 2014.

Maldonado, et al. "Intramuscular therapeutic vaccination targeting HPV16 induces T cell responses that localize in mucosal lesions", Sci Transl Med., 6(221): 221ra13 (2014). doi: 10.1126/scitranslmed. 3007323.

Manion et al., "Reducing Error in Next Generation Sequencing Data with NextGENe Software's Condensation Tool™", Mar. 2009, pp. 1-3. XP055226038.

Mar et al. "Inferring steady state single-cell gene expression distributions from analysis of mesoscopic samples", Genome Biology, 7(12): R119, 12 pages. (2006).

Marrero, et al. "High-throughput sequencing of islet-infiltrating memory CD4+ T cells reveals a similar pattern of TCR Vβ usage in prediabetic and diabetic NOD mice", PLoS One, 8(10):e76546 (2013). doi: 10.1371/journal.pone.0076546. eCollection 2013.

Mary et al. "Analysis of gene expression at the single-cell level using microdroplet-based microfluidic technology", Biomicrofluidics, 5: 024109-1-024109-10 (2011).

Mazor et al. "Antibody internalization studied using a novel IgG binding toxin fusion", Journal of Immunological Methods, 321: 41-59 (2007).

McGoldrick, et al. "Cytomegalovirus-specific T cells are primed early after cord blood transplant but fail to control virus in vivo", Blood, 121(14): 2796-803 (2013). doi: 10.1182/blood-2012-09-453720. Epub Feb. 14, 2013.

Mei et al. "Blood-borne human plasma cells in steady state are derived from mucosal immune responses", Blood, 113(11): 2461-2469 (2009).

Meijer et al. "Isolation of Human Antibody Repertoires with Preservation of the Natural Heavy and Light Chain Pairing", J. Mol. Biol., 358: 764-772 (2006).

Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.

Meier et al. "Simultaneous evaluation of T-cell and B-cell clonality, t(11;14) and t(14;18), in a single reaction by a four-color multiplex polymerase chain reaction assay and automated High-Resolution fragment analysis", American Journal of Pathology, 159(6): 2031-2043 (2001).

Miceli and Parnes. "The roles of CD4 and CD8 in T cell activation", Seminars in Immunology, 3(3): 133-141 (1991). Abstract only.

Michalek, et al. "Identification and monitoring of graft-versus-host specific T-cell clone in stem cell transplantation", The Lancet, 361(9364): 1183-1185 (2003).

Miller, et al., "Assembly algorithms for next-generation sequencing data", Genomics, 95(6): 315-327 (2010).

Mittelstadl, et al. "Thymocyte responsiveness to endogenous glucocorticoids is required for immunological fitness", J Clin Invest., 122(7):2384-94 (2012). doi: 10.1172/JCI63067. Epub Jun. 1, 2012.

Mueller, et al. "Human Treg responses allow sustained recombinant adeno-associated virus-mediated transgene expression", J Clin Invest., 123(12): 5310-8 (2013). doi: 10.1172/JCI70314. Epub Nov. 15, 2013.

Muraro, et al. "T cell repertoire following autologous stem cell transplantation for multiple sclerosis", J Clin Invest., 124(3): 1168-72 (2014). doi: 10.1172/JCI71691.

Neller, et al. "High frequency of herpesvirus-specific clonotypes in the human T cell repertoire can remain stable over decades with minimal turnover", J Virol., 87(1): 697-700 (2013). doi: 10.1128/NI.02180-12. Epub Oct. 17, 2012.

Nie, et al. "Optical detection of single molecules", Annu. Rev. Biophys. Biomol. Struct., 26: 567-596 (1997).

Nucleis product webpage, "Exonuclease I-Shrimp alkaline phosphatase clean up of PCR products," (Published on webpage 2013) Downloaded Dec. 15, 2015.

O'Brian et al., "Sorting out mix-ups. The provenance of tissue sections may be confirmed by PCR using microsatellite markers", Am. J. Clin. Pathol., 106(6): 758-764 (1996). (Abstract Only).

(56) References Cited

OTHER PUBLICATIONS

Pagès, Franck. Tumor-associated immune parameters for personalized patient care. Sci Transl Med., 5(214):214fs42 (2013). doi: 10.1126/scitranslmed.3007942.
Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.
Paszkiewicz et al, "De novo assembly of short sequence reads," Briefings in Bioinformatics, 11(5): 457-472 (2010).
Payne, et al. "Peripheral blood mononuclear cells of patients with breast cancer can be reprogrammed to enhance anti-HER-2/neu reactivity and overcome myeloid-derived suppressor cells", Breast Cancer Res Treat., 142(1):45-57 (2013). doi: 10.1007/s10549-013-2733-5. Epub Oct. 25, 2013.
PCT/US2015/018967, International Search Report and Written Opinion mailed Jul. 30, 2015, 17 pages.
Polz and Cavanaugh. "Bias in Template-to-Product Ratios in Multitemplate PCR", *Applied and Environmental Microbiology*, 64(10): 3724-3730 (1998).
Porter, et al. "Chimeric antigen receptor-modified T cells in chronic lymphoid leukemia", N Engl J Med., 365(8):725-33 (2011). doi: 10.1056/NEJMoa1103849. Epub Aug. 10, 2011.
Prabakaran et al. "454 antibody sequencing—error characterization and correction", *BMC Research Notes*, 4: 404 (2011).
Putnam, et al. "Clinical grade manufacturing of human alloantigen-reactive regulatory T cells for use in transplantation", Am J Transplant., 13(11): 3010-20 (2013). doi: 10.1111/ajt.12433. EpubSep. 18, 2013.
Qu et al. "Efficient frequency-based de novo short-read clustering for error trimming in next-generation sequencing", *Genome Research*, 19: 1309-1315 (2009).
Quick. SOLiD System—a next-gen DNA sequencing platform announced, Gizmag online magazine, http://www.mizmag.com/go/8248, pp. 1-5, Oct. 2007.
Quince et al. "Removing Noise From Pyrosequenced Amplicons", *BMC Informatics*, 12: 38 (2011).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Robert, et al. "CTLA4 blockade broadens the peripheral T-cell receptor repertoire", Clin Cancer Res., 20(9):2424-32 (2014). doi: 10.1158/1078-0432.CCR-13-2648. Epub Feb. 28, 2014.
Robins, et al. "CD4+ and CD8+T cell β antigen receptors have different and predictable V and J gene usage and CDR3 lengths", *J. Immunol.*, 188: 115.10, Abstract (2012).
Robins, et al. "Effects of aging on the human adaptive immune system revealed by high-throughput DNA sequencing of T cell receptors", *J Immunol.*, 188: 47.16, Abstract (2012).
Robins, et al. "High-throughput sequencing of T-cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", *Curr Opin Immunol.*, 25(5): 646-652 (2013). doi: 10.1016/j.coi.2013.09.017. Epub Oct. 16, 2013.
Robins, et al. "Overlap of the human CD8+ T cell receptor repertoire." Oct. 2010. Poster. 1 page.
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Rothberg et al. "The development and impact of 454 sequencing", *Nature Biotechnology*, 26(10): 1117-1124 (2008).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Sartorius Stedim Biotech product brochure, "Primer removal after a PCR reaction with Vivacon® 2", (2010).
Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone. 002731 0.
Sequenta and iRepertoire Join Forces on Blood Cancer Testing. Business Wire. Aug. 8, 2013. http://www.businesswire.com/news/home/20130808005363/en/SequentaiRepertoire-Join-Forces-Blo ... #.VGTT9WdOyUk. 2 pages.
Sfanos et al. "Human Prostate-Infiltrating CD8+T Lymphocytes are Oligoclonal and PD-1+", *The Prostate*, 69(15): 1694-1703 (2009).
Shendure, et al. "Advanced sequencing technologies: methods and goals", *Nat Rev Genet.*, 5(5): 335-344 (2004).
Sherwood, et al. "New Technologies for Measurements of Tumor Infiltrating Lymphocytes", Presented Nov. 7, 2012 Moscone Center, Exhibit Halls ABC.
Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.
Shino, et al. "Usefulness of immune monitoring in lung transplantation using adenosine triphosphate production in activated lymphocytes", *The Journal of Heart and Lung Transplant*, 31: 996-1002 (2012).
Singapore Application No. 11201403212R, Written Opinion mailed Mar. 27, 2015, 12 pges.
Smith et al. "Rapid generation of fully human monoclonal antibodies specific to a vaccinating antigen", *Nature Protocols*, 4(3): 372-384 and CORRIGENDA (2009).
Smith et al. "Quantitative phenotyping via deep barcode sequencing", *Genome Research*, 19: 1836-1842 (2009).
Smith et al, "Using quality scores and longer reads improves accuracy of Solexa read mapping," BMC Bioinformatics, 9: 128 (2008).
Spreafico, et al. "A circulating reservoir of pathogenic-like CD4+ T cells shares a genetic and phenotypic signature with the inflamed synovial micro-environment", Ann Rheum Dis., 0: 1-7 (2014). doi: 10.1136/annrheumdis-2014-206226. [Epub ahead of print].
Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.
Stanley. Essentials of Immunology & Serology, Delmar, Thomson Learning, Chapter 7, T cells, p. 95 (2002).
Stewart and Schwartz. "Immunoglobulin V regions and the B cell", *Blood,* 83(7): 1717-1730 (1994).
Stiller et al. "Direct multiplex sequencing (DMPS)—a novel method for targeted high-throughput sequencing of ancient and highly degraded DNA", *Genome Research,* 19: 1843-849 (2009).
Striebich, et al. "Selective Accumulation of Related CD41 T Cell Clones in the Synovial Fluid of Patients with Rheumatoid Arthritis", *J Immunol.*, 161(8): 4428-36 (1998).
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).

(56) References Cited

OTHER PUBLICATIONS

Taubenheim et al. "High Rate of Antibody Secretion is not Integral to Plasma Cell Differentiation as Revealed by XBP-1 Deficiency", *The Journal of Immunology*, 189: 3328-3338 (2012).
Toriello et al. "Integrated microfluidic bioprocessor for single-cell gene expression analysis", *PNAS*, 105(51): 20173-20178 (2008).
Tsai et al. "Discovery of rare mutations in populations: TILLING by sequencing", Plant Physiology, 156(3): 1257-1268 (and Supplemental Data) (2011).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tumeh et al. "PD-1 blockade induces responses by inhibiting adaptive immune resistance", Nature, 515: 568-571 (2014). doi:10.1038/nature13954.
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 27, 2011 for UK application No. GB1105068.9.
UK Search Report and office action dated Jan. 13, 2012 for UK application No. GB1120209.0.
UK Search Report and office action dated Jul. 7, 2010 for UK application No. GB1009641.0.
Vanderborght, et al. "Dynamic T cell receptor clonotype changes in synovial tissue of patients with early rheumatoid arthritis: effects of treatment with cyclosporin A (Neoral)", *J Rheumatol.*, 29(3): 416-426 (2002).
Wang, et al. "HIV integration site selection: Analysis by massively parallel pyrosequencing reveals association with epigenetic modifications", *Genome Research*, 17(8): 1186-1194 (2007). Epub Jun. 1, 2007.
Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.
Weinstein, J.A. et al. "High-Throughput Sequencing of the Zebrafish Antibody Repertoire", *Science*, 324(5928): 807-810, Supporting/Supplementary Materials (2009).
Weng, et al. "Minimal residual disease monitoring with high-throughput sequencing of T cell receptors in cutaneous T cell lymphoma", Sci Transl Med., 5(214):214ra171 (2013). doi: 10.1126/scitranslmed.3007420.
White et al. "High-throughput microfluidic single-cell RT-qPCR", *PNAS*, 108(34): 13999-14004 (2011).
Wrammert et al. "Rapid cloning of high-affinity human monoclonal antibodies against influenza virus", *Nature*, 453: 667-672 (2008).
Wu, et al. "High-throughput sequencing detects minimal residual disease in acute T lymphoblastic leukemia", Sci Transl Med., 4(134):134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, et al., "Detection of Minimal Residual Disease in B Lymphoblastic Leukemia by High-Throughput Sequencing of IGH", Clin Cancer Res., 20(17): 4540-8 (2014). Published OnlineFirst Jun. 26, 2014; doi: 10.1158-/1078-0432.CCR-13-3231.
Wu et al. "Focused Evolution of HIV-1 Neutralizing Antibodies Revealed by Structures and Deep Sequencing", *Science*, 333: 1593-1602 (2011).
Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
Zehentner et al. "Minimal Disease Detection and Confirmation in Hematologic Malignancies: Combining Cell Sorting with Clonality Profiling", *Clinical Chemistry*, 52(3): 430-437 (2006).
Zhu, et al. "Immune surveillance by CD8αα+ skin-resident T cells in human herpes virus infection", Nature, 497(7450):494-7 and Corrigendum (2013). doi: 10.1038/nature12110. Epub May 8, 2013.
PCT/US2014/061260, Appln filed Oct. 17, 2014, Faham et al.
U.S. Appl. No. 14/383,102, filed Sep. 4, 2014, Faham.
U.S. Appl. No. 14/404,435, filed Nov. 26, 2014, Faham et al.
Bertness, et al. T-cell receptor gene rearrangements as clinical markers of human T-cell lymphomas. N Engl J Med. Aug. 29, 1985;313(9):534-8.
Weiss, et al. Clonal rearrangements of T-cell receptor genes in mycosis fungoides and dermatopathic lymphadenopathy. N Engl J Med. Aug. 29, 1985;313(9):539-44.
Abbott, et al. "Design and use of signature primers to detect carry-over of amplified material", J Virol Methods, 46(1):51-59, Abstract Only (1994).
Akatsuka, Y. et al., "Rapid screening of T-cell receptor (TCR) variable gene usage by multiplex PCR: Application for assessment of clonal composition", *Tissue Antigens*, 53:122-134 (1999).
Alexandre, D. et al. "*H. sapiens* rearranged T-cell receptor gamma chain gene, V2-JP1", GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.
Alexandre, D. et al. "*H. sapiens* rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Al-Lazikani, B. et al., "Standard Conformations for the Canonical Structures of Immunoglobulins," *J. Mol. Biol.*, 273:927-948 (1997).
Altschul, et al. "Basic local alignment search tool", J Mol Biol., 215(3):403-410 (1990).
Andreasson, et al. "The human IgE-encoding transcriptome to assess antibody repertoires and repertoire evolution", *J Mol Biol.*, 362(2):212-227 (2006). Epub Aug. 14, 2006.
Arden, et al. "Human T-cell receptor variable gene segment families", *Immunogenetics*, 42(6):455-500, Abstract Only (1995).
Armand, P. et al., "Detection of circulating tumour DNA in patients with aggressive B-cell non-Hodgkin lymphoma", Brit. J. Haematol., vol. 163, pp. 123-126 (2013).
Aslanzadeh. "Preventing PCR amplification carryover contamination in a clinical laboratory", Ann Clin Lab Sci., 34(4):389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2)640-646 (2000).
Babrzadeh et al. "Development on High-throughput Sequencing Technology: emPCR Titration and Barcode Design", Stanford School of Medicine, 2 pages (2011).
Bahloul, M. et al., "Clinical impact of molecular diagnostics in low-grade lymphoma," Best Practice & Research Clinical Haematology, 18(1):97-111 (2005).
Barbas, et al. "Assembly of combinatorial antibody libraries on phage surfaces: the gene III site", PNAS, 88(18):7978-7982, Abstract Only (1991).
Barker, et al. "A second type II restriction endonuclease from Thermus aquaticus with an unusual sequence specificity", Nucleic Acids Res., 12(14):5567-5581 (1984).
Baum and McCune et al. "Direct measurement of T-cell receptor repertoire diversity with AmpliCot", Nat Methods, 3(11):895-901 (2006).
Benecke. "DNA typing in forensic medicine and in criminal investigations: a current survey", Naturwissenschaften, 84(5):181-188 (1997).
Berger, et al. "The clonotypic T cell receptor is a source of tumor-associated antigens in cutaneous T cell lymphoma", Annals of the New York Academy of Sciences, 941:106-122, Abstract Only (2001).
Bernard et al. "Color multiplexing hybridization probes using the apolipoprotein E locus as a model system for genotyping", *Anal Biochem.*, 273(2):221-228 (1999).

(56) References Cited

OTHER PUBLICATIONS

Bernardin, F. et al., "Estimate of the total No. Of CD8+ clonal expansions in healthy adults using a new DNA heteroduplex-tracking assay for CDR3 repertoire analysis", *Journal of Immunological Methods*, 274(I-2):159-175 (2003).
Berquam-Vrieze, K. et al., "Cell of origin strongly influences genetic selection in a mouse model of T-ALL", *Blood*, 118:4646-4656 (2011).
Berzofsky, et al. "Progress on new vaccine strategies for the immunotherapy and prevention of cancer", J Clin Invest., 113(11):1515-1525 (2004).
Biagi, et al. "Responses to human CD40 ligand/human interleukin-2 autologo cell vaccine in patients with B-cell chronic lymphocytic leukemia", Clin Cancer Res., 11(19 Pt 1):6916-6923 (2005).
Blow, N., "PCR's next frontier," *Nature Methods*, 4(10):869-875 (2007).
Bolotin, D.A. et al., "Next generation sequencing for TCR repertoire profiling: Platform-specific features and correction algorithms", *Eur. J. Immunol.*, 42:3073-3083 (2012).
Bonner et al. "Fluorescence activated cell sorting", *Rev Sci Instrum.*, 43(3):404-409, Abstract Only (1972).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Bousso. "Generation of MHC-peptide tetramers: a new opportunity for dissecting T-cell immune responses", Microbes Infect., 2(4):425-429, Abstract Only (2000).
Bradfield, S.M. et al., "Graft-versus-leukemia effect in acute lymphoblastic leukemia: the importance of tumor burden and early detection," *Leukemia*,18:1156-1158 (2004).
Bravo and Irizarry. "Model-Based Quality Assessment and Base-Calling for Second-Generation Sequencing Data", Biometrics, 66(3): 665-674 (2010).
Brenan, C. et al., "High throughput, nanoliter quantitative PCR," *Drug Discovery Today: Technologies*, 2(3):247-253 (2005).
Brenner, et al. "In vitro cloning of complex mixtures of DNA on microbeads: physical separation of differentially expressed cDNAs", *PNAS*, 97(4):1665-1670 (2000).
Brody, et al. "Active and passive immunotherapy for lymphoma: proving principles and improving results", J Clin Oncol., 29(14):1864-1875, Abstract Only (2011). doi: 10.1200/JCO.2010. 33.4623. Epub Apr. 11, 2011.
Brody, et al., "Immunotransplant for mantle cell lymphoma: Phase I/II study preliminary results", Journal of Clinical Oncology, ASCO Annual Meeting Abstracts Part 1, vol. 29, No. 15, 1 page (2011).
Brody, et al. "Lymphoma immunotherapy: vaccines, adoptive cell transfer and immunotransplant", Immunotherapy, 1(5):809-824 (2009). doi: 10.2217/imt.09.50.
Brown, et al. "Current techniques for single-cell lysis", J. R. Soc. Interface, 5:S131-S138 (2008).
Buck, G.A. et al. "Design Strategies and Performance of Custom DNA Sequencing Primers", *Biotechniques*, 27(3):528-536 (1999).
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Buccisano, et al. "Monitoring of minimal residual disease in acute myeloid leukemia", Curr Opin Oncol., 21(6):582-588, Abstract Only (2009). doi: 10.1097/CCO.0b013e3283311856.
Butkus, B. "Hutch Team Uses ddPCR to Quantify T-Cell Response in Tumors; Adaptive Biotech Eyes Market", *PCR Insider*, Dec. 12, 2013, 3 pages, http://www.genomeweb.com/print/1323296.
Bystrykh. "Generalized DNA Barcode Design Based on Hamming Codes", *PLoS ONE*, 7(5):e36852, 1-8 (2012).
Campana, D., "Progress of Minimal Residual Disease Studies in Childhood Acute Leukemia," Curr Hematol Malig Rep, 5:169-176 (2010).
Campana, et al. "Role of minimal residual disease monitoring in adult and pediatric acute lymphoblastic leukemia", Hematol Oncol Clin North Am., 23(5):1083-1098 (2009). doi: 10.1016/j.hoc.2009. 07.010.
Caporaso, J.G. et al. "Global patterns of 16S rRNA diversity at a depth of millions of sequences per sample", *PNAS*, 108(Suppl. 1):4516-4522 (2010).
Carlotti, et al. "Transformation of follicular lymphoma to diffuse large B-cell lymphoma may occur by divergent evolution from a common progenitor cell or by direct evolution from the follicular lymphoma clone", Blood, 113(15):3553-3557 (2009). doi: 10.1182/blood-2008-08-174839. Epub Feb. 6, 2009.
Carlson, C.S. et al. "Using synthetic templates to design an unbiased multiplex PCR assay", *Nature Communications*, 4:2680, pp. 1-9 (2013).
Casali, et al. "Human monoclonals from antigen-specific selection of B lymphocytes and transformation by EBV", Science, 234(4775):476-479, Abstract Only (1986).
Casbon et al. "A method for counting PCR template molecules with application to next-generation sequencing," *Nucleic Acids Research*, 39(12): e81, 8 pages (2011).
Catherwood, MA. et al., "Improved clonality assessment in germinal centre/post germinal centre non-Hodgkin's lymphomas with high rates of somatic hypermutation", J. Clin. Pathol., 60:524-528, Abstract (2007).
Cavé, H. et al., "Clinical Significance of minimal residual disease in childhood acute lymphoblastic leukemia," *The New England Journal of Medicine*, 339:591-598 (1998).
Chattopadhyay, et al. "A live-cell assay to detect antigen-specific CD4+ T cells with diverse cytokine profiles", Nat Med., 11(10):1113-1117 (2005). Epub Sep. 25, 2005.
Chen, et al. "Microfluidic cell sorter with integrated piezoelectric actuator", Biomed Microdevices, 11(6):1223-1231 (2009). doi: 10.1007/s10544-009-9341-5.
Chen, Y. et al., "T-cell receptor gene expression in tumour-infiltrating lymphocytes and peripheral blood lymphocytes of patients with nasopharyngeal carcinoma", *British Journal of Cancer*, 72(1):117-22 (1995).
Chen, et al. "Total Gene Synthesis: Novel Single-Step and Convergent Strategies Applied to the Construction of a 779 Base Pair Bacteriorhodopsis", Gene. J. Am. Chem Soc., 116:8799-8800, Abstract Only (1994).
Chiu, et al. "Non-invasive prenatal assessment of trisomy 21 by multiplexed maternal plasma DNA sequencing: large scale validity study", BMJ, 342:c7401, 9 pages (2011). doi: 10.1136/bmj.c7401.
Chothia, C. et al. "Canonical structures for the hypervariable regions of immunoglobulins," *J. Mol. Biol.*, 196:901-917, Abstract only (1987).
Chothia, C. et al. "Conformations of immunoglobulin hypervariable regions," *Nature*, 342:877-883 (1989).
Churchill and Waterman. "The Accuracy of DNA Sequences: Estimating Sequence Quality", *Genomics*, 14:89-98 (1992).
Ciudad, J. et al. "Detection of abnormalities in B-cell differentiation pattern is a useful tool to predict relapse in precursor-B-ALL", *British Journal of Haematology*, 104:695-705 (1999).
Cleary, et al. "Production of complex nucleic acid libraries using highly parallel in situ oligonucleotide synthesis", *Nat Methods*, 1(3):241-248 (2004). Epub Nov. 18, 2004.
Coustan-Smith, E. et al., "Clinical importance of minimal residual disease in childhood acute lymphoblastic leukemia," *Blood*, 96(8):2691-2696 (2000).
Coustan-Smith, E. et al., "Early T-cell precursor leukaemia: a subtype of very high-risk acute lymphoblastic leukaemia," *Lancet Oncology*, 10:147-156 (2009).
Coustan-Smith, E. et al., "Prognostic importance of measuring early clearance of leukemic cells by flow cytometry in childhood acute lymphoblastic leukemia", Blood, 100(1):52-58 (2002).
Craig et al. "Identification of genetic variants using bar-coded multiplex sequencing," *Nature Methods*, 5(10): 887-893 (2008) and Supplemental Materials.

(56) References Cited

OTHER PUBLICATIONS

Cronin, et al. "Comprehensive next-generation cancer genome sequencing in the era of targeted therapy and personalized oncology", *Biomark Med.*, 5(3):293-305 (2011). (Abstrat only). doi: 10.2217/bmm.11.37.

Curran-Everett, D., "Multiple comparisons: philosophies and illustrations", *Am J Physiol Regulatory Integrative Comp Physiol.*, 279:R1—R8 (2000).

Dash, P. et al., "Paired analysis of TCR[alpha] and TCR[beta] chains at the single-cell level in mice", *Journal of Clinical Investigation*, 121(1):288-295 (2011).

Davis, et al. "Interrogating the repertoire: broadening the scope of peptide-MHC multimer analysis", *Nat Rev Immunol.*, 11(8):551-558 (2011). doi: 10.1038/nri3020.

De Jonge, H.J.M., et al. "Evidence Based Selection of Housekeeping Genes," *PLoS One*, 9(e989):1-5 (2007).

Deiman, et al. "Characteristics and applications of nucleic acid sequence-based amplification (NASBA)", Mol Biotechnol., 20(2):163-179, Abstract Only (2002).

DeNucci, C.C. et al. "Integrin function in T-cell homing to lymphoid and nonlymphoid sites: getting there and staying there," *Critical Reviews in Immunology*, 29(2):87-109 (2009).

Dheda, K., et al. "Validation of housekeeping genes for normalizing RNA expression in real-time PCR," *Bio Techniques*, 37:112-119 (2004).

Diederichsen, et al. "Prognostic value of the CD4+/CD8+ ratio of tumour infiltrating lymphocytes in colorectal cancer and HLA-DR expression on tumour cells", *Cancer Immunol Immunother.*, 52(7):423-428 (2003). Epub Apr. 15, 2003.

Diehl, et al. "BEAMing: single-molecule PCR on microparticles in water-in-oil emulsions", Nat Methods, 3(7):551-559, Abstract Only (2006).

Dik, W., et al. "New insights on human T cell development by quantitative T cell receptor gene rearrangement studies and gene expression profiling," JEM, 201(11):1715-1723 (2005).

Ding, et al. "Clonal evolution in relapsed acute myeloid leukaemia revealed by whole-genome sequencing", Nature, 481(7382):506-510 (2012). doi: 10.1038/nature10738.

Diviacco, et al. "A novel procedure for quantitative polymerase chain reaction by coamplification of competitive templates", *Gene*, 122(2):313-320 (1992).

Dobosy, J. et al. "RNase H-dependent PCR (rhPCR): improved specificity and single nucleotide polymorphism detection using blocked cleavable primers", *BMC Biotechnology*, 11(80):1-18 (2011).

Dressman, et al. "Transforming single DNA molecules into fluorescent magnetic particles for detection and enumeration of genetic variations", PNAS, 100(15):8817-8822 (2003). Epub Jul. 11, 2003.

Droege, et al. "The Genome Sequencer FLX System—longer reads, more applications, straight forward bioinformatics and more complete data sets", *J Biotechnol.*, 136(1-2):3-10 (2008). doi: 10.1016/j.jbiotec.2008.03.021. Epub Jun. 21, 2008.

Droese, J., et al. "Validation of BIOMED-2 multiplex PCR tubes for detection of TCRB gene rearrangements in T-cell malignancies," *Leukemia*, 18:1531-1538 (2004).

Duby, A.D. et al., "Human T-cell receptor aberrantly rearranged beta-chain J1.5-Dx-J2.1 gene," *PNAS*, GenBank accession No. M13574.1, bases 1 to 100, 4 pages (1986).

Eason et al. "Characterization of synthetic DNA bar codes in *Saccharomyces cerevisiae* genedeletion strains," PNAS, 101(30): 11046-11051 (2004).

Edwards and Gibbs, "Multiplex PCR: advantages, development, and applications," Genome Research, 3:S65-S75 (1994).

Eichler, et al. "Haplotype and interspersion analysis of the FMR1 CGG repeat identifies two different mutational pathways for the origin of the fragile X syndrome", Hum Mol Genet., 5(3):319-330 (1996).

Eichler, et al. "Length of uninterrupted CGG repeats determines instability in the FMR1 gene", Nat Genet., 8(1):88-94, Abstract Only (1994).

Eis, et al. "An invasive cleavage assay for direct quantitation of specific RNAs", Nat Biotechnol., 19(7):673-676, Abstract Only (2001).

Elnifro, E.M., et al. "Multiplex PCR: Optimization and Application in Diagnostic Virology", *Clinical Microbiology Reviews*, 13(4):559-570 (2000).

Emerson, R.O. et al. "High-throughput sequencing of T-cell receptors reveals a homogeneous repertoire of tumour-infiltrating lymphocytes in ovarian cancer", *Journal of Pathology*, 231:433-440 (2013).

EP Application No. 11777704.5, European Search Report dated Jul. 26, 2013, 6 pages.

Faham, M. et al. "Deep-sequencing approach for minimal residual disease detection in acute lymphoblastic leukemia", *Blood*, 120(26):5173-5180 (2012).

Ferrero, et al. "Multiple myeloma shows no intra-disease clustering of immunoglobulin heavy chain genes", Haematologica, 97(6):849-853 (2012). doi: 10.3324/haematol.2011.052852. Epub Dec. 29, 2011.

Flaherty et al. "Ultrasensitive detection of rare mutations using next-generation targeted resequencing", *Nucleic Acids Research*, 40(1): e2, 12 pages (2012).

Flohr, T., et al. "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", *Leukemia*, 22:771-782 (2008).

Frampton, et al. "Development and validation of a clinical cancer genomic profiling test based on massively parallel DNA sequencing", Nat Biotechnol., 31(11):1023-1031 (2013). doi: 10.1038/nbt.2696. Epub Oct. 20, 2013.

Frank. "BARCRAWL and BARTAB: software tools for the design and implementation of barcoded primers for highly multiplexed DNA sequencing," *BMC Bioinformatics*, 10:362 (2009).

Freeman, et al. "Quantitative RT-PCR: Pitfalls and Potential", *Biotechniques*, 6(1):112-125 (1999).

Fu et al. "Counting individual DNA molecules by the stochastic attachment of diverse labels", *PNAS*, 108(22): 9026-9031 and Supporting Materials, 8 pages (2011).

Fuller, et al. "The challenges of sequencing by synthesis", *Nat Biotechnol.*, 7(11):1013-23 (2009) (Abstract only). doi: 10.1038/nbt.1585. Epub Nov. 6, 2009.

Gauss, et al. "Mechanistic constraints on diversity in human V(D)J recombination", Mol Cell Biol., 16(1):258-269 (1996).

Gawad, et al. "Massive evolution of the immunoglobulin heavy chain Ioc in children with B precursor acute lymphoblastic leukemia", Blood, 120(22):4407-4417 (2012). doi: 10.1182/blood-2012-05-429811. Epub Aug. 28, 2012.

Gerlinger, M. et al. "Ultra deep T cell receptor sequencing reveals the complexity and intratumour heterogeneity of T cell clones in renal cell carcinomas", *Journal of Pathology*, 231:424-432 (2013).

Gloor et al. "Microbiome profiling by Illumina sequencing of combinatorial sequence-tagged PCR products," *PLoS ONE*, 5(10): e15406, 15 pages (2010).

Godelaine, et al. "Polyclonal CTL responses observed in melanoma patients vaccinated with dendritic cells pulsed with a MAGE-3.A1 peptide", J Immunol., 171(9):4893-4897 (2003).

Gonzalez, S.F., et al. "Trafficking of B Cell Antigen in Lymph Nodes", *Ann. Rev. Immunol.*, 29:215-233 (2011).

Gottenberg, et al. "Markers of B-lymphocyte activation are elevated in patients with early rheumatoid arthritis and correlated with disease activity in the ESPOIR cohort", Arthritis Res Ther., 11(4):R114 (2009). doi: 10.1186/ar2773. Epub Jul. 23, 2009.

Gratama, et al. "Measuring antigen-specific immune responses", 2008 update. Cytometry A., 73(11):971-974 (2008). doi: 10.1002/cyto.a.20655.

Greenberg, et al. "Profile of immunoglobulin heavy chain variable gene repertoires and highly selective detection of malignant clonotypes in acute lymphoblastic leukemia" J Leukoc Biol., 57(6):856-864 (1995).

Greenman, et al. "Patterns of somatic mutation in human cancer genomes", Nature, 446(7132):153-158 (2007).

(56) References Cited

OTHER PUBLICATIONS

Gribben, JG. "Stem cell transplantation in chronic lymphocytic leukemia", Biol. Blood Marrow Transplant., 15(1 Suppl):53-8 (2009). doi: 10.1016/j.bbmt.2008.10.022.
Gulliksen, et al. "Real-time nucleic acid sequence-based amplification in nanoliter volumes", Anal Chem., 76(1):9-14, Abstract Only (2004).
Gunderson et al. "Decoding Randomly Ordered DNA Arrays", Genome Research, 14:870-877 (2004).
Hadrup, et al. "Parallel detection of antigen-specific T-cell responses by multidimensional encoding of MHC multimers", Nat Methods, 6(7):520-526 (2009) (Abstract Only). doi: 10.1038/nmeth. 1345. Epub Jun. 21, 2009.
Hamady, et al. "Error-correcting barcoded primers for pyrosequencing hundreds of samples in multiplex", Nature Methods, 5(3):235-237 (2008). doi: 10.1038/nmeth.1184. Epub Feb. 10, 2008.
Hanahan, et al. "Hallmarks of cancer: the next generation", Cell, 144(5):646-674 (2011). doi: 10.1016/j.cell.2011.02.013.
Harismendy et al. "Evaluation of next generation sequencing platforms for population targeted sequencing studies", Genome Biology, 10:R32, 13 pages (2009).
Hawkins, et al. "Whole genome amplification—applications and advances", Curr Opin Biotechnol., 13(1):65-67 (2002).
Henegariu, O. et al., "Multiplex PCR: Critical Parameters and Step-By-Step Protocol," Biotechniques, Informa HealthCare, 23(3):504-511 (1997).
Hensel et al. "Simultaneous identification of bacterial virulence genes by negative selection", Science, 269(5222): 400-403 (1995).
Hill, et al. "Using ecological diversity measures with bacterial communities", FEMS Microbiol Ecol., 43(1):1-11 (2003). doi: 10.1111/j.1574-6941.2003.tb01040.x.
Hirohata, et al. "Regulation of human B cell function by sulfasalazine and its metabolites", Int Immunopharmacol., 2(5):631-640, Abstract Only (2002).
Hodges, E. et al. "Diagnostic role of tests for T cell receptor (TCR) genes", J Clin Pathol., 56(1):1-11 (2003).
Holt and Jones. "The new paradigm of flow cell sequencing", Genome Research, 18:839-846 (2008).
Hoogenboom, et al. "Multi-subunit proteins on the surface of filamentophage: methodologies for displaying antibody (Fab) heavy and light chains", Nucleic Acids Res., 19(15):4133-4137 (1991).
Hoogendoorn, et al. "Primary allogeneic T-cell responses against mantle cell lymphoma antigen-presenting cells for adoptive immunotherapy after stem cell transplantation", Clin Cancer Res., 11(14):5310-5318 (2005).
Hoos, et al. "Improved endpoints for cancer immunotherapy trials", J Natl Cancer Inst., 102(18):1388-1397 (2010). doi: 10.1093/jnci/djq310. Epub Sep. 8, 2010.
Hoover and Lubkowski. "DNAWorks: an automated method for designing oligonucleotides for PCR-based gene synthesis", Nucleic Acids Res., 30(10):e43, 7 pages (2002).
Hoven, et al. "Detection and isolation of antigen-specific B cells by the fluorescence activated cell sorter (FACS)", J Immunol Methods, 117(2):275-284, Abstract Only, 2 pages (1989).
Huang, et al. "Isolation of cell-free DNA from maternal plasma using manual and automated systems", Methods Mol Biol., 444:203-208, Abstract Only (2008). doi: 10.1007/978-1-59745-066-9_15.
Huh, et al. "Microfluidics for flow cytometric analysis of cells and particles", Physiol Meas., 26(3):R73-98, Abstract Only (2005). Epub Feb. 1, 2005.
Huse, et al. "Generation of a large combinatorial library of the immunoglobulin repertoire in phage lambda", Science, 246(4935):1275-1281, Abstract Only (1989).
Hwang, H.Y. et al. "Identification of a Commonly used CDR3 Region of Infiltrating T Cells Expressing Vβ13 and Vβ15 Derived from Psoriasis Patients", The Journal of Investigative Dermatology, 120(3):359-364 (2003).
Iancu, et al. "Profile of a serial killer: cellular and molecular approaches to study individual cytotoxic T-cells following therapeutic vaccination", J Biomed Biotechnol., 2011:452606 (2011). doi: 10.1155/2011/452606. Epub Nov. 14, 2010.
Illumina. Genome analyzer pipeline software version 1.0 user guide. Part #1004759, 176 pages (2008).
Illumina. TruSeq Sample Preparation Kit and Data Sheet. Illumina, Inc., San Diego, CA, 4 pages (2011).
Jaffe, et al. "Classification of lymphoid neoplasms: the microscope as a tool for disease discovery", Blood, 112(12):4384-4399 (2008). doi: 10.1182/blood-2008-07-077982.
Jung, et al. "Unraveling V(D)J recombination; insights into gene regulation", Cell, 116(2):299-311 (2004).
Kalinina, O. et al. "Nanoliter scale PCR with TaqMan detection", Nucleic Acids Research, 25(10):1999-2004 (1997).
Kalos, M. et al. "T Cells with Chimeric Antigen Receptors Have Potent Antitumor Effects and Can Establish Memory in Patients with Advanced Leukemia", Science Translational Medicine, 3(95ra73):1-11 (2011).
Kaplinski and Remm. "MultiPLX Automatic Grouping and Evaluation of PCR Primers", Methods in Molecular Biology, 402(PCR Primer Design):287-303 (2004).
Katz, S.C. et al. "T Cell Infiltrate Predicts Long-Term Survival Following Resection of Colorectal Cancer Liver Metastases," Ann. Surg. Oncol., 16:2524-2530 (2009).
Kehrl, J.H. et al. "Chemoattractant Receptor Signaling and Its Role in Lymphocyte Motility and Trafficking", Current Topics in Microbiology and Immunology, 334:107-127 (2009).
Kiianitsa, et al., "Development of Tools for T-Cell Repertoire Analysis (TCRB Spectratyping) for the Canine Model of Hematopoietic Cell Transplantation", Blood, ASH—Annual Meeting Abstracts, 110:Abstract 4873, 2 pages (2007).
Kinde et al. "Detection and quantification of rare mutations with massively parallel sequencing," PNAS, 108(23): 9530-9535 and Supporting Information, 16 pages (2011).
Kircher, et al. "Improved base calling for the Illumina Genome Analyzer using machine learning strategies", Genome Biol., 10(8):R83, 9 pages (2009). doi: 10.1186/gb-2009-10-8-r83. Epub Aug. 14, 2009.
Kivioja et al. "Counting absolute numbers of molecules using unique molecular identifiers," Nature Methods, 9(1): 72-76 (2012).
Klarenbeek, P.L. et al. "Human T-cell memory consists mainly of unexpanded clones", Immunology Letters, 133:42-48 (2010).
Klebanoff, et al. "Therapeutic cancer vaccines: are we there yet?", Immunol Rev., 239(1):27-44 (2011). doi: 10.1111/j.1600-065X.2010.00979.x.
Klenerman, et al. "Tracking T cells with tetramers: new tales from new tools", Nat Rev Immunol., 2(4):263-272 (2002).
Kneba, et al. "Characterization of clone-specific rearrangement T-cell receptor gamma-chain genes in lymphomas and leukemias by the polymerase chain reaction and DNA sequencing", Blood, 84(2):574-581 (1994).
Kohlmann, et al. "Integration of next-generation sequencing into clinical practice: are we there yet?", Semin Oncol., 39(1):26-36, Abstract Only (2012). doi: 10.1053/j.seminoncol.2011.11.008.
Krueger, et al. "Large scale loss of data in low-diversity illumina sequencing libraries can be recovered by deferred cluster calling", PLoS One, 6(1):e16607, 7 pages (2011). doi: 10.1371/journal.pone.0016607.
Ku, et al. "Exome sequencing: dual role as a discovery and diagnostic tool", Ann Neurol., 71(1):5-14, Abstract Only (2012). doi: 10.1002/ana.22647.
Kumar, et al. "PEG-labeled nucleotides and nanopore detection for single molecule DNA sequencing by synthesis", Sci Rep., 2:684, 8 pages (2012). Epub Sep. 21, 2012.
Kwak, et al. "Induction of immune responses in patients with B-cell lymphoma against the surface-immunoglobulin idiotype expressed by their tumors", N Engl J Med., 327(17):1209-1215 (1992).
Ladányi, A., et al. "Prognostic impact of B-cell density in cutaneous melanoma", Cancer Immunol. Immunother, 60(12):1729-1738 (2011).
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lym-

(56) References Cited

OTHER PUBLICATIONS phoma (MCL) and multiple myeloma (MM)", Blood, vol. 120, No. 21, Abstract 788 (Conference Abstract), Entire Abstract (2012).
Ladetto, M. et al. "Real-time polymerase chain reaction in multiple myeloma: Quantitative analysis of tumor contamination of stem cell harvests", Experimental Hematology, 30:529-536 (2002).
Ladetto, M. et al. "Real-Time Polymerase Chain Reaction of Immunoglobulin Rearrangements for Quantitative Evaluation of Minimal Residual Disease in Multiple Myeloma", American Society for Blood and Marrow Transplantation, 6(3):241-253 (2000).
Larimore, K., et al. "Shaping of Human Germline IgH Repertoires Revealed by Deep Sequencing", The Journal of Immunology, 189(6):3221-3230 (2012).
Lee, et al. "Characterization of circulating T cells specific for tumor-associated antigens in melanoma patients", Nat Med., 5(6):677-685, Abstract Only (1999).
Lefranc. "IMGT, the international ImMunoGeneTics database", Nucleic Acids Res., 31(1):307-310 (2003).
Lennon, et al. "A scalable, fully automated process for construction of sequence-ready barcoded libraries for 454", Genome Biol., 11(2):R15, 9 pages (2010). doi: 10.1186/gb-2010-11-2-r15. Epub Feb. 5, 2010.
Leary, et al. "Development of personalized tumor biomarkers ing massively parallel sequencing", Sci Transl Med., 2(20):20ra14 (2010). doi: 10.1126/scitranslmed.3000702.
Leproust, et al. "Synthesis of high-quality libraries of long (150mer) oligonucleotides by a novel depurination controlled process", Nucleic Acids Res., 38(8):2522-2540 (2010). doi: 10.1093/nar/gkq163. Epub Mar. 22, 2010.
Lessin, et al. "Molecular diagnosis of cutaneous T-cell lymphoma: polymerase chain reaction amplification of T-cell antigen receptor beta-chain gene rearrangements", J Invest Dermatol., 96(3):299-302 (1991).
Li, et al. "β cell-specific CD4+ T cell clonotypes in peripheral blood and the pancreatic islets are distinct", J Immunol. , 183(11):7585-7591 (2009). doi: 10.4049/jimmunol.0901587. Epub Nov. 16, 2009.
Logan, et al., "High-throughput immunoglobulin gene sequencing quantifies minimal residual disease in CLL with 10e-6 sensitivity and strongly predicts relapse after allogeneic hematopoietic cell transplantation", Blood, vol. 118 (21), Abstract 2542 (2011).
Logan, et al., "Massively parallel immunoglobulin gene sequencing provides ultra-sensitive minimal residual disease detection and predicts post-transplant relapse in acute lymphoblastic leukemia by three to six months", Blood, vol. 118 (21), Abstract 4104 (2011).
Lossos, et al. "Transformation of follicular lymphoma to diffuse large-cell lymphoma: alternative patterns with increased or decreased expression of c-myc and its regulated genes", PNAS, 99(13):8886-8891 (2002). Epub Jun. 19, 2002.
Lowe, T., et al., "A computer program for selection of oligonucleotide primers for polymerase chain reactions," Nucleic Acids Research, 18(7):1757-1761 (1990).
Lowman, et al. "Monovalent phage display: a method for selecting variant proteins from random libraries", Methods: A Companion to Methods in Enzymology, 3:205-216, Abstract Only (1991).
Lúdo, P. et al. "Flow cytometric analysis of normal B cell differentiation: a frame of reference for the detection of minimal residual disease in precursor-B-ALL", Leukemia, 13:419-427 (1999).
Lyamichev, et al. "Polymorphism identification and quantitative detection of genomic DNA by invasive cleavage of oligonucleotide probes", Nat Biotechnol., 17(3):292-396 (1999).
Mackay, et al. "Real-time PCR in virology", Nucleic Acids Res., 30(6):1292-305 (2002).
Mahmoud, S.M.A. et al. "Tumor-Infiltrating CDS+ Lymphocytes Predict Clinical Outcome in Breast Cancer", Journal of Clinical Oncology, 29(15):1949-1955 (2011).
Malyguine, et al. "ELISPOT Assay for Monitoring Cytotoxic T Lymphocytes (CTL) Activity in Cancer Vaccine Clinical Trials", Cells, 1(2):111-126 (2012). doi: 10.3390/cells1020111.

Manrao, et al. "Reading DNA at single-nucleotide resolution with a mutant MspA nanopore and phi29 DNA polymerase", Nat Biotechnol. , 30(4):349-353 (2012). doi: 10.1038/nbt.2171.
Marelli-Berg, F.M., et al. "Memory T-cell trafficking: new directions for busy commuters", Immunology, 130:158-165 (2010).
Mardis. "Next-generation DNA sequencing methods", Annu. Rev. Genomics Hum. Genet., 9:387-402 (2008). doi: 10.1146/annurev.genom.9.081307.164359.
Mariani, S. et al., "Comprehensive assessment of the TCRBV repertoire in small T-cell samples by means of an improved and convenient multiplex PCR method," Experimental Hematology, 37(6):728-738 (2009).
Markoulatos, P. et al., "Multiplex Polymerase Chain Reaction: A Practical Approach", Journal of Clinical Laboratory Analysis, 16:47-51 (2002).
Martin-Jimenez, et al. "Molecular characterization of heavy chain immunoglobulin gene rearrangements in Waldenström's macroglobulinemia and IgM monoclonal gammopathy of undetermined significance", Haematologica, 92(5):635-642 (2007).
Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).
Maślanka, K. et al., "Molecular Analysis of T-Cell Repertoires: Spectratypes Generated by Multiplex Polymerase Chain Reaction and Evaluated by Radioactivity or Fluorescence", Human Technology, 44(1):28-34 (1995).
Matsubara, et al. "Microchamber array based DNA quantification and specific sequence detection from a single copy via PCR in nanoliter volumes", Biosens Bioelectron, 20(8):1482-1490, Abstract Only (2005).
Mazumder, et al., "Detection of multiple myeloma cells in peripheral blood using high-throughput sequencing assay" Blood, vol. 120, No. 21, Abstract 321 (Conference Abstract), Entire Abstract (2012).
McCloskey et al. "Encoding PCR products with batch-stamps and barcodes," Biochem. Genet., 45: 761-767 (2007).
Meier, et al. "The influence of different stimulation conditions on the assessment of antigen-induced CD154 expression on CD4+ T cells", Cytometry A., (11):1035-1042 (2008). doi: 10.1002/cyto.a.20640.
Merriam-Webster, 2 pages, (definition of "e.g.," accessed Apr. 25, 2014).
Merriam-Webster, 4 pages (definition of "substantial," accessed Apr. 25, 2014).
Metzker, "Sequencing Technologies—The Next Generation", Nature Reviews, Genetics, 11:31-46 (2010).
Meyer et al. "Targeted high-throughput sequencing of tagged nucleic acid samples," Nucleic Acids Research, 35(15): e97, 5 pages (2007).
Miltenyi, et al. "High gradient magnetic cell separation with MACS", Cytometry, 11(2):231-238 (1990).
Miner et al. "Molecular barcodes detect redundancy and contamination in hairpin-bisulfite PCR", Nucleic Acids Research, 32(17): e135, 4 pages (2004).
Miqueu, P. et al. "Statistical analysis of CDR3 length distributions for the assessment of T and B cell repertoire biases", Molecular Immunology, 44:1057-1064 (2007).
Mitra, et al. "Fluorescent in situ sequencing on polymerase colonies", Anal Biochem., 320(1):55-65, Abstract Only (2003).
Miyashita, et al. "N-Methyl substituted 2',4'-BNANC: a highly nuclease-resistant nucleic acid analogue with high-affinity RNA selective hybridization", Chem Commun (Camb), (36):3765-3767, Abstract Only (2007). Epub Jul. 9, 2007.
Moen, et al. "Immunoglobulin G and A antibody responses to Bacteroides forsyth and Prevotella intermedia in sera and synovial fluids of arthritis patients", Clin Diagn Lab Immunol., 10(6):1043-1050 (2003).
Molloy, et al. "Soluble T cell receptors: novel immunotherapies", Curr Opin Pharmacol., 5(4):438-443 (2005) (Abstract Only).

(56) References Cited

OTHER PUBLICATIONS

Monod, M.Y. et al. "IMGT/JunctionAnalysis: the first tool for the analysis of the immunogloblulin and T cell receptor complex V-J and V-D-J JUNCTIONs", *Bioinformatics*, 20(Suppl 1):i379-385 (2004).
Morgan, et al. "Cancer regression in patients after transfer of genetically engineered lymphocytes", *Science*, 314(5796):126-129 (2006). Epub Aug. 31, 2006.
Morozova et al. "Applications of New Sequencing Technologies for Transcriptome Analysis", *Annu. Rev. Genomics Hum. Genet.*, 10:135-151 (2009).
Morrissy et al. "Next-generation tag sequencing for cancer gene expression profiling", *Genome Research*, 19:1825-1835 (2009).
Moura, et al. "Alterations on peripheral blood B-cell subpopulations in very early arthritis patients", Rheumatology (Oxford), 49(6):1082-1092 (2010). doi: 10.1093/rheumatology/keq029. Epub Mar. 7, 2010.
Murugan, et al. "Statistical inference of the generation probability of T-cell receptors from sequence repertoires", PNAS, 109(40):16161-16166 (2012). doi: 10.1073/pnas.1212755109. Epub Sep. 17, 2012.
Nakano, et al. "Single-molecule PCR using water-in-oil emulsion", J Biotechnol., 102(2):117-124, Abstract Only (2003).
Navarrete, et al. "Upfront immunization with autologous recombinant idiotype Fab fragment without prior cytoreduction in indolent B-cell lymphoma", Blood, 117(5):1483-1491 (2011). doi: 10.1182/blood-2010-06-292342. Epub Nov. 2, 2010.
Needleman and Wunsch. "A general method applicable to the search for similarities in the amino acid sequence of two proteins", *J Mol Biol.*, 48(3):443-453 (1970).
Newman, et al. "Identification of an antigen-specific B cell population", *J Immunol Methods*, 272(1-2):177-187, Abstract Only (2003).
Nicot, N. et al. "Housekeeping gene selection for real-time RT-PCR normalization in potato during biotic and abiotic stress", *Journal of Experimental Botany*, 56(421):2907-2914 (2005).
Nielsen, et al. "Peptide nucleic acid (PNA). A DNA mimic with a pseudopeptide backbone", Chem. Soc. Rev., 26:73-78, Abstract Only (1997).
Nolan, T. et al. "Quantification of mRNA using real-time RT-PCR", *Nature Protocols*, 1(3):1559-1582 (2006).
Oelke, et al. "Ex vivo induction and expansion of antigen-specific cytotoxic T cells by HLA-Ig-coated artificial antigen-presenting cells", Nat Med., 9(5):619-624 (2003). Epub Apr. 21, 2003.
Okello et al. "Comparison of methods in the recovery of nucleic acids from archival formalin-fixed paraffin-embedded autopsy tissues", *Anal Biochem.*, 400(1):110-117 (2010). doi: 10.1016/j.ab.2010.01.014. Epub Jan. 15, 2010.
Ottensmeier, et al. "Analysis of $V_H$ genes in follicular and diffuse lymphoma shows ongoing somatic mutation and multiple isotype transcripts in early disease with changes during disease progression", Blood, 91(11):4292-4299 (1998).
Palmowski, et al. "The use of HLA class I tetramers to design a vaccination strategy for melanoma patients", *Immunol Rev.*, 188:155-163 (2002) (Abstract Only).
Palomaki, et al. "DNA sequencing of maternal plasma reliably identifies trisomy 18 and trisomy 13 as well as Down syndrome: an international collaborative study", *Genet Med.*, 14(3):296-305 (2012). doi: 10.1038/gim.2011.73. Epub Feb. 2, 2012.
Parameswaran et al. "A pyrosequencing-tailored nucleotide barcode design unveils opportunities for large-scale sample multiplexing", *Nucleic Acids Research*, 35(19): e130, 9 pages (2007).
Parmigiani, et al. "Design and analysis issues in genome-wide somatic mutation studies of cancer", Genomics, 93(1):17-21 (2009). doi: 10.1016/j.ygeno.2008.07.005. Epub Aug. 23, 2008.
Peet. "The Measurement of Species Diversity", Annual Review of Ecology and Systematics, 5:285-307, Abstract Only (1974).
Petrosino, et al. "Metagenomic pyrosequencing and microbial identification", Clin Chem., 55(5):856-866 (2009). doi: 10.1373/clinchem.2008.107565. Epub Mar. 5, 2009.
PCT/US2009/006053, Written Opinion dated Jun. 15, 2010, 4 pages.
PCT/US2009/006053, International Preliminary Report on Patentability dated May 10, 2011, 5 pages.
PCT/US2010/021264, International Search Report and Written Opinion mailed Apr. 14, 2010, 7 pages.
PCT/US2010/021264, International Preliminary Report on Patentability mailed Jul. 19, 2011, 5 pages.
PCT/US2010/037477, PCT International Search Report and Written Opinion mailed Sep. 24, 2010, 10 pages.
PCT/US2010/037477, International Preliminary Report on Patentability dated Jan. 4, 2012, 7 pages.
PCT/US2011/000791, International Preliminary Report on Patentability dated Nov. 6, 2012, 10 pages.
PCT/US2011/000792, International Preliminary Report on Patentability dated Nov. 6, 2012, 8 pages.
PCT/US2011/026373, International Search Report and Written Opinion mailed Oct. 20, 2011, 17 pages.
PCT/US2011/026373, International Preliminary Report on Patentability dated Aug. 28, 2012, 11 pages.
PCT/US2011/049012, International Search Report and Written Opinion mailed Apr. 10, 2012, 9 pages.
PCT/US2011/049012, International Preliminary Report on Patentability dated Feb. 26, 2013, 5 pages.
PCT/US2012/053530, International Search Report and Written Opinion dated Feb. 26, 2013, 13 pages.
PCT/US2012/053530, International Preliminary Report on Patentability dated Fmarch 12, 2014, 7 pages.
PCT/US2012/058989, International Search Report and Written Opinion dated Mar. 29, 2013, 12 pages.
PCT/US2012/058989, International Preliminary Report on Patentability dated Apr. 15, 2014, 8 pages.
PCT/US2012/061193, International Search Report and Written Opinion mailed Mar. 28, 2013, 13 pages.
PCT/US2012/061193, International Preliminary Report on Patentability dated Apr. 22, 2014, 8 pages.
PCT/US2012/061977, International Search Report and Written Opinion dated Feb. 25, 2013, 11 pages.
PCT/US2012/061977, International Preliminary Report on Patentability dated May 6, 2014, 7 pages.
PCT/US2012/067656, International Search Report and Written Opinion dated Mar. 13, 2013, 6 pages.
PCT/US2012/067656, International Preliminary Report on Patentability dated Jun. 10, 2014, 4 pages.
PCT/US2012/068617, International Search Report and Written Opinion mailed Mar. 28, 2013, 10 pages.
PCT/US2012/068617, International Preliminary Report on Patentability mailed Jun. 10, 2014, 6 pages.
PCT/US2012/068631, International Search Report and Written Opinion dated Feb. 26, 2013, 8 pages.
PCT/US2012/068631, International Preliminary Report on Patentability dated Jun. 10, 2014, 7 pages.
PCT/US2012/069187, International Search Report and Written Opinion dated Feb. 22, 2013, 8 pages.
PCT/US2012/069187, International Preliminary Report on Patentability dated May 5, 2015, 6 pages.
PCT/US2012/069310, International Preliminary Report on Patentability dated Jun. 17, 2014, 6 pages.
PCT/US2012/070674, International Search Report and Written Opinion dated Feb. 22, 2013, 8 pages.
PCT/US2012/070674, International Preliminary Report on Patentability dated Aug. 5, 2014, 6 pages.
PCT/US2013/028942, International Search Report and Written Opinion dated May 9, 2013, 10 pages.
PCT/US2013/028942, International Preliminary Report on Patentability dated May 5, 2015, 9 pages.
PCT/US2013/029181, International Search Report and Written Opinion dated May 31, 2013, 6 pages.
PCT/US2013/029181, International Preliminary Report on Patentability dated Sep. 9, 2014, 5 pages.
PCT/US2013/035857, International Search Report and Written Opinion dated Aug. 7, 2013, 10 pages.

(56) References Cited

OTHER PUBLICATIONS

PCT/US2013/035857, International Preliminary Report on Patentability dated Oct. 14, 2014, 8 pages.
PCT/US2013/040221, International Search Report and Written Opinion mailed Sep. 23, 2013, 15 pages.
PCT/US2013/040221, International Preliminary Report on Patentability dated Apr. 24, 2014, 41 pages.
PCT/US2013/045276, International Search Report and Written Opinion dated Jan. 29, 2014, 11 pages.
PCT/US2013/045276, International Preliminary Report on Patentability dated Dec. 16, 2014, 2014, 7 pages.
PCT/US2013/045994, International Search Report and Written Opinion mailed Oct. 25, 2013, 15 pages.
PCT/US2013/045994, International Preliminary Report on Patentability dated Dec. 16, 2014, 10 pages.
PCT/US2013/051539, International Search Report and Written Opinion dated Nov. 27, 2013, 9 pages.
PCT/US2013/051539, International Preliminary Report on Patentability dated Jan. 27, 2015, 7 pages.
PCT/US2013/062925, International Search Report and Written Opinion mailed Nov. 25, 2013, 11 pages.
PCT/US2013/062925, Second Written Opinion mailed Jan. 23, 2015, 7 pages.
PCT/US2013/062925, International Preliminary Report on Patentability mailed Apr. 16, 2015, 30 pages.
PCT/US2013/065493, International Search Report and Written Opinion dated Jan. 20, 2014, 14 pages.
PCT/US2013/065493, International Preliminary Report on Patentability dated Apr. 21, 2015, 10 pages.
PCT/US2013/065757, International Search Report and Written Opinion dated Jan. 21, 2014, 10 pages.
PCT/US2013/065757, International Preliminary Report on Patentability dated Apr. 28, 2015, 6 pages.
PCT/US2014/017416, International Search Report dated May 12, 2014, 9 pages.
PCT/US2014/030859, International Search Report and Written Opinion mailed Jul. 18, 2014, 7 pages.
PCT/US2014/047909, International Search Report dated Nov. 17, 2014.
Pekin, D. et al. "Quantitative and sensitive detection of rare mutations using droplet-based microfluidics", Lab Chip, 11(3):2156 (2011).
Perkel, J. "Overcoming the Challenges of Multiplex PCR", Biocompare Editorial Article, Oct. 23, 2012, 6 pages, can be retrieved at URL:http://www.biocompare.com/Editorial-Articles/117895-Multiplex-PCR/>.
Pohl, G. and Shih. "Principle and applications of digital PCR", Expert Rev. Mol. Diagn., 4(1):41-47 (2004).
Polstra, et al. "Development of real-time NASBA assays with molecular beacon detection to quantify mRNA coding for HHV-8 lytic and latent genes", BMC Infect Dis., 2:18 (2002). Epub Sep. 4, 2002.
Pourmand, et al. "Direct electrical detection of DNA synthesis", PNAS, 103(17):6466-6470 (2006). Epub Apr. 13, 2006.
Puisieux, I. et al., "Oligoclonality of Tumor-Infiltrating Lymphocytes from Human Melanomas," The Journal of Immunology, 153:2807-2818 (1994).
Qui et al. "DNA sequence-based "bar codes" for tracking the origins of expressed sequence tags from a maize cDNA library constructed using multiple mRNA sources," Plant Physiology, 133(2): 475-481 (2003).
Ramsden, et al. "V(D)J recombination: Born to be wild", Semin Cancer Biol., 20(4):254-260 (2010). doi: 10.1016/j.semcancer.2010.06.002. Epub Jul. 1, 2010.
Rasmussen, T. et al. "Quantitation of minimal residual disease in multiple myeloma using an allele-specific real-time PCR assay", Experimental Hematology, 28:1039-1045 (2000).

Reddy, et al. "Monoclonal antibodies isolated without screening by analyzing the variable-gene repertoire of plasma cells", Nat Biotechnol., 28(9):965-969 (2010) (Abstract Only). doi: 10.1038/nbt.1673. Epub Aug. 29, 2010.
Reischl and Kochanowski. "Quantitative PCR A Survey of the Present Technology", Molecular Biotechnology, 3:55-71 (1995).
Robins et al. "Detecting and monitoring lymphoma with high-throughput sequencing" Oncotarget, 2:287-288 (2011).
Robins, H. et al. "The Computational Detection of Functional Nucleotide Sequence Motifs in the Coding Regions of Organisms", Exp Bioi Med, 233(6):665-73 (2008).
Robins, H. et al. "Overlap and Effective Size of the Human CD8+ T Cell Receptor Repertoire", Science Transitional Medicine, 2(47, 47ra64):17 pages, Supplemental Materials (2010).
Robins, H., et al. "Ultra-sensitive detection of rare T cell clones", Journal of Immunological Methods, 375:14-19 (2012).
Robins, H. et al. "Digital Genomic Quantification of Tumor Infiltrating Lymphocytes", Science Translational Medicine, 5:214ra169, 19 pages, Supplementary Materials (2013).
Rock, E.P. et al. "CDR3 Length in Antigen-specific Immune Receptors", J. Exp. Med., 179:323-328 (1994).
Ronaghi, et al. "A sequencing method based on real-time pyrophosphate", Science, 281(5375):363, 365, 5 pages (1998).
Rosenberg, S.A. et al. "New Approach to the Adoptive Immunotherapy of Cancer with Tumor-Infiltrating Lymphocytes", Science, 233(4770):1318-1321 (1986).
Roshal, M. et al. "Immaturity Associated Antigens Are Lost During Induction for T Cell Lymphoblastic Leukemia: Implications for Minimal Residual Disease Detection", Cytometry Part B (Clinical Cytometry), 78:139-146 (2010).
Rothberg, et al. "An integrated semiconductor device enabling non-optical genome sequencing", Nature, 475(7356):348-352 (2011). doi: 10.1038/nature10242.
Rozen, S. et al. "Primer3 on the WWW for General Users and for Biologist Programmers", Methods in Molecular Biology, Bioinformatics Methods and Protocols, 132:365-386 (2000).
Saada, R. et al. "Models for antigen receptor gene rearrangement: CDR3 length", Immunology and Cell Biology, 85:323-332 (2007).
Salzberg. "Mind the gaps," Nature Methods, 7(2): 105-106 (2010).
Santalucia, Jr., J. "Physical Principles and Visual-OMP Software for Optimal PCR Design," Methods in Molecular Biology, 402(PCR Primer Design):3-33, 40 pages (2007).
Santamaria, P. et al. "Beta-Cell-Cytotoxic CDS T Cells from Nonobese Diabetic Mice Use Highly Homologous T Cell Receptor a-Chain CDR3 Sequences", The Journal of Immunology, 154(5):2494-2503 (1995).
Schlissel, M.S. et al. "Leukemia and lymphoma: a cost of doing business for adaptive immunity", Genes Dev., 20(12):1539-44 (2006).
Schmitt et al. "Detection of ultra-rare mutations by next-generation sequencing," PNAS, 109(36): 14508-14513 and Supporting Information, 9 pages (2012).
Schrappe, M. et al. "Late MRD response determines relapse risk overall and in subsets of childhood T-cell ALL: results of the AIEOP-BFM-ALL 2000 study", Blood, 118(8):2077-2084 (2011).
Sebastian, E. et al., "Molecular Characterization of immunoglobulin gene rearrangements in diffuse large B-cell lymphoma", Am. J. Pathol., 181:1879-1888, Abstract (2012). (Epub: Sep. 28, 2012).
Seitz, et al. "Reconstitution of paired T cell receptor α- and β-chains from microdissected single cells of human inflammatory tissues", PNAS, 103:12057-12062 (2006).
Seo, et al. "Four-color DNA sequencing by synthesis on a chip using photocleavable fluorescent nucleotides", PNAS, 102(17):5926-5931 (2005). Epub Apr. 13, 2005.
SG Application No. 11201403212R, Written Opinion mailed Mar. 27, 2015, 12 pages.
Shendure, et al. "Accurate multiplex polony sequencing of an evolved bacterial genome", Science, 309(5741):1728-1732, Abstract Only (2005). Epub Aug. 4, 2005.
Shendure and Ji. "Next-generation DNA sequencing", Nature Biotechnology, 26(10):1135-1145 (2008).

(56) References Cited

OTHER PUBLICATIONS

Sherwood, A. et al. "Deep Sequencing of the Human TCRγ and TCRβ Repertoires Suggests that TCR β Rearranges After αβ and γδ T Cell Commitment", Science Translational Medicine, 3(90):1-7 (2011).
Shiroguchi et al. "Digital RNA sequencing minimizes sequence-dependent bias and amplification noise with optimized single-molecule barcodes," PNAS, 109(4):1347-1352 (2012).
Shoemaker et al. "Quantitative phenotypic analysis of yeast deletion mutants using a highly parallel molecular bar-coding strategy," Nature Genetics, 14(4): 450-456 (1996).
Shumaker, et al. "Mutation detection by solid phase primer extension", Hum Mutat., 7(4):346-354, Abstract Only (1996).
Sia, et al. "Microfluidic devices fabricated in poly(dimethylsiloxane) for biological studies", Electrophoresis, 24(21):3563-3576, Abstract Only (2003).
Silver, N. et al. "Selection of housekeeping genes for gene expression studies in human reticulocytes using real-time PCR", BMC Molecular Biology, 7(33):1-9 (2006).
Sims, et al. "Fluorogenic DNA sequencing in PDMS microreactors", Nat Methods, 8(7):575-580 (2011). doi: 10.1038/nmeth.1629.
Sims, et al. "MHC-peptide tetramers for the analysis of antigen-specific T cells", Expert Rev Vaccines, 9(7):765-774 (2010). doi: 10.1586/erv.10.66.
Sint, D., et al. "Advances in multiplex PCR: balancing primer efficiencies and improving detection success", Methods in Ecology and Evolution, 3(5):898-905 (2012).
Slightom, J.L. et al. "Homo sapiens germline beta T-cell receptor locus", NCBI Accession No. L36092 NCBI, 254 pages (2009) Retrieved from the Internet: <URL:http://www.ncbi.nlm.nih.gov/nuccore/L36092>.
Smith, et al. "Comparison of biosequences", Advances in Applied Mathematics, 2:482-489 (1981).
Sobrino, et al. "SNPs in forensic genetics: a review on SNP typing methodologies", Forensic Sci Int., 154(2-3):181-194, Abstract Only (2005). Epub Jan. 11, 2005.
Standard Sequencing Primers, Max Planck Genome Center Cologne, Jan. 15, 2011, downloaded from https://genomecentre.mpipz.mpg.de/SeqOrderDB/export/sequencing-primers.html.
Steenbergen, et al. "Frequent ongoing T-cell receptor rearrangements in childhood B-precursor acute lymphoblastic leukemia: implications for monitoring minimal residual disease", Blood, 86(2):692-702, Abstract Only (1995).
Stein and Nombela-Arrieta. "Chemokine control of lymphocyte trafficking: a general overview", Immunology, 116(10):1-12 (2005).
Steinmetz, O.M. et al. "Chemokines and B cells in renal inflammation and allograft rejection", Frontiers in Bioscience (Schol. Ed.), 1:13-22 (2009).
Stemmer, et al. "Single-step assembly of a gene and entire plasmid from large numbers Of oligodeoxyribonucleotides", Gene, 164(1):49-53 (1995).
Stickler, et al. "An in vitro human cell-based assay to rank the relative immunogenicity of proteins", Toxicol Sci., 77(2):280-289 (2004). Epub Dec. 22, 2003.
Stratton. "Exploring the genomes of cancer cells: progress and promise", Science, 331(6024):1553-1558 (2011). doi: 10.1126/science.1204040.
Supplementary European Search Report for European Application No. 10732172.1, May 29, 2012, 5 pages.
Swarup and Rajeswari. "Circulating (cell-free) nucleic acids—a promising, non-invasive tool for early detection of several human diseases", FEBS Letters, 581(5):795-799 (2007). Epub Feb. 2, 2007.
Szczepanski, T. et al. "Minimal residual disease in leukemia patients", Lancet Oncology, 2:409-417 (2001).
Takamatsu , et al., "A comparison between next-generation sequencing and a SO-qP CR for minimal residual disease detection in multiple myeloma", J. Clin. Oncol., 31(Supplement 1): Abstract 8601 (Conference Abstract), Entire Abstract (2013).
Tautz, et al. "Cryptic simplicity in DNA is a major source of genetic variation", Nature, 322(6080):652-656 (1986).
Tawfik, et al. "Man-made cell-like compartments for molecular evolution", Nat Biotechnol., 16(7):652-656, Abstract Only (1998).
ten Bosch et al. "Keeping Up With the Next Generation Massively Parallel Sequencing in Clinical Diagnostics", Journal of Molecular Diagnostics, 10(6):484-492 (2008).
Tewhey, R. et al. "Corrigendum: Microdroplet-based PCR enrichment for large-scale targeted sequencing", Nature Biotechnology, 28(2):178, 1 page (2010).
Tewhey, R. et al. "Microdroplet-based PCR enrichment for large-scale targeted sequencing," Nature Biotechnology, 27(11):1025-1031 (2009).
Thiel, et al. "Antigen-specific cytometry—new tools arrived!", Clin Immunol., 111(2):155-161, Abstract Only (2004).
Thor Straten, et al. "T-cell clonotypes in cancer", J Transl Med., 2(1):11, 10 pages (2004).
Triebel, F. et al. "A Unique V-J-C-Rearranged Gene Encodes A γ Protein Expressed on the Majority of CD3+ T Cell Receptor-a/fr Circulating Lymphocytes", J. Exp. Med., 167:694-699 (1988).
Tschumper, et al. "Comprehensive assessment of potential multiple myeloma immunoglobulin heavy chain V-D-J intraclonal variation using massively parallel pyrosequencing", Oncotarget, 3(4):502-513 (2012).
Turcotte and Rosenberg. "Immunotherapy for metastatic solid cancers", Adv Surg., 45:341-360 (2011).
Unrau and Deugau. "Non-cloning amplification of specific DNA fragments from whole genomic DNA digests using DNA 'indexers'", Gene., 145(2):163-169, Abstract Only, 2 pages (1994).
Urban, et al. "A systematic and quantitative analysis of PCR template contamination", J Forensic Sci., 45(6):1307-1311 (2000).
Urquhart, et al. "Rate-controlled delivery systems in drug and hormone research", Annu Rev Pharmacol Toxicol., 24:199-236, Abstract Only (1984).
Van Der Velden, V.H.J., et al. "Real-time quantitative PCR for detection of minimal residual disease before allogeneic stem cell transplantation predicts outcome in children with acute lymphoblastic leukemia", Leukemia, 15:1485-1487 (2001).
Van Der Velden, V.H.J., et al. "Optimization of PCR-based minimal residual disease diagnostics for childhood acute lymphoblastic leukemia in a multi-center setting," Leukemia, 21:706-713 (2007).
Van Dongen, J.J.M. et al. "Prognostic value of minimal residual disease in acute lymphoblastic leukaemia in childhood", The Lancet, 352:1731-1738 (1998).
Varley and Mitra. "Nested patch PCR enables highly multiplexed mutation discovery in candidate genes", Genome Research, 18: 1844-1850 (2008).
Venturi, et al. "A mechanism for TCR sharing between T cell subsets and individuals revealed by pyrosequencing", J Immunol., 186(7):4285-4294 (2011). doi: 10.4049/jimmunol.1003898. Epub Mar. 7, 2011.
Venturi, V. et al. "TCR β-Chain Sharing in Human CD8[+] T Cell Responses to Cytomegalovirus and EBV[1]", The Journal of Immunology, 181:7853-7862 (2008).
Venturi, V. et al. "The molecular basis for public T-cell responses?", Nature Reviews, 8:231-238 (2008).
Verhagen, O.J.H.M., et al. "Application of germline IGH probes in real-time quantitative PCR for the detection of minimal residual disease in acute lymphoblastic leukemia", Leukemia, 14:1426-1435 (2000).
Vester, et al. "LNA (locked nucleic acid): high-affinity targeting of complementary RNA and DNA", Biochemistry, 43(42):13233-13241, Abstract Only (2004).
Vlassov, et al. Circulating nucleic acids as a potential source for cancer biomarkers, Curr Mol Med., 10(2):142-165 (2010).
Vogelstein et al. "Cancer genome landscapes", Science, 339(6127):1546-58 (2013). doi: 10.1126/science.1235122.
Volgelstein and Kinzler. "Digital PCR," Genetics, PNAS, 96:9236-9241 (1999).
Wälchli, et al. "A practical approach to T-cell receptor cloning and expression", PLoS One, 6(11):e27930, 11 pages (2011). doi: 10.1371/journal.pone.0027930. Epub Nov. 21, 2011.

(56) References Cited

OTHER PUBLICATIONS

Ward and Marelli-Berg. "Mechanisms of chemokine and antigen-dependent T-lymphocyte navigation", *Biochem. J.*, 418:13-27 (2009).
Welch and Link. "Genomics of AML: clinical applications of next-generation sequencing", *American Society of Hematology*, 2011:30-35 (2011). doi: 10.1182/asheducation-2011.1.30.
Wells, et al. "Rapid evolution of peptide and protein binding properties in vitro", Curr Opin Biotechnol., 3(4):355-362, Abstract Only (1992).
Weusten, et al. "Principles of quantitation of viral loads ing nucleic acid sequence-based amplification in combination with homogeneo detection ing molecular beacons", Nucleic Acids Res., 30(6):e26, 7 pages (2002).
Whiteford, et al. "Swift: primary data analysis for the Illumina Solexa sequencing platform", *Bioinformatics*, 25(17):2194-2199 (2009). doi: 10.1093/bioinformatics/btp383. Epub Jun. 23, 2009.
Williams, et al. "Amplification of complex gene libraries by emulsion PCR", Nat Methods, 3(7):545-550 (2006).
Wolda. "Similarity Indices, Sample Size and Diversity", Oecologia (Berl), 50:296-302 (1981).
Wolfl, et al. "Activation-induced expression of CD137 permits detection, isolation, and expansion of the full repertoire of CD8+ T cells responding to antigen without requiring knowledge of epitope specificities", Blood, 110(1):201-210 (2007). Epub Mar. 19, 2007.
Wolfl, et al. "Use of CD137 to study the full repertoire of CD8+ T cells without the need to know epitope specificities", Cytometry A., 73(11):1043-1049 (2008). doi: 10.1002/cyto.a.20594.
Wood, B. "9-Color and 10-Color Flow Cytometry in the Clinical Laboratory", *Arch Pathol Lab Med*, 130:680-690 (2006).
Wu, H.D. et al. "The Lymphocytic Infiltration in Calcific Aortic Stenosis Predominantly Consists of Clonally Expanded T Cells", *The Journal of Immunology*, 178(8):5329-5339 (2007).
Xiong, et al. "Chemical gene synthesis: strategies, softwares, error corrections, and applications", FEMS Microbiol Rev., 32(3):522-540 (2008). doi: 10.1111/j.1574-6976.2008.00109.x. Epub Apr. 2, 2008.
Xiong, et al. "Non-polymerase-cycling-assembly-based chemical gene synthesis: strategies, methods, and progress", Biotechnol Adv., 26(2):121-134, Abstract Only (2008). Epub Nov. 7, 2007.
Xu, W. et al. "A Novel Universal Primer-Multiplex-PCR Method with Sequencing Gel Electrophoresis Analysis", *PLoS One*, 7(1):e22900, 10 pages (2012).
Yao, et al. "Analysis of the CDR3 length repertoire and the diversity of TCRα chain in human peripheral blood T Lymphocyts", *Cell Mol Immunol.*, 4(3):215-220 (2007).
Yeh, et al. "Regulating DNA translocation through functionalized soft nanopores", Nanoscale, 4(8):2685-4693, Abstract Only (2012). doi: 10.1039/c2nr30102d. Epub Mar. 15, 2012.
York, et al. "Highly parallel oligonucleotide purification and functionalization using reversible chemistry", *Nucleic Acids Res.*, 40(1):e4, 7 pages (2012). doi: 10.1093/nar/gkr910. Epub Oct. 29, 2011.
Zagnoni, et al. "Droplet Microfluidics for High-throughput Analysis of Cells and Particles", Methods in Cell Biology, Chapter 2, 102:23-48 (2011).
Zhong, Q. et al. "Multiplex digital PCR: breaking the one target per color barrier of quantitative PCR", Lab Chip, 11:2167-2174 (2011).
Office action dated Oct. 7, 2013 for U.S. Appl. No. 13/459,701.
Office action dated Oct. 16, 2013 for U.S. Appl. No. 13/487,980.
Office action dated Nov. 6, 2013 for U.S. Appl. No. 13/468,323.
Office action dated Nov. 27, 2013 for U.S. Appl. No. 13/196,885.

\* cited by examiner

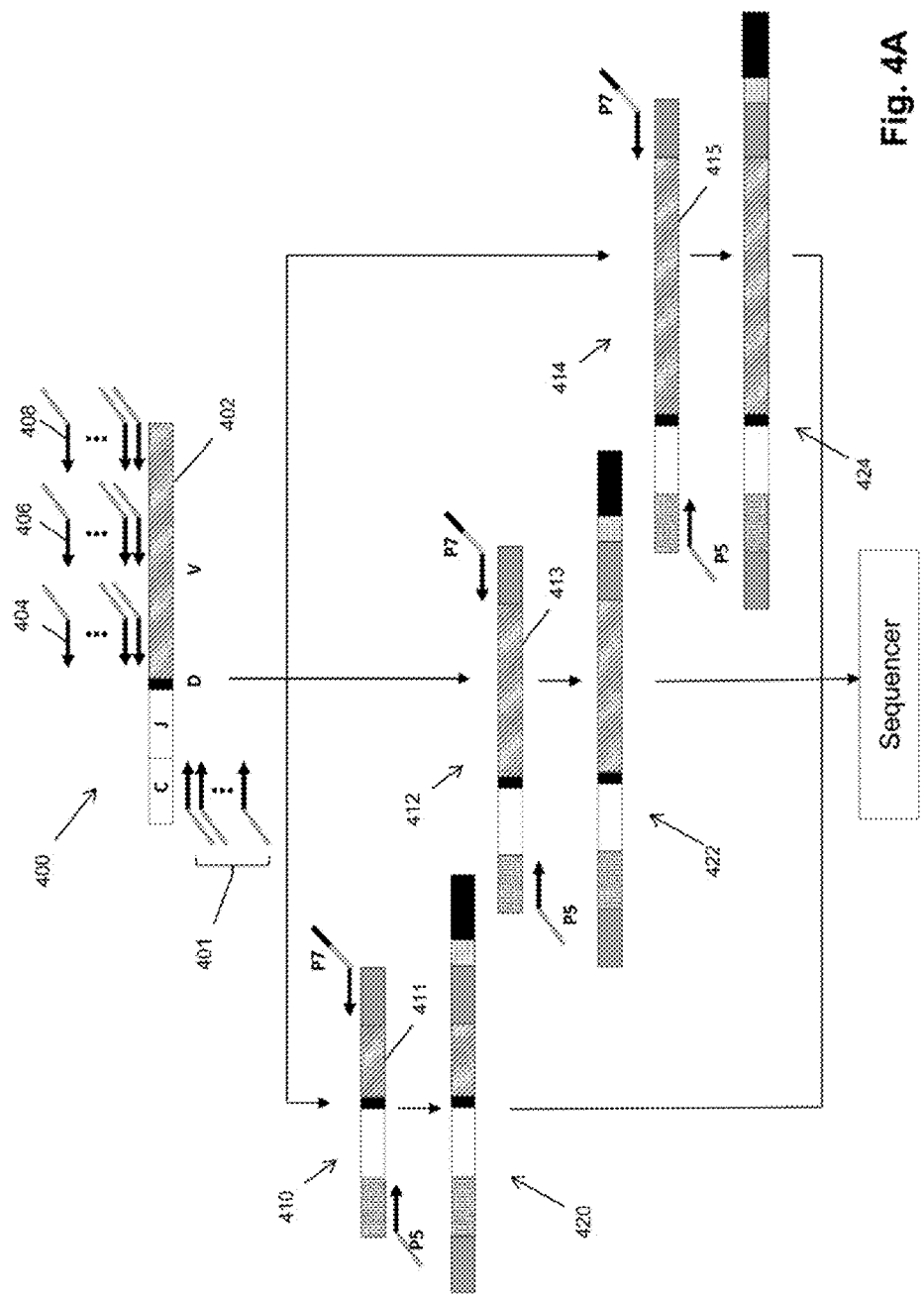

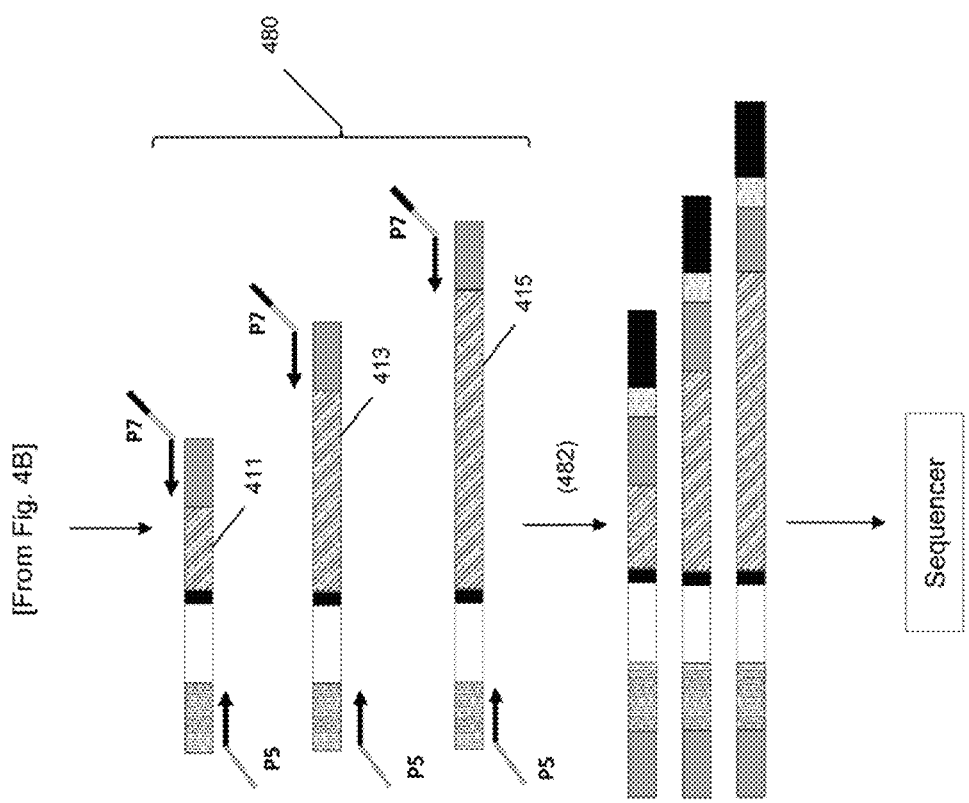

DETECTION AND MEASUREMENT OF TISSUE-INFILTRATING LYMPHOCYTES

This application claims priority to U.S. provisional, application No. 61/570,192 filed 13 Dec. 2011, which application is incorporated herein in its entirety by reference.

BACKGROUND OF THE INVENTION

The numbers and ratios of different lymphocyte subsets infiltrated into a disease-affected tissue, such as a solid tumor, often bears on the prognosis of the disease, e.g. Deschoolmeester et al, BMC immunology, 11:19 (2010); Obtain, Cancer Immunity, 7: 4 (2007); Yu et al. Laboratory investigation, 86: 233-245 (2006); Diederichsen et al. Cancer Immunol. Immmunother., 52:423-428 (2003); and the like. Unfortunately, measurement of such quantities using available technologies, such as immunohistochemistry or flow cytometry, is difficult, labor intensive, and not amenable for routine deployment.

Separately, there has been more and more interest in the use of large-scale DNA sequencing in diagnostic and prognostic applications as the per-base cost of DNA sequencing has dropped. For example, profiles of nucleic acids encoding immune molecules, such, as T cell or B cell receptors, or their components, contain a wealth of information on the state of health or disease of an organism, so that the use of such profiles as diagnostic or prognostic indicators has been proposed for a wide variety of conditions, e.g. Faham and Willis, U.S. patent publication 2910/0151471; Freeman et al. Genome Research, 19: 1817-1824 (2009); Boyd et al, Sci. Transl. Med., 1(12); 12ra23 (2009); He et al Oncotarget (Mar. 8, 2011).

If would be highly useful to the medical and scientific fields if the improvements in high throughput nucleic acid sequencing could be put to use to provide a more convenient and more effective assay for measuring tissue-infiltrating lymphocytes (TILs).

SUMMARY OF THE INVENTION

The present invention is drawn to methods for measuring numbers, levels, and/or ratios of cells, such as lymphocytes, infiltrated into a solid tissue, such as a tumor, and to making patient prognoses based on such measurements. The invention is exemplified in a number of implementations and applications, some of which are summarized below and throughout me specification.

In one aspect, the invention is directed to methods for identifying lymphocytes that have infiltrated a solid tissue comprising the following steps: (a) sorting into one or more subsets a sample of lymphocytes from an accessible tissue of an individual; (b) generating clonotype profiles for each of the one or more subsets of lymphocytes from the accessible tissue; (e) generating at least one clonotype profile from at least one sample of the solid tissue; and (d) detecting lymphocytes of each subset in the solid, tissue from their respective clonotypes.

In another aspect, the invention is directed to methods for determining a prognosis from a state of lymphocyte infiltration into a solid rumor of a patient, wherein such method comprises the steps of: (a) sorting into one or more subsets a sample of lymphocytes from peripheral blood of the patient; (b) generating clonotype profiles for each of the one or more subsets of lymphocytes from the peripheral blood; (c) generating at least one clonotype profile front at least one sample of the solid tumor; and (d) determining numbers, levels, and/or ratios of lymphocytes of each of the one or more subsets. To one embodiment, she state of lymphocyte infiltration into a solid tumor means the number, levels, and/or ratios of lymphocytes of selected functional subset within a solid tumor. In some embodiment, the state of lymphocyte infiltration into a solid tumor may also include a spatial distribution of such values within or adjacent to a solid tumor.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIG. 4A illustrates a PCR scheme for generating three sequencing templates from an IgH chain in a single reaction. FIGS. 4B-4C illustrates a PCR scheme for generating three sequencing templates from an IgH chain in three separate reactions after which the resulting amplicons are combined for a secondary PCR to add P5 and P7 primer binding sites.

DETAILED DESCRIPTION OF THE INVENTION

The practice of the present invention may employ, unless otherwise indicated, conventional techniques and descriptions of molecular biology (including recombinant techniques), bioinformatics, cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A laboratory Manual Series* (Vols. I-IV); *PCR Primer: A Laboratory Manual; and Molecular Cloning: A Laboratory Manual* (all from Cold Spring Harbor Laboratory Press); and the like.

In one aspect, the invention is directed to methods of determining the types and numbers of lymphocytes infiltrated into a solid tissue, such as a tumor, a tissue affected by an autoimmune disease, a tissue affected by graft versus host disease (GVHD), a normal tissue, or the like. Although solid tissues of interest are usually disease-affected solid tissue, in some embodiments, the levels and/or numbers and/or ratios of different subsets of lymphocytes in normal tissues may also be used to determine states of health and/or propensities of an individual to contract a disease or condition.

Figure 1:
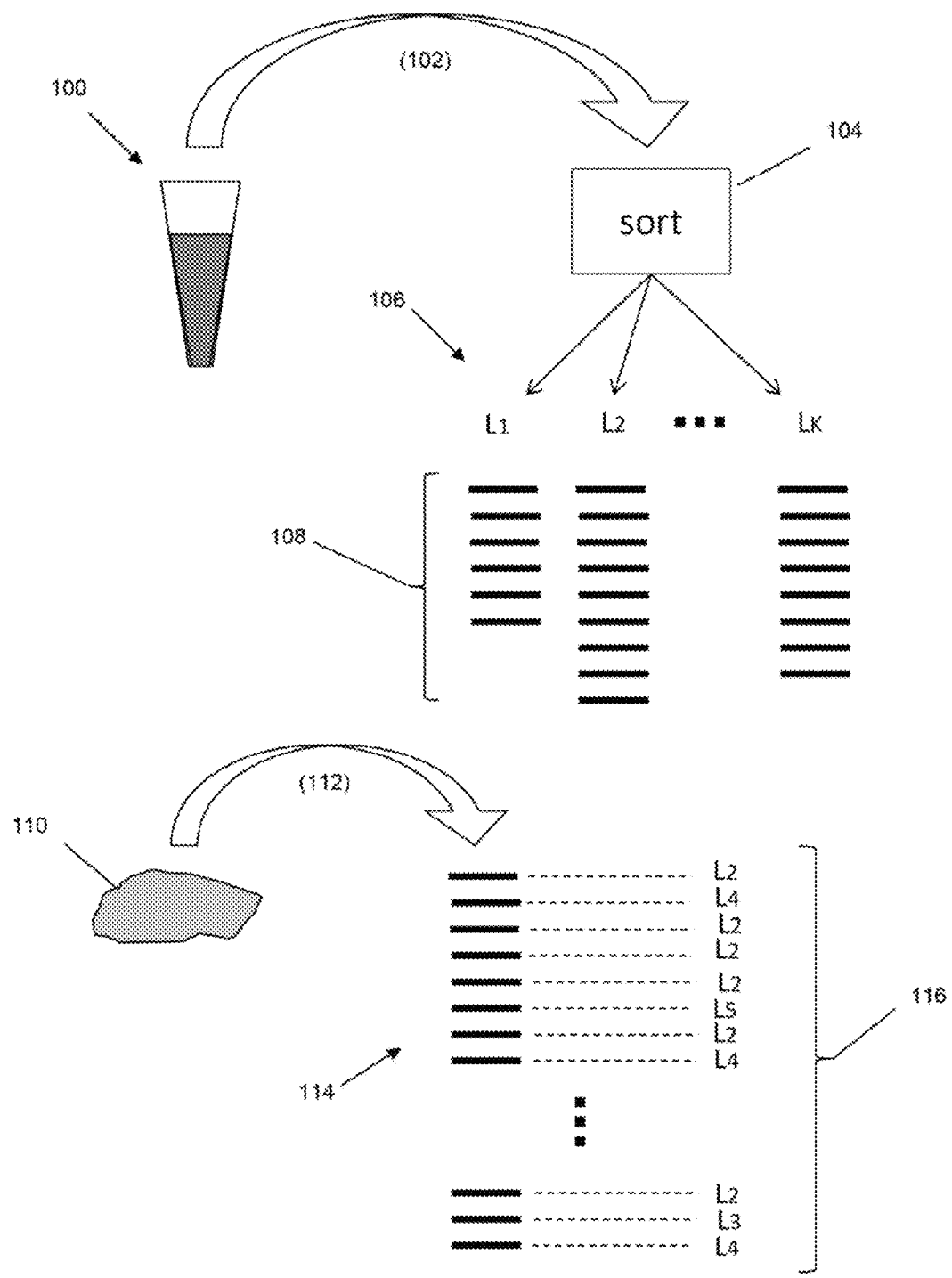
FIG. 1 illustrates diagrammatically steps of one embodiment of the invention.

An outline of one embodiment of the invention is shown in FIG. 1. Clonotypes of an individual's lymphocytes are determined from a readily accessible tissue (100), such as peripheral blood. Optionally, minimal sample preparation steps (102) may be implemented, such as isolating peripheral blood mononuclear cells (PBMCs). From such a sample, lymphocytes are sorted (104) into subsets, $L_1$, $L_2, \ldots L_K$ (106), which usually correspond to lymphocytes with distinct biological functions: such subsets are sometimes referred to herein as "functional subsets" of lymphocytes. Usually, sorting is based on the presence or absence of one or more molecular markers characteristic of such functionally distinct subsets. Such markers may be cell surface markers or intracellular markers. In one embodiment, such markers are cell surface markers. Exemplary cell surface markers include, but are not limited to, CD3, CD4, CD8, CD19, CD20, CD25, CD45RO, CD117, CD127, and the like.

Lymphocyte subsets of interest include, but are not limited to, B cells; T cells; cytotoxic T cells; helper T cells; regulatory T cells; Th1 T helper T cells; Th2 helper T cells; Th9 helper T cells; Th17 helper T cells; Tfh helper T cells; antigen-specific T cells; and antigen-specific B cells. Whenever a solid tissue is a solid tumor, of particular interest are the subsets of cytotoxic T cells and regulatory T cells.

Some subsets may include members of other subsets, either because of overlap, e.g. due to an inefficient sorting technique, or because members of a second subset may be wholly contained in (or nested in) a larger first subset; for example, the subset of T cells includes cytotoxic T cells and helper T cells as two wholly contained subsets. Likewise, the subset of helper T cells includes several other wholly contained subsets, as noted. Typically, cells of the nested subsets (i.e. subsets of subsets) are obtained by using additional markers characteristic of such subsets. Subsets of lymphocyte are usually identified functionally and/or by molecular markers using conventional assays, often with commercially available markers and kits (e.g. BD Biosciences, San Jose, Calif.). Markers characteristic for several lymphocytes of interest are as follows: CD4 for helper T cells; CD8 for cytotoxic T cells; CD4, CD25 and low expression of CD127 for regulatory T cells (or alternatively, CD4, CD25 and intracellular expression of FoxP3 for regulatory T cells); and CD45RO+, CCR7−, CD28−, CD27−, CD8+ for memory effector T cells; and the like (where the "+" and "−" symbols are used as conventional in immunology literature; that is, to indicate high expression and low (or absent) expression, respectively). Antibody probes are commercially available for isolating such subsets by sorting techniques, e.g. FACS, described below. As mentioned above, in some embodiments, the presence, absence and/or levels of lymphocytes of such subsets provide prognostic information, such as the duration of survival of a patient undergoing cancer therapy. The following Table summarizes surface and intracellular markers for identifying lymphocytes subsets in accordance with the invention. Different embodiments of the invention include identifying clonotypes of different combinations of lymphocyte subsets of the Table.

TABLE I

Exemplary Molecular Markers for Lymphocyte Subsets Useful for FACS Isolation*

| Subset | Cell Surface Markers | Intracellular Markers |
|---|---|---|
| B cells | Fc receptors, CD19+, CD20+, CD21+, CD22+, CD22+, CD23+ | |
| T cells | CD3+, CD4+, CD8+ | |
| cytotoxic T cells | CD3+, CD4−, CD8+ | |
| helper T cells | CD3+, CD4+, CD8− | |
| Th1 helper T cells | CD4+, CXCR3 | IFN-γ, IL-2, IL12, IL18, IL-27 |
| Th2 helper T cells | CD4+, CCR4, Crth2 | IL-4, IL-, IL-33 |
| Th9 helper T cells | CD4+ | IL-4, TGF-β |
| Th17 helper T cells | CD4+, CCR6 | IL-17A, IL17F, IL-21, IL-22, IL-26, TNF, CCL20 |
| Tfh helper T cells | CD4+, CXCR5 | IL-12, IL-6 |
| regulatory T cells | CD4+, CD25+, $CD127^{f\,low}$ | FoxP3 |
| antigen-specific B cells | BCRs via tetramer technology | |
| antigen-specific T cells | TCRs via tetramer technology | |

*Not meant to be an exclusive or exhaustive list.

Cell sorting based on surface markers may be carried out by one or more technologies including, but not limited to, fluorescence-activated cell sorting (FACS), magnetically-activated cell sorting (MACS), panning, resetting, and the like, which typically employ antibodies or other reagents that specifically recognize and bind to the cell surface features of interest. In one aspect, cell sorting based on intracellular markers also may be carried out using FACS by fixing and permeabilizing cells, followed by staining, e.g. with a labeled antibody specific for the intracellular marker, for example, as disclosed in Pan et al, PlosOne, 6(3): e17536 (2011). Such sorting technologies and their applications are disclosed in the following exemplary references: Recktenwald et al, editors, "Cell Separation Methods and Applications" (Marcel Dekker, 1998); Kearse, editor, "T Cell Protocols," Methods in Molecular Biology, Vol. 134 (Springer, 2000); Miltenyi et al. Cytometry, 11: 231-238 (1990); Davies, chapter 11, "Cell sorting by flow cytometry," in Macey, Editor, Flow Cytometry: Principles and Applications (Humana Press, Totowa, N.J.); and the like. On particular interest for the invention is sorting lymphocytes into subsets of interest using FACS, e.g. using a commercially available instrument and manufacturer's protocols and kits, such as a BD Biosciences FACS Aria III or a BD Biosciences Influx (BD Biosciences, San Jose, Calif.). Using FACS to isolate regulatory T cell subsets is specifically disclosed in Boyce et al, "Human regulatory T-cell isolation and measurement of function," BD Bioscience Application Note (March, 2010), which is incorporated by reference. Sorting or isolating lymphocytes based on antigen-specificity of either T cell receptors or B cell receptors may be carried out using FACS, or FACS in combination with other technologies, such as MACS. Guidance for using such technologies for sorting and/or isolating antigen-specific T cells or B cells is disclosed in the following exemplary references, which are incorporated by reference: Thiel et al, Clin. Immunol, 111 (2): 155-161 (2004); Newman et al, J. Immunol. Meth., 272: 177-187 (2003): Hoven et al, J. Immunol. Meth., 117(2): 275-284 (1989); U.S. Pat. Nos. 5,213,960 and 5,326,696; Moody et al, Cytometry A, 73A: 1086-1092 (2008); Gratama et al, Cytometry A, 58A: 79-86 (2004); Davis et al. Nature Reviews Immunology, 11: 551-558 (2011); U.S. Pat. Nos. 8,053,235 and 8,309,312; Lee et al. Nature Medicine, 5(6): 677-685 (1999); Altman et al, Science, 274: 94-96 (1996); Leisner et al, PLosOne 3(2): e1678 (2008); "Pro5 MHC Pentamer Handbook," (ProImmune, Ltd., United Kingdom, 2012); and like references.

In one embodiment, successive samples of cells from an accessible tissue (such as peripheral blood) may be sorted into two populations: (i) a single defined subset (such as CD8+ lymphocytes: CD4+, $CD25^{+(high)}$; and $CD127^{(low)}$; or the like) and (ii) all other cells. Population (i) is collected and analyzed, e.g. by extracting nucleic acids, amplifying recombined DNA or RNA sequences, sequencing them, and generating a clonotype profile. This procedure may be repeated for as many subsets as desired, using different subset-specific probes.

Returning to FIG. 1, DNA or RNA is extracted from each of the sorted subsets and clonotype profiles (108) are generated for each subset using the techniques described more fully below. The clonotype profiles provide a list of clonotype sequences in each subset. In one embodiment, the number of lymphocytes sorted is sufficiently large that substantially every T cell with a distinct clonotype may be identified in the clonotype profiles. As discussed more fully below, in some embodiments, since the identification includes a sampling, "substantially every cell with a distinct clonotype" means every clonotype at a given frequency or above, e.g. 0.0001, is determined with a probability of ninety percent, or ninety-five percent, or the like. In accordance with the invention, the clonotype information of the lymphocyte subsets is used to identity the presence, absence, numbers, and/or levels of cells of the various subsets of lymphocytes that have infiltrated into a less accessible tissue, such as a solid tumor specimen or biopsy, or tissue involved in an autoimmune disease (110). This is accomplished by extracting DNA or RNA from specimen (110) and generating (112) a clonotype profile (114). Each clonotype of profile (114) can then be associated with a lymphocyte subset (116) by looking up the sequence of such clonotype in the subset-specific clonotype profiles (108); thus, by making such an association the subsets whose members that have infiltrated the solid tissue are identified. Moreover, because of the large diversity of clonotypes, counting the clonotypes of each subset gives a good approximation of the number of lymphocytes from the subset that have infiltrated into the specimen. If the volume of the specimen is known or determinable, then the density of lymphocytes from the subset may be obtained.

In some embodiments, such as where an inaccessible tissue is a solid tumor, one or more samples of the tumor may be takers, either before or after excision, or surgical removal. Samples taken prior to tumor removal may be obtained using needle aspirations, or other conventional techniques. In some embodiments, multiple samples are obtained, for example, to determine a spatial distribution of lymphocyte subsets within an inaccessible tissue. In some embodiments, at least two samples may be taken, at least one from the surface or exterior portion of an inaccessible tissue, and at least one from the interior of the inaccessible tissue. As noted above, in some embodiments, the inaccessible tissue is a solid tumor that has been removed from a patient, such as illustrated by specimen (110) in FIG. 1. Samples from specimen (110) may be obtained after excision and after fixation. Generating clonotype profiles from fixed tissue samples is described more fully below.

In accordance with the invention, the embodiment of FIG. 1 may be implemented with the following steps: (a) sorting into one or more subsets a sample of lymphocytes from an accessible tissue of an individual; (b) generating clonotype profiles for each of the one or more subsets of lymphocytes from the accessible tissue; (c) generating a clonotype profile from a sample of the solid tissue; and (d) detecting lymphocytes of each subset in the solid tissue from their respective clonotypes. In some embodiments, step (a) may be implemented by separating lymphocytes into desired, or predetermined, subsets by a variety of techniques, as mentioned above, e.g. FACS using labeled antibody probes to appropriate markers. The objective of the step is to enrich, or preferably isolate, a pure subset, of lymphocytes from the accessible tissue in order to minimize miss-calling subset members from clonotypes identified in the inaccessible tissue. The degree of enrichment depends on the separation or sorting technique employed and available matters for the subsets. In some embodiments, the step of sorting produces at least one subset that is enriched in the target lymphocyte so that at least fifty percent of the sorted population comprises the target lymphocyte. In other embodiments, the step of sorting produces at least one subset that is enriched in the target lymphocyte so that at least eighty percent of the sorted population comprises the target lymphocyte. In other embodiments, the step of sorting produces at least one subset that is enriched in the target lymphocyte so that at least ninety percent of the sorted population comprises the target, lymphocyte. In still other embodiments, for example, when a target lymphocyte belongs to a rare cell population or no efficient probe is available, then the step of sorting may produce a subset that is enriched only to a level of five percent of the sorted population. In such cases, further enrichment may be obtained by using multiple sorting techniques in tandem, e.g. MACS followed by FACS. In some embodiments, as described below, the step of generating a clonotype profile may be implemented by amplifying recombined nucleic acids from the lymphocytes and sequencing isolated nucleic acids from the resulting amplicon. The step of generating may further include coalescing the resulting sequence reads of the sequencing step into clonotypes. Also, the step of generating may further include forming a database of the resulting clonotype sequences which is amenable to analysis, e.g. application of algorithms for comparing such sequences to clonotype sequences of other clonotype profiles.

As mentioned above, the invention includes methods for determining a prognosis from a state of lymphocyte infiltration into a solid tumor of a patient, wherein such method comprises the steps of: (a) sorting into one or more subsets a sample of lymphocytes from peripheral blood of the patient; (b) generating clonotype profiles for each of the one or more subsets of lymphocytes from the peripheral blood; (c) generating at least one clonotype profile front at least one sample of the solid tumor; and (d) determining numbers, levels, and/or ratios of lymphocytes of each of the one or more subsets. As used herein, a "prognosis" means a prediction of an outcome based on the number, levels, ratios, and/or distribution of functional subsets of lymphocytes in an inaccessible tissue, such as a solid tumor. Outcomes may be patient survival, degree of amelioration of symptoms, reduction of tumor load, or other surrogate measures of improvement or worsening of a disease condition. In some embodiments, a prognosis may be qualitative in that measurements indicate an improvement or worsening, but not a degree of improvement (e.g. number of additional years of survival, etc.) or degree of worsening. In some embodiments, levels of lymphocytes of functional subsets may be relative values, for example, in comparison with levels or concentrations (average or otherwise) in other tissues of the patient or to average levels or ranges in populations of individuals, in one embodiment, relative levels are in comparison with levels in a patient's peripheral blood of functional subsets of lymphocytes.

Samples

In accordance with the invention, lymphocytes from an accessible tissue are separated into subsets, which are analyzed to determine clonotypes which, in turn, are used to determine numbers and/or levels of lymphocytes of the different subsets in less accessible tissues; thus, in most embodiments, at least two kinds of sample are obtained, at least one from an accessible tissue and at least one from an inaccessible tissue. In some embodiments, accessible tissues from which samples are taken include, but are not limited to, peripheral blood, bone marrow, lymph fluid, synovial fluid, or the like. In some embodiments, less accessible, or inaccessible, tissues from which samples are taken are solid tissues, such as solid tumors, inflamed tissues associated with autoimmune disease, and the like. Exemplary solid tumors from which less accessible samples are taken include, but are not limited to, melanoma, colorectal, ovarian, gastric, breast, hepatocellular, urothelial, and the like. Of particular interest, are colorectal tumors and melanomas. Exemplary solid tissues related to autoimmune disease include, but are not limited to, connective tissue, joint connective tissue, muscle tissue, skin, lung tissue, small intestine tissue, colon tissue, and the like. In other embodiments, accessible tissue is peripheral blood and less accessible tissues are any tissue that would cause significant patient discomfort to sample. For example, in such embodiments, less accessible tissues may include bone marrow, lymph fluid, synovial fluid, or the like, as well as solid tissues as disclosed above.

Clonotype profiles are obtained from samples of immune cells (whether in accessible or less accessible tissues), which are present in a wide variety of tissues. Immune cells of interest include T-cells and/or B-cells. T-cells (T lymphocytes) include, for example, cells that express T cell receptors (TCRs). B-cells (B lymphocytes) include, for example, cells that express B cell receptors (BCRs). T-cells include helper T cells (effector T cells or Th cells), cytotoxic T cells (CTLs), memory T cells, and regulatory T cells, which may be distinguished by cell surface markers. In one aspect a sample of T cells includes at least 1,000 T cells; but more typically, a sample includes at least 10,000 T cells, and more typically, at least 100,000 T cells. In another aspect, a sample includes a number of T cells in the range of from 1000 to 1,000,000 cells. A sample of immune cells may also comprise B cells. B-cells include, for example, plasma B cells, memory B cells, B1 cells, B2 cells, marginal-zone B cells, and follicular B cells. B-cells can express immunoglobulins (also referred to as antibodies or B cell receptors). As above, in one aspect a sample of B cells includes at least 1,000 B cells; but more typically, a sample includes at least 10,000 B cells, and more typically, at least 100,000 B cells. In another aspect, a sample includes a number of B cells in the range of from 1000 to 1,000,000 B cells.

Samples (sometimes referred to as "tissue samples") used in the methods of the invention can come from a variety of tissues, including, for example, tumor tissue, blood and blood plasma, lymph fluid, cerebrospinal fluid surrounding the brain and the spinal cord, synovial fluid surrounding bone joints, and the like. In one embodiment, the sample is a blood sample. The blood sample can be about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mL. The sample can be a tumor biopsy. The biopsy can be from, for example, from a tumor of the brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle. In some embodiments, multiple samples may be taken from a solid tumor for the purpose of determining a spatial distribution of lymphocyte subsets within or surrounding a solid tumor. In some embodiments, a number of samples from a solid tumor may be in the range of from 2 to 10; in other embodiments, such range may be from 2 to 20.

A sample or tissue sample, whether accessible or less accessible, includes nucleic acid, for example, DNA (e.g., genomic DNA) or RNA (e.g., messenger RNA). The nucleic acid can be cell-free DNA or RNA, e.g. extracted from the circulatory system, Vlassov et al. Curr. Mol. Med., 10: 142-305 (2010); Swarup et al, FEBS Lett., 581: 795-799 (2007). In the methods of the invention, the amount of RNA or DNA from a subject that can be analyzed includes varies widely. For generating a clonotype profile, sufficient nucleic acid is obtained in a sample for a useful representation of an individual's immune receptor repertoire in the tissue. More particularly, for generating a clonotype profile from genomic DNA at least 1 ng of total DNA from T cells or B cells (i.e. about 300 diploid genome equivalents) is extracted from a sample; in another embodiment, at least 2 ng of total DNA (i.e. about 600 diploid genome equivalents) is extracted from a sample; and in another embodiment, at least 3 ng of total DNA (i.e. about 900 diploid genome equivalents) is extracted from a sample. One of ordinary skill would recognize that as the fraction of lymphocytes in a sample decreases, the foregoing minimal amounts of DNA may be increased in order to generate a clonotype profile containing more than about 1000 independent clonotypes. For generating a clonotype profile from RNA, in one embodiment, a sufficient amount of RNA is extracted so that at least 1000 transcripts are obtained which encode distinct TCRs, BCRs, or fragments thereof. The amount of RNA that corresponds to this limit varies widely from sample to sample depending on the fraction of lymphocytes in a sample, developmental stage of the lymphocytes, sampling techniques, condition of a tissue, and the like. In one embodiment, at least 100 ng of RNA is extracted from a tissue sample containing B cells and/or T cells for the generating of a clonotype profile; in another one embodiment, at least 500 ng of RNA is extracted from a tissue sample containing B cells and/or T cells for the generating of a clonotype profile. RNA used in methods of the invention may be either total RNA extracted from a tissue sample or poly A RNA extracted directly from a tissue sample or from total RNA extracted from a tissue sample. The above nucleic acid extractions may be carried out using commercially available kits, e.g. from Invitrogen (Carlsbad, Calif.), Qiagen (San Diego, Calif.), or like vendors. Guidance for extracting RNA is found in Liedtke et al. PCR Methods and Applications, 4: 185-187 (1994); and like references.

As discussed more fully below (Definitions), a sample of lymphocytes is sufficiently large so that substantially every T cell or B cell with a distinct, clonotype is represented therein, thereby forming a repertoire (as the term is used herein). In one embodiment, a sample is taken that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. In one embodiment, a sample of B cells or T cells includes at least a half million cells, and in another embodiment such sample includes at least one million cells.

Whenever a source of material front which a sample is taken is scarce, such as, clinical study samples, or the like, DNA from the material may be amplified by a non-biasing technique, such as whole genome amplification (WGA), multiple displacement amplification (MDA); or like technique, e.g. Hawkins et al, Curr. Opin. Biotech., 13: 65-67 (2002); Dean et al, Genome Research, 11: 1095-1099 (2091); Wang et al, Nucleic Acids Research, 32: e76 (2004); Hosono et al, Genome Research, 13: 954-964 (2003); and the like.

Blood samples are of particular interest as an accessible sample and may be obtained using conventional techniques, e.g. Innis et al, editors, PCR Protocols (Academic Press, 1990); or the like. For example, white blood cells may be separated from blood samples using convention techniques, e.g. RosetteSep kit (Stem Cell Technologies, Vancouver, Canada). Blood samples may range in volume from 100 µL to 10 mL; in one aspect, blood sample volumes are in the range of from 100 µL to 2 mL. DNA and/or RNA may then be extracted from such blood sample using conventional techniques for use in methods of the invention, e.g. DNeasy Blood & Tissue Kit (Qiagen, Valencia, Calif.). Optionally, subsets of white blood cells, e.g. lymphocytes, may be further isolated using conventional techniques, e.g. fluorescently activated cell sorting (FACS)(Becton Dickinson, San Jose, Calif.), magnetically activated cell sorting (MACS) (Miltenyi Biotec, Auburn, Calif.), or the like.

Since the identifying recombinations are present in the DNA of each individual's adaptive immunity cells as well as their associated RNA transcripts, either RNA or DNA can be sequenced in the methods of the provided invention. A recommitted sequence from a T-cell or B-cell encoding a T cell receptor or immunoglobulin molecule, or a portion thereof, is referred to as a clonotype. The DNA or RNA can correspond to sequences from T-cell receptor (TCR) genes or immunoglobulin (Ig) genes that encode antibodies. For example, the DNA and RNA can correspond to sequences encoding α, β, γ, or δ chains of a TCR. In a majority of T-cells, the TCR is a heterodimer consisting of an α-chain and β-chain. The TCRα chain is generated by VJ recombination, and the β chain receptor is generated by V(D)J recombination. For the TCRβ chain, in humans there are 48 V segments, 2 D segments, and 13 J segments. Several bases may be deleted and others added (called N and P nucleotides) at each of the two junctions, in a minority of T-cells, the TCRs consist of γ and δ delta chains. The TCR γ chain is generated by VJ recombination, and the TCR δ chain is generated by V(D)J recombination (Kenneth Murphy, Paul Travers, and Mark Walport, *Janeway's Immunology* 7th edition, Garland Science, 2007, which is herein incorporated by reference in its entirety).

The DNA and RNA analyzed in the methods of the invention can correspond to sequences encoding heavy chain immunoglobulins (IgH) with constant regions (α, δ, ε, γ, or µ) or light chain immunoglobulins (IgK or IgL) with constant regions λ or κ. Each antibody has two identical light chains and two identical heavy chains. Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope.

In one aspect, where the number of lymphocytes are determined in a sample, a known amount of unique immune receptor rearranged molecules with a known sequence, i.e. known amounts of one or more internal standards, is added to the cDNA or genomic DNA from a sample of unknown quantity. By counting the relative number of molecules that are obtained for the known added sequence compared to the rest of the sequences of the same sample, one can estimate the number of rearranged immune receptor molecules in the initial cDNA sample. (Such techniques for molecular counting are well-known, e.g. Brenner et al, U.S. Pat. No. 7,537,897, which is incorporated herein by reference). Data from sequencing the added unique sequence can be used to distinguish the different possibilities if a real time PCR calibration is being used as well, e.g. as disclosed in Faham and Willis (cited above).

Extraction of Nucleic Acids from Fixed Samples

Fixed tissue samples (for example, from excised tumor tissue, or the like) from which nucleic acids are extracted in conjunction with the invention are typically chemically fixed tissue sample from a disease-related tissue, such as a solid tumor. Chemical fixatives used to produce fixed tissue samples used in the invention include aldehydes, alcohols, and like reagents. Typically, fixed tissue samples used in the invention are fixed with formaldehyde or glutaraldehyde, and in particular, are provided as formalin fixed paraffin embedded (FFPE) tissue samples. Guidance for nucleic acid extraction techniques for use with the invention is disclosed in the following references, which are incorporated by reference: Dedhia et al. Asian Pacific J. Cancer Prev., 8: 55-59 (2007); Okello et al, Analytical Biochemistry, 400: 110-117 (2010); Bereczki et al. Pathology Oncology Research, 13(3): 209-214 (2007); Huijsmans et al, BMC Research Notes, 3: 239 (2010); Wood et al, Nucleic Acids Research, 38(14): e151 (2010); Gilbert et al, PLosOne, 6: e537 (June 2007); Schweiger et al, PLosOne, 4(5): e5548 (May 2009). In addition, there are several commercially available kits for carrying out nucleic acid extractions from fixed tissue that may be used with the invention using manufacturer's instructions: AllPrep DNA/RNA FFPE Kit (Qiagen, San Diego, Calif.); Absolutely RNA FFPE Kit (Agilent, Santa Clara, Calif.); QuickExtract FFPE DNA Extraction Kit (Epicentre, Madison, Wis.); RecoverAll Total Nucleic Acid Isolation Kit for FFPE (Ambion, Austin, Tex.); and the like.

Briefly, nucleic acid extraction may include the following steps: (i) obtaining fixed sample cut in sections about 20 µm thick or less and in an amount effective for yielding about 6 ng of amplifiable DNA or about 0.5 to 20 ng reverse transcribable and amplifiable RNA; (ii) optionally de-waxing the fixed sample, e.g. by xylene and ethanol washes, d-Limonene and ethanol treatment, microwave treatment, or the like; (iii) optionally treating for reversing fixative-induced cross-linking of DNA, e.g. incubation at 98° C. for 15 minutes, or the like; (iv) digesting non-nucleic acid components of the fixed sample, e.g. proteinase K in a conventional buffer, e.g. Tris-HCl, EDTA, NaCl, detergent, followed by heat denaturation of proteinase K, after which the resulting solution optionally may be used directly to generate a clonotype profile to identify correlated clonotypes; (v) and optionally extracting nucleic acid, e.g. phenol:chloroform extraction followed by ethanol precipitation; silica-column based extraction, e.g. QIAamp DNA micro kit (Qiagen, CA); or the like. For RNA isolation, a further step of RNA-specific extraction may be carried out, e.g. RNase inhibitor treatment, DNase treatment, guanidinium thiocyanate/acid extraction, or the like. Additional optional steps may include treating the extracted nucleic acid sample to remove PCR inhibitors, for example, bovine serum albumin or like reagent may be used for this purpose, e.g. Satoh et al. J. Clin. Microbiol., 36(11): 3423-3425 (1998).

The amount and quality of extracted nucleic acid may be measured in a variety of ways, including but not limited to, PICOGREEN™ Quantitation Assay (Molecular Probes, Eugene, Oreg.); analysis with a 2100 Bioanalyzer (Agilent, Santa Clara, Calif.); TBS-380 Mini-Fluoroemeter (Turner Biosystems, Sunnyvale, Calif.); or the like. In one aspect, a measure of nucleic acid quality may be obtained by amplifying, e.g. in a multiplex PCR, a set of fragments from internal standard genes which have predetermined sizes, e.g. 100, 200, 300, and 400 basepairs, as disclosed in Van Dongen et al, Leukemia, 17: 2257-2317 (2003). After such amplification, fragments are separated by size and bands are quantified to provide a size distribution that reflects the size distribution of fragments of the extracted nucleic acid.

Nucleic acids extracted from fixed tissues have a distribution of sizes with a typical average size of about 200 nucleotides or less because of the fixation process. Fragments containing clonotypes have sizes that may be in the range of from 100-400 nucleotides; thus, for DNA as the starting material, to ensure the presence of amplifiable clonotypes in the extracted nucleic acid, the number of genome equivalents in a sample must exceed the desired number clonotypes by a significant amount, e.g. typically by 3-6 fold. A similar consideration must be made for RNA as the starting material. If breaks and/or adducts from fixation are randomly distributed along an extracted sequence, then the probability that a region N basepairs in length (for example, containing a clonotype) does not have a break or adduct may be estimated as follows. If each nucleotide has a probability, p, of containing a break or adduct (e.g. p may be taken as 1/200, the inverse of the average fragment size), then an estimate of the probability that an N bp stretch will have no break or adduct, is $(1-p)^N$, e.g. Ross, Introduction to Probability Models, Ninth Edition (Academic Press, 2006). The inverse of this quantity is the factor increase in genome equivalents that must be sampled in order to get (on average) the number of desired amplifiable fragments. For example, if at least 1000 amplifiable clonotypes are desired, then there must be at least 1000 sequences encompassing the clonotypes sequences (for example, greater than 300 basepairs (bp)) that do not have breaks or amplification-inhibiting adducts or cross-linkages. For N=300 and p=1/200, $(1-p)^N \approx 0.22$, so that if a 6 ng sample was required to give about 1000 genome equivalents of intact DNA from unfixed tissue, then about $(1/0.22) \times 6$ ng, or 25-30 ng would be required from fixed tissue. For N=100 and p=1/200, $(1-p)^N \approx 0.61$, so that if a 6 ng sample was required to give about 1000 genome equivalents of intact DNA from unfixed tissue, then about $(1/0.61) \times 6$ ng, or 10 ng would be required front fixed tissue. In one aspect, for determination of correlating clonotypes, a number of amplifiable clonotypes is in the range of 1000 to 10000. Accordingly, for fixed tissue samples comprising about 50-100% lymphocytes, a nucleic acid sample from fixed tissue is obtained in an amount in the range of 10-500 ng. For fixed tissue samples comprising about 1-10% lymphocytes, a nucleic acid sample from fixed tissue is obtained in an amount in the range of 1-50 μg.

Identifying B Cell Isotypes

In one embodiment, the invention permits the identification of isotypes of B cells that infiltrate an inaccessible tissue. Isotypes of immunoglobulins produced by B lymphocytes may be determined from clonotypes that are designed to include nucleic acid that encodes a portion of the constant region of an immunoglobulin. Thus, in accordance with one aspect of the invention, clonotypes are constructed from sequence reads of nucleotides encoding immunoglobulin heavy chains (IgHs). Such clonotypes of the invention include a portion of a VDJ encoding region and a portion of its associated constant region (or C region). The isotype is determined from the nucleotide sequence encoding the portion of the C region. In one embodiment, the portion encoding the C region is adjacent to the VDJ encoding region, so that a single contiguous sequence may be amplified by a conventional technique, such as polymerase chain reaction (PCR), such as disclosed in Faham and Willis, U.S. patent publication 2011/0207134, which is incorporated herein by reference. The portion of a clonotype encoding C region is used to identify isotype by the presence of characteristic alleles. In one embodiment between 8 and 100 C-region-encoding nucleotides are included in a clonotype; in another embodiment, between 8 and 20 C-region-encoding nucleotides are included in a clonotype. In one embodiment, such C-region encoding portions are captured during amplification of IgH-encoding sequences as described more fully below. In such amplifications, one or more C-region primers are positioned so that a number of C-region encoding nucleotides in the above ranges are captured in the resulting amplicons.

There are five types of mammalian Ig heavy chain denoted by the Greek letters: α, δ, ε, γ, and μ. The type of heavy chain present defines the class of antibody; these chains are found in IgA, IgD, IgE, IgG, and IgM antibodies, respectively. Distinct heavy chains differ in size and composition; α and γ contain approximately 450 amino acids, while μ and ε have approximately 550 amino acids. Each heavy chain has two regions, the constant region and the variable region. The constant region is identical in all antibodies of the same isotype, but differs in antibodies of different isotypes. Heavy chains γ, α and δ have a constant region composed of three tandem (in a line) Ig domains, and a hinge region for added flexibility: heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain. Nucleotide sequences of human (and other) IgH C regions may be obtained from publicly available databases, such as the International Immunogenetics Information System (IMGT).

As mentioned above, in some embodiments methods of the invention provide for the generation of clonotypes of immunoglobulins containing isotype information. Such methods may be implemented with the following steps: (a) obtaining a sample of nucleic acids from lymphocytes of an individual, the sample comprising recombed sequences each including at least a portion of a C gene segment of a B cell receptor; (b) generating an amplicon from the recombined sequences, each sequence of the amplicon including a portion of a C gene segment; (e) sequencing the amplicon to generate a profile of clonotypes each comprising at least a portion of a VDJ region of a B cell receptor and at least a portion of a C gene segment. From the latter step the isotype of the sampled B lymphocytes are determined by examining the sequence of the C gene segment of its clonotype. In one embodiment, the C gene segment is from a nucleotide sequence encoding an IgH chain of said B cell receptor. Typically, the C gene segment is at one end of a clonotype and a unique recombed sequence portion, e.g. the VDJ portion, is at the other end of the clonotype. In some embodiments, the unique portions of clonotypes comprise at least a portion of a VDJ region.

Amplification of Nucleic Acid populations

Amplicons of target populations of nucleic acids may be generated by a variety of amplification techniques, in one aspect of the invention, multiplex PCR is used to amplify members of a mixture of nucleic acids, particularly mixtures comprising recombed immune molecules such as T cell receptors, or portions thereof. Guidance for carrying out multiplex PCRs of such immune molecules is found in the following references, which are incorporated by reference: Faham and Willis, U.S. patent publication 2011/0207134; Morley, U.S. Pat. No. 5,296,351; Gorski, U.S. Pat. No. 5,837,447; Dau, U.S. Pat. No. 6,087,096; Von Dongen et al, U.S. patent publication 2006/0234234; European patent publication EP 154430881; and the like.

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be found in van Dongen et al. Leukemia, 17: 2257-2317 (2003) or van Dongen et al, U.S. patent publication 2006/0234234, which is incorporated by reference. Briefly, an exemplary protocol is as follows: Reaction buffer: ABI Buffer II or ABI Gold Buffer (Life Technologies, San Diego, Calif.); 50 μL final reaction volume: 100 ng sample DNA; 10 pmol of each primer (subject to adjustments to balance amplification as described below); dNTPs at 200 μM final concentration; $MgCl_2$ at 1.5 mM final concentration (subject to optimization depending on target sequences and polymerase); Taq polymerase (1-2 U/tube); cycling conditions: preactivation 7 min at 95° C.; annealing at 60° C.; cycling times: 30 s denaturation; 30 s annealing; 30 s extension. Polymerases that can be used for amplification in the methods of the invention are commercially available and include, for example, Taq polymerase, AccuPrime polymerase, or Pfu. The choice of polymerase to use can be based on whether fidelity or efficiency is preferred.

Real time PCR, PICOGREEN™ staining, nanofluidic electrophoresis (e.g. LABCHIP™ nanofluidic electrophoresis or UV absorption measurements can be used in an initial step to judge the functional amount of amplifiable material.

In one aspect, multiplex amplifications are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two fold of its value in the starting sample. As discussed more fully below, amplification bias in PCR may be detected and corrected using conventional techniques so that a set of PCR primers may be selected for a predetermined repertoire that provide unbiased amplification of any sample.

In regard to many repertoires based on TCR or BCR sequences, a multiplex, amplification optionally uses all the V segments. The reaction is optimized to attempt to get amplification that maintains the relative abundance of the sequences amplified by different V segment primers. Some of the primers are related, and hence many of the primers may "cross talk," amplifying templates that are not perfectly matched with it. The conditions are optimized so that each template can be amplified in a similar fashion irrespective of which primer amplified it. In other words if there are two templates, then after 1,000 fold amplification both templates can be amplified approximately 1,000 fold, and it does not matter that for one of the templates half of the amplified products carried a different primer because of the cross talk. In subsequent analysis of the sequencing data the primer sequence is eliminated from the analysis, and hence it does not matter what primer is used in the amplification as long as the templates are amplified equally.

In one embodiment, amplification bias may be avoided by carrying out a two-stage amplification (as described in Faham and Willis, cited above) wherein a small number of amplification cycles are implemented in a first, or primary, stage using primers having tails non-complementary with the target sequences. The tails include primer binding sites that, are added to the ends of the sequences of the primary amplicon so that such sites are used in a second stage amplification using only a single forward primer and a single reverse primer, thereby eliminating a primary cause of amplification bias. Preferably, the primary PCR will have a small enough number of cycles (e.g. 5-10) to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 fold dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation from 300,000 molecules to the secondary amplification would degrade the precision of estimating the relative abundance of the different species in the original sample. The 100 fold dilution between the 2 steps means that the representation is reduced unless the primary PCR amplification generated significantly more than 100 molecules. This indicates that a minimum 8 cycles (256 fold), but more comfortably 10 cycle (~1,000 fold), may be used. The alternative to that is to take more than 1% of the primary PCR into the secondary but because of the high concentration of primer used in the primary PCR, a big dilution factor is can be used to ensure these primers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

Generating Sequence Reads for Clonotypes

Any high-throughput technique for sequencing nucleic acids can be used in the method of the invention. Preferably, such technique has a capability of generating in a cost-effective manner a volume of sequence data from which at least 1000 clonotypes can be determined, and preferably, from which at least 10,000 to 1,000,000 clonotypes can be determined. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD™ sequencing. Sequencing of the separated molecules has more recently been demonstrated by sequential or single extension reactions using polynmerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR).

In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing. e.g. Bentley et al. Nature, 456: 53-59 (2008) or Complete Genomics sequencing, e.g. Drmanac et al, Science, 327: 78-81 (2010)), arrays of wells, which may include bead- or particle-bound templates (such as with 454. e.g. Margulies et al, Nature, 437: 376-380 (2005) or Ion Torrent sequencing. U.S. patent publication 2010/0137143 or 2010/0304982), micrommachined membranes (such as with SMRT sequencing, e.g. Eid et al, Science, 323: 133-138 (2009)), or bead arrays (as with SOLiD™ sequencing or polony sequencing, e.g. Kim et al, Science, 316: 1481-1414 (2007)).

In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference. In one embodiment, individual molecules disposed and amplified on a solid surface form clusters in a density of at least $10^3$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

In one aspect, a sequence-based clonotype profile of an individual is obtained using the following steps: (a) obtaining a nucleic acid sample from T-cells and/or B-cells of the individual; (b) spatially isolating individual molecules derived from such nucleic acid sample, the individual molecules comprising at least one template generated from a nucleic acid in the sample, which template comprises a somatically rearranged region or a portion thereof, each individual molecule being capable of producing at least one sequence read; (c) sequencing said spatially isolated individual molecules; and (d) determining abundances of different sequences of the nucleic acid molecules from the nucleic acid sample to generate the clonotype profile. In another embodiment, a sequence-based clonotype profile may be generated by the following steps: (a) obtaining a sample from the patient comprising T-cells and/or B-cells; (b) amplifying molecules of nucleic acid from the T-cells and/or B-cells of the sample, the molecules of nucleic acid comprising recombined sequences from T-cell receptor genes or immunoglobulin genes; (c) sequencing the amplified molecules of nucleic acid to form a clonotype profile; and (d) determining a presence, absence and/or level of the one or more patient-specific clonotypes, including any previously unrecorded phylogenic clonotypes thereof, as taught by Faham and Willis, U.S. patent publication 2011/0207134, which is incorporated herein by reference.

In one embodiment, each of the somatically rearranged regions comprise a V region and a J region. In another embodiment, the step of sequencing comprises bidirectionally sequencing each of the spatially isolated individual molecules to produce at least one forward sequence read and at least one reverse sequence read. Further to the latter embodiment, at least one of the forward sequence reads and at least one of the reverse sequence reads have an overlap region such that bases of such overlap region are determined by a reverse complementary relationship between such sequence reads. In still another embodiment, each of the somatically rearranged regions comprise a V region and a J region and the step of sequencing further includes determining a sequence of each of the individual nucleic acid molecules from one or more of its forward sequence reads and at least one reverse sequence read starting from a position in a J region and extending in the direction of its associated V region. In another embodiment, individual molecules comprise nucleic acids selected from the group consisting of complete IgH molecules, incomplete IgH molecules, complete IgK complete, IgK inactive molecules, TCRβ molecules, TCRγ molecules, complete TCRδ molecules, and incomplete TCRδ molecules. In another embodiment, the step of sequencing comprises generating the sequence reads having monotonically decreasing quality scores. Further to the latter embodiment, monotonically decreasing quality scores are such that the sequence reads have error rates no better than the following: 0.2 percent of sequence reads contain at least one error in base positions 1 to 50, 0.2 to 1.0 percent of sequence reads contain at least one error in positions 51-75, 0.5 to 1.5 percent of sequence reads contain at least one error in positions 76-100. In another embodiment, the above method comprises the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof, each nested set being capable of producing a plurality of sequence reads each extending in the same direction and each starting from a different position on the nucleic acid from which the nested set was generated; (c) sequencing said spatially isolated individual molecules; and (d) determining abundances of different sequences of the nucleic acid molecules from the nucleic acid sample to generate the clonotype profile. In one embodiment, the step of sequencing includes producing a plurality of sequence reads for each of the nested sets. In another embodiment, each of the somatically rearranged regions comprise a V region and a J region, and each of the plurality of sequence reads starts from a different position in the V region and extends in the direction of its associated J region.

In one aspect, for each sample from an individual, the sequencing technique used in the methods of the invention generates sequences of least 1000 clonotypes per run; in another aspect, such technique generates sequences of at least 10,000 clonotypes per run; in another aspect, such technique generates sequences of at least 100,000 clonotypes per run; in another aspect, such technique generates sequences of at least 500,000 clonotypes per run; and in another aspect, such technique generates sequences of at least 1,000,000 clonotypes per run. In still another aspect, such technique generates sequences of between 100,000 to 1,000,000 clonotypes per run per individual sample.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

Clone-Type Determination, from Sequence Date

Constructing clonotypes from sequence read data depends in part on the sequencing method used to generate such data, as the different methods have different expected read lengths and data quality. In one approach, a Solexa sequencer is employed to generate sequence read data for analysis. In one embodiment, a sample is obtained that provides at least 0.5-1.0×1.0" lymphocytes to produce at least 1 million template molecules, which after optional amplification may produce a corresponding one million or more clonal populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 times or more. For other sequencing approaches with different expected read lengths and data quality, different levels of redundancy may be used for comparable accuracy of sequence determination. Those of ordinary skill in the art recognize that the above parameters, e.g. sample size, redundancy, and the like, are design choices related to particular applications.

Figure 4B:
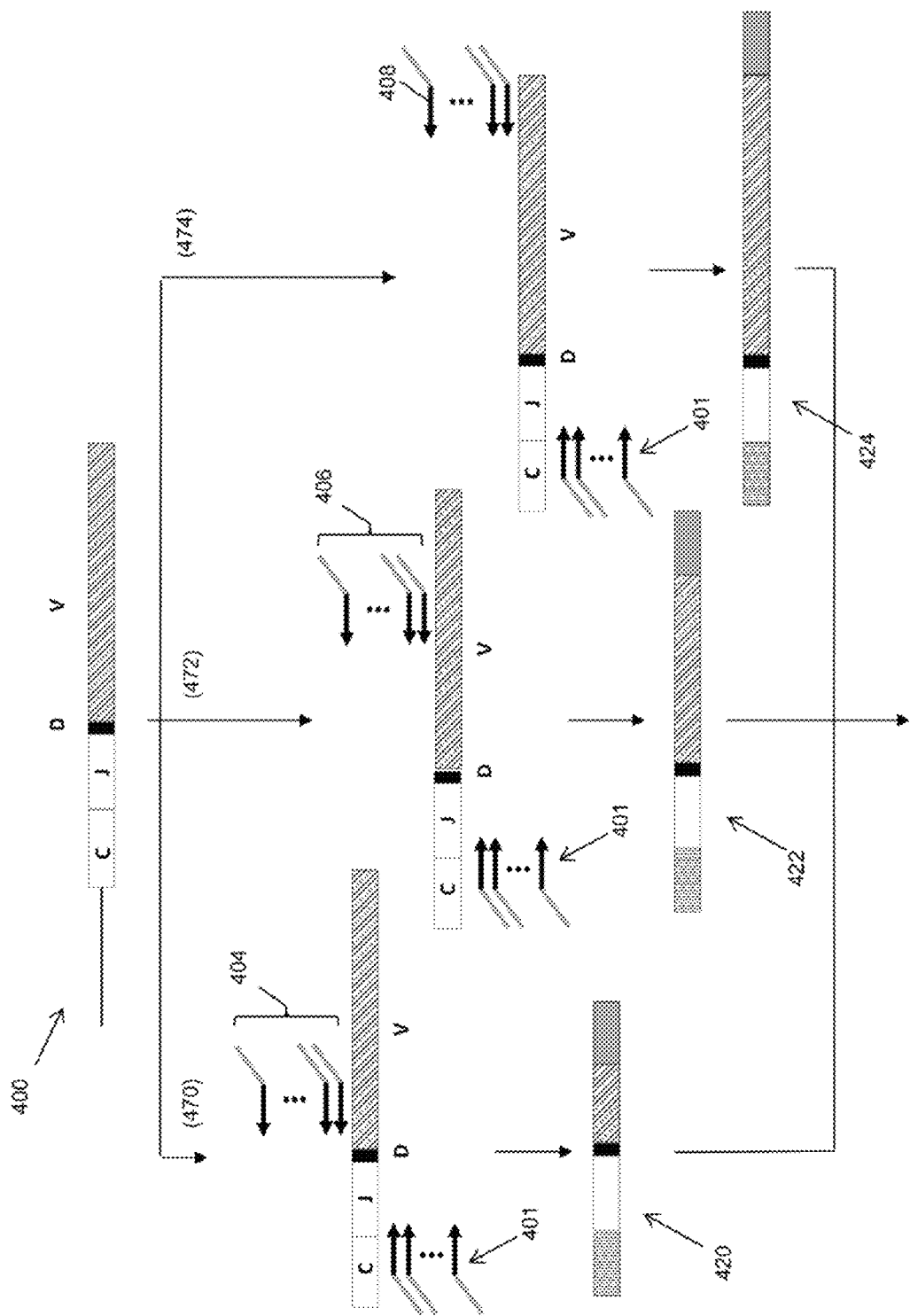

In one aspect of the invention, sequences of clonotypes (including but not limited to those derived from IgH, TCRα, TCRβ, TCRγ, TCRδ, and/or IgLκ (IgK)) may be determined by combining information from one or more sequence reads, for example, along the V(D)J regions of the selected chains. In another aspect, sequences of clonotypes are determined by combining information from a plurality of sequence reads. Such pluralities of sequence reads may include one or more sequence reads along a sense strand (i.e. "forward" sequence reads) and one or more sequence reads along its complementary strand (i.e. "reverse" sequence reads). When multiple sequence reads are generated along the same strand, separate templates are first generated by amplifying sample molecules with primers selected for the different positions of the sequence reads. This concept is illustrated in FIG. 4A where primers (404, 406 and 408) are employed to generate amplicons (410, 412, and 414, respectively) in a single reaction. Such amplifications may be carried out in the same reaction or in separate reactions. In one aspect, whenever PCR is employed, separate amplification reactions are used for generating the separate templates which, in turn, are combined and used to generate multiple sequence reads along the same strand. This latter approach is preferable for avoiding the need to balance primer concentrations (and/or other reaction parameters) to ensure equal amplification of the multiple templates (sometimes referred to herein as "balanced amplification" or "unbias amplification"). The generation of templates in separate reactions is illustrated in FIGS. 4B-4C. There a sample containing IgH (400) is divided into three portions (472, 474, and 476) which are added to separate PCRs using J region printers (401) and V region primers (404, 406, and 408, respectively) to produce amplicons (420, 422 and 424, respectively). The latter amplicons are then combined (478) in secondary PCR (480) using P5 and P7 primers to prepare the templates (482) for bridge PCR and sequencing on an Illumina GA sequencer, or like instrument.

Sequence reads of the invention may have a wide variety of lengths, depending in part on the sequencing technique being employed. For example, for some techniques, several trade-offs may arise in its implementation, for example, (i) the number and lengths of sequence reads per template and (ii) the cost and duration of a sequencing operation. In one embodiment, sequence reads are in the range of from 20 to 400 nucleotides; in another embodiment, sequence reads are in a range of from 30 to 200 nucleotides: in still another embodiment, sequence reads are in the range of from 30 to 120 nucleotides. In one embodiment, 1 to 4 sequence reads are generated for determining the sequence of each clonotype; in another embodiment, 2 to 4 sequence reads are generated for determining the sequence of each clonotype; and in another embodiment, 2 to 3 sequence reads are generated for determining the sequence of each clonotype. In the foregoing embodiments, the numbers given are exclusive of sequence reads used to identify samples from different individuals. The lengths of the various sequence reads used in the embodiments described below may also vary based on the information that is sought to be captured by the read; for example, the starting location and length of a sequence read may be designed to provide the length of an NDN region as well as its nucleotide sequence; thus, sequence reads spanning the entire NDN region are selected. In other aspects, one or more sequence reads that in combination (but not separately) encompass a D and/or NDN region are sufficient.

As mentioned above, a variety of algorithms may be used to convert sequence reads into clonotypes. In one embodiment, sequences of clonotypes are determined in part by aligning sequence reads to one or more V region reference sequences and one or more J region reference sequences, and in part by base determination without alignment to reference sequences, such as in the highly variable NDN region. A variety of alignment algorithms may be applied to the sequence reads and reference sequences. For example, guidance for selecting alignment methods is available in Batzoglou, Briefings in Bioinformatics, 6: 6-22 (2005), which is incorporated by reference. In one aspect, whenever V reads or C reads (as mentioned above) are aligned to V and J region reference sequences, a tree search algorithm is employed, e.g. as described generally in Gusfield (cited above) and Cormen et al, Introduction to Algorithms, Third Edition (The MIT Press, 2009).

Figure 3A:
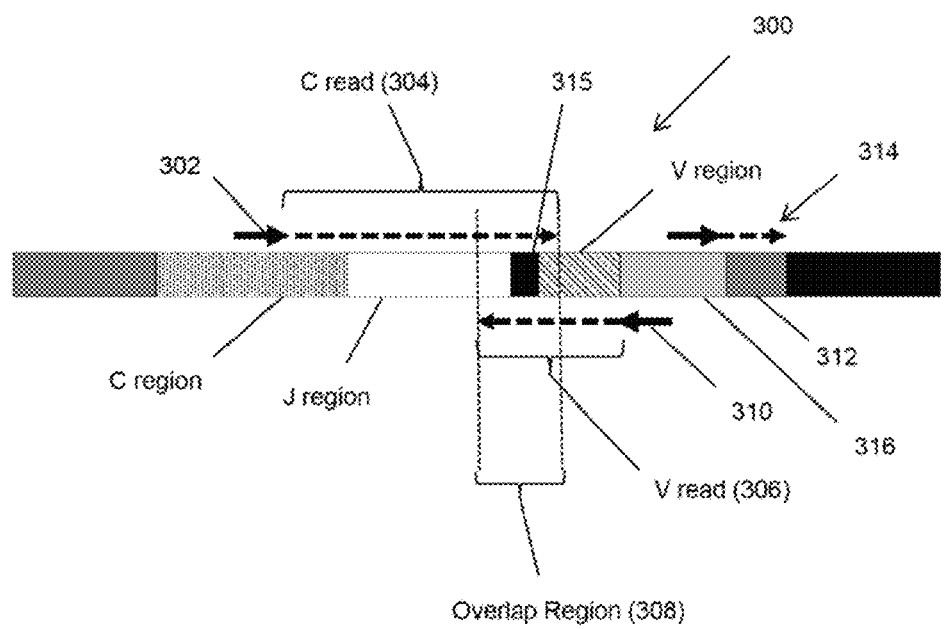
FIG. 3A illustrates details of determining a nucleotide sequence of the PCR product of FIG. 2C.
Figure 3B:
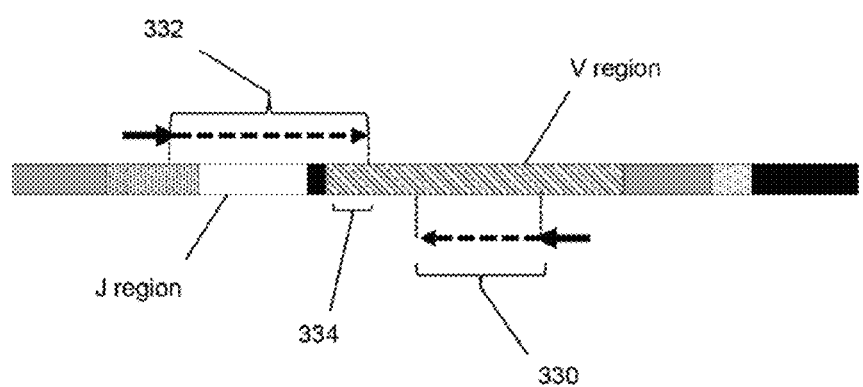
FIG. 3B illustrates details of another embodiment of determining a nucleotide sequence of the PCR product of FIG. 2C.

In another embodiment, an end of at least one forward read and an end of at least one reverse read overlap in an overlap region (e.g. 308 in FIG. 3B), so that the bases of the reads are in a reverse complementary relationship with one another. Thus, for example, if a forward read in the overlap region is "5'-acgttgc", then a reverse read in a reverse complementary relationship is "5'-gcaacgt" within the same overlap region. In one aspect, bases within such an overlap region are determined, at least in part, from such a reverse complementary relationship. That is, a likelihood of a base call (or a related quality score) in a prospective overlap region is increased if it preserves, or is consistent with, a reverse complementary relationship between the two sequence reads. In one aspect, clonotypes of TCRβ and IgH chains (illustrated in FIG. 3B) are determined by at least one sequence read starting in its J region and extending in the direction of its associated V region (referred to herein as a "C read" (304)) and at least one sequence read starting in its V region and extending in the direction of its associated J region (referred to herein as a "V read" (306)). Overlap region (308) may or may not encompass the NDN region (315) as shown in FIG. 3B. Overlap region (308) may be entirely in the J region, entirely in the NDN region, entirely in the V region, or it may encompass a J region-NDN region boundary or a V region-NDN region boundary, or both such boundaries (as illustrated in FIG. 3B). Typically, such sequence reads are generated by extending sequencing primers, e.g. (302) and (310) in FIG. 3B, with a polymerase in a sequencing-by-synthesis reaction, e.g. Metzger, Nature Reviews Genetics, 11: 31-46 (2010); Fuller et al, Mature Biotechnology, 27: 1013-1023 (2009). The binding sites for primers (302) and (310) are predetermined, so that they can provide a starting point or anchoring point for initial alignment and analysis of the sequence reads. In one embodiment, a C read is positioned so that it encompasses the D and/or NDN region of the TCRβ or IgH chain and includes a portion of the adjacent V region, e.g. as illustrated in FIGS. 3B and 3C. In one aspect, the overlap of the V read and the C read in the V region is used to align the reads with one another. In other embodiments, such alignment of sequence reads is not necessary, e.g. with TCRβ chains, so that a V read may only be long enough to identify the particular V region of a clonotype. This latter aspect is illustrated in FIG. 3C. Sequence read (330) is used to identify a V region, with or without overlapping another sequence read, and another sequence read (332) traverses the NDN region and is used to determine the sequence thereof. Portion (334) of sequence read (332) that extends into the V region is used to associate the sequence information of sequence read (332) with that of sequence read (330) to determine a clonotype. For some sequencing methods, such as base-by-base approaches like the Solexa sequencing method, sequencing run time and reagent costs are reduced by minimizing the number of sequencing cycles in an analysis. Optionally, as illustrated, in FIG. 3B, amplicon (300) is produced with sample tag (312) to distinguish between clonotypes originating from different biological samples, e.g. different patients. Sample tag (312) may be identified by annealing a primer to primer binding region (316) and extending it (314) to produce a sequence read across tag (312), from which sample tag (312) is decoded.

Figure 4D:
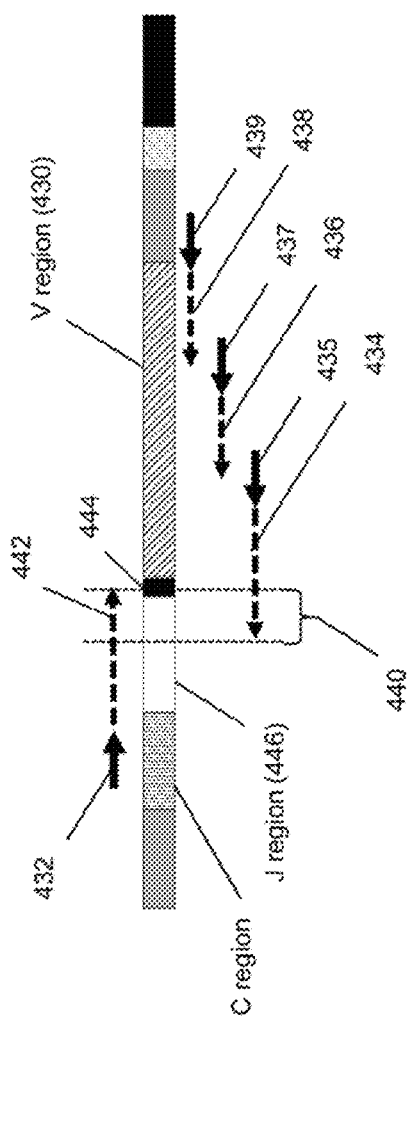
FIG. 4D illustrates the locations of sequence reads generated for an IgH chain.

The IgH chain is more challenging to analyze than TCRβ chain because of at least two factors; i) the presence of somatic mutations makes the mapping or alignment more difficult, and ii) the NDN region is larger so that it is often not possible to map a portion of the V segment to the C read. In one aspect of the invention, this problem is overcome by using a plurality of primer sets for generating V reads, which are located at different locations along the V region, preferably so that the primer binding sites are nonoverlapping and spaced apart, and with at least one primer binding site adjacent to the NDN region, e.g. in one embodiment from 5 to 50 bases from the V-NDN junction, or in another embodiment from 10 to 50 bases from the V-NDN junction. The redundancy of a plurality of primer sets minimizes the risk of falling to detect a clonotype due to a failure of one or two primers having binding sites affected by somatic mutations. In addition, the presence of at least one primer binding site adjacent to the NDN region makes it more likely that a V read will overlap with the C read and hence effectively extend the length of the C read. This allows for the generation of a continuous sequence that spans all sizes of NDN regions and that can also map substantially the entire V and J regions on both sides of the NDN region. Embodiments for carrying out such a scheme are illustrated in FIGS. 4A and 4D. In FIG. 4A, a sample comprising IgH chains (400) are sequenced by generating a plurality amplicons for each chain by amplifying the chains with a single set of J region primers (401) and a plurality (three shown) of sets of V region (402) primers (404, 406, 408) to produce a plurality of nested amplicons (e.g., 410, 412, 416) all comprising the same NDN region and having different lengths encompassing successively larger portions (411, 413, 415) of V region (402). Members of a nested set may be grouped together after sequencing by noting the identify (or substantial identity) of their respective NDN, J and/or C regions, thereby allowing reconstruction of a longer V(D)J segment than would be the case otherwise for a sequencing platform with limited read length and/or sequence quality. In one embodiment, the plurality of primer sets may be a number in the range of from 2 to 5. In another embodiment the plurality is 2-3; and still another embodiment the plurality is 3. The concentrations and positions of the primers in a plurality may vary widely. Concentrations of the V region primers may or may not be the same, in one embodiment, the primer closest to the NDN region has a higher concentration than the other primers of the plurality, e.g. to insure that amplicons containing the NDN region are represented in the resulting amplicon. In a particular embodiment where a plurality of three primers is employed, a concentration ratio of 60:20:20 is used. One or more primers (e.g. 435 and 437 in FIG. 4B) adjacent to the NDN region (444) may be used to generate one or more sequence reads (e.g. 434 and 436) that overlap the sequence read (442) generated by J region primer (432), thereby improving the quality of base calls in overlap region (440). Sequence reads from the plurality of primers may or may not overlap the adjacent downstream primer binding site and/or adjacent downstream sequence read. In one embodiment, sequence reads proximal to the NDN region (e.g. 436 and 438) may be used to identify the particular V region associated with the clonotype. Such a plurality of primers reduces the likelihood of incomplete or failed amplification in case one of the primer binding sites is hypermutated during immunoglobulin development. It also increases the likelihood that diversity introduced by hypermutation of the V region will be capture in a clonotype sequence. A secondary PCR may be performed to prepare the nested amplicons for sequencing, e.g. by amplifying with the P5 (401) and P7 (404, 406, 408) primers as illustrated to produce amplicons (420, 422, and 424), which may be distributed as single molecules on a solid surface, where they are further amplified by bridge PCR, or like technique.

Figure 4E:
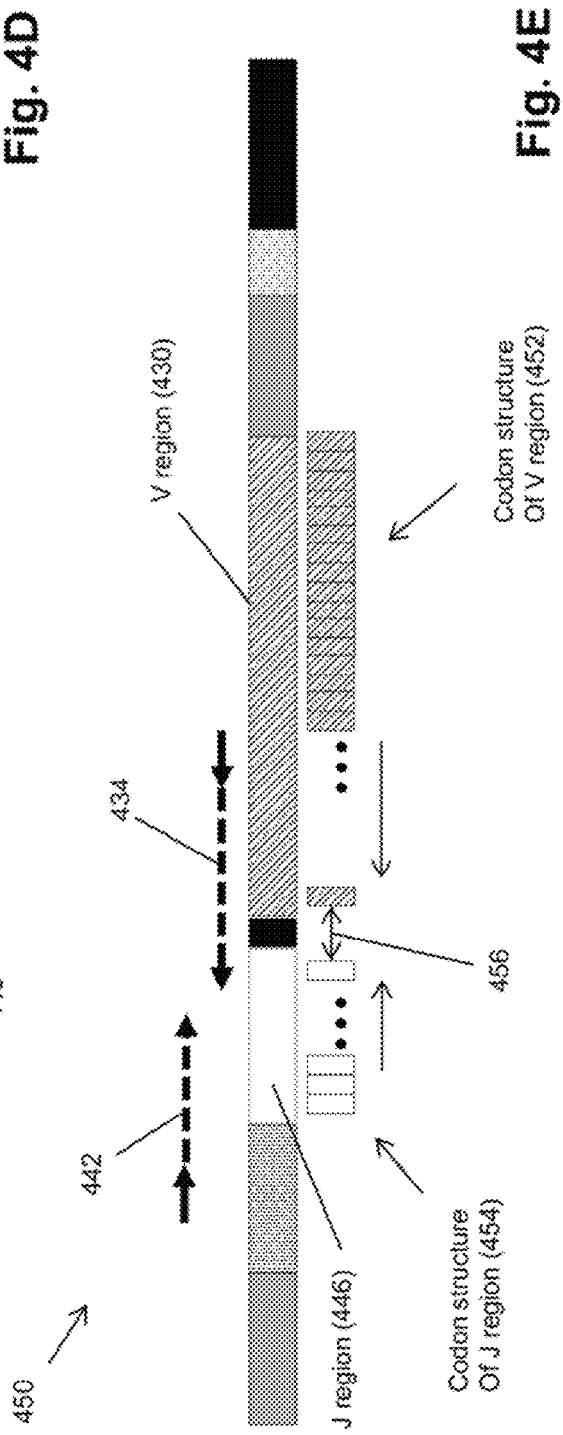
FIG. 4E illustrates the use of the codon structure of V and J regions to improve base calls in the NDN region.

Base calling in NDN regions (particularly of IgH chains) can be improved by using the codon structure of the flanking J and V regions, as illustrated in FIG. 4E. (As used herein, "codon structure" means the codons of the natural reading frame of segments of TCR or BCR transcripts or genes outside of the NDN regions, e.g. the V region, J region, or the like.) There amplicon (450), which is an enlarged view of the amplicon of FIG. 4B, is shown along with the relative positions of C read (442) and adjacent V read (434) above and the codon structures (452 and 454) of V region (430) and J region (446), respectively, below. In accordance with this aspect of the invention, after the codon structures (452 and 454) are identified by conventional alignment to the V and J reference sequences, bases in NDN region (456) are called (or identified) one base at a time moving from J region (446) toward V region (430) and in the opposite direction from V region (430) toward J region (446) using sequence reads (434) and (442). Under normal biological conditions, only the recombined TCR or IgH sequences that have in frame codons from the V region through the NDN region and to the J region are expressed as proteins. That is, of the variants generated somatically only ones expressed are those whose J region and V region codon frames are in-frame with one another and remain in-frame through the NDN region. (Here the correct frames of the V and J regions are determined from reference sequences). If an out-of-frame sequence is identified based one or more low quality base calls, the corresponding clonotype is flagged for re-evaluation or as a potential disease-related anomaly. If the sequence identified is in-frame and based on high quality base calls, then there is greater confidence that the corresponding clonotype has been correctly called. Accordingly, in one aspect, the invention includes a method of determining V(D)J-based clonotypes from bidirectional sequence reads comprising the steps of: (a) generating at least one J region sequence read that begins in a J region and extends into an NDN region and at least one V region sequence read that begins in the V regions and extends toward the NDN region such that the J region sequence read and the V region sequence read are overlapping in an overlap region, and the J region and the V region each have a codon structure; (b) determining whether the codon structure of the J region extended into the NDN region is in frame with the codon structure of the V region extended toward the NDN region. In a further embodiment, the step of generating includes generating at least one V region sequence read that begins in the V region and extends through the NDN region to the J region, such that the J region sequence read and the V region sequence read are overlapping in an overlap region.

In some embodiments, IgH-based clonotypes that have undergone somatic hypermutation may be determined as follows. A somatic mutation is defined as a sequenced base that is different from the corresponding base of a reference sequence (of the relevant, segment, usually V, J or C) and that is present in a statistically significant number of reads. In one embodiment, C reads may be used to find somatic mutations with respect to the mapped J segment and likewise V reads for the V segment. Only pieces of the C and V reads are used that are either directly mapped to J or V segments or that are inside the clonotype extension up to the NDN boundary. In this way, the NDN region is avoided and the same 'sequence information' is not used for mutation finding that was previously used for clonotype determination (to avoid erroneously classifying as mutations nucleotides that are really just different recombined NDN regions). For each segment type, the mapped segment (major allele) is used as a scaffold and all reads are considered which have mapped to this allele during the read mapping phase. Each position of the reference sequences where at least one read has mapped is analyzed for somatic mutations. In one embodiment, the criteria for accepting a non-reference base as a valid mutation include the following: 1) at least N reads with the given mutation base, 2) at least a given fraction N/M reads (where M is the total number of mapped reads at this base position) and 3) a statistical cut based on the binomial distribution, the average Q score of the N reads at the mutation base as well as the number (M−N) of reads with a non-mutation base. Preferably, the above parameters are selected so that the false discovery rate of mutations per clonotype is less than 1 in 1000, and more preferably, less than 1 in 10000.

Sequence-tag-based methods are an alternative to the above approaches for constructing clonotypes from sequence data. Sequence data typically comprises a large collection of sequence reads, i.e. sequences of base calls and associated quality scores, from a DNA sequencer used to analyze the immune molecules. A key challenge in constructing clonotype profiles is to rapidly and accurately distinguish sequence reads that contain genuine differences from those that contain errors from non-biological sources, such as the extraction steps, sequencing chemistry, amplification chemistry, or the like. In one approach to generating clonotypes, a unique sequence tag may be attached to each clonotype in a sample to assist in determining whether sequence reads of such conjugates are derived from the same original clonotype before amplification or sequencing. Sequence tags may be attached to the somatically recombined nucleic acid molecules to form tag-molecule conjugates wherein each recombined nucleic acid of such a conjugate has a unique sequence tag. Usually such attachment is made after nucleic acid molecules are extracted from a sample containing T cells and/or B cells. Preferably, such unique sequence tags differ greatly from one another as determined by conventional distance measures for sequences, such as, Hamming distance, or the like; thus, copies of each sequence tag in tag-molecule conjugates remains far closer to its ancestoral tag sequence than to that of any other unique tag sequence, even with a high rate of sequencing or amplification errors introduced by steps of the invention. For example, if 16-mer sequence tags are employed and each such tag on a set of clonotypes has a Hamming distance of at least fifty percent, of eight nucleotides, from every other sequence tag on the clonotypes, then at least eight sequencing or amplification errors would be necessary to transform one such tag into another for a mis-read of a sequence tag (and the incorrect grouping of a sequence read of a clonotype with the wrong sequence tag). In one embodiment, sequence tags are selected so that after attachment to recombined nucleic acids molecules to form tag-molecule conjugates, the Hamming distance between tags of the tag-molecule conjugates is a number at least twenty-five percent of the total length of such sequence tags (that is, each sequence tag differs in sequence from every other such tag in at least 25 percent of its nucleotides); in another embodiment, the Hamming distance between such sequence tags is a number at least 50 percent of the total length of such sequence tags.

In one aspect, the above approach is implemented by the following steps: (a) obtaining a sample from an individual comprising T-cells and/or B-cells; (b) attaching sequence tags to molecules of recombined nucleid acids of T-cell receptor genes or immunoglobulin genes of the T-cells and/or B-cells to form tag-molecule conjugates, wherein substantially every molecule of the tag-molecule conjugates has a unique sequence tag; (c) amplifying the tag-molecule conjugates; (d) sequencing the tag-molecule conjugates; and (e) aligning sequence reads of like sequence tags to determine sequence reads corresponding to the same clonotypes of the repertoire. Samples containing B-cells or T-cells are obtained using conventional techniques, as described more fully below. In the step of attaching sequence tags, preferably sequence tags are not only unique but also are sufficiently different from one another that the likelihood of even a large number of sequencing or amplification errors transforming one sequence tag into another would be close to zero. After attaching sequence tags, amplification of the tag-molecule conjugate is necessary for most sequencing technologies; however, whenever single-molecule sequencing technologies are employed an amplification step is optional. Single molecule sequencing technologies include, but are not limited to, single molecule real-time (SMRT) sequencing, nanopore sequencing, or the like, e.g. U.S. Pat. Nos. 7,313,308; 8,153,375; 7,907,800; 7,960,116; 8,137, 569; Manrao et al. Nature Biotechnology, 4(8): 2685-2693 (2012); and the like.

In another aspect, the invention includes a method for determining the number of lymphocytes in a sample by counting unique sequence tags. Even without sequence tags, clonotypes of TCRβ or IgH genes, particularly those including the V(D)J regions, provide for a lymphocyte and its clones a unique marker. Whenever recombined nucleic acids are obtained from genomic DNA, then a count of lymphocytes in a sample may be estimated by the number of unique clonotypes that are counted after sequencing. This approach breaks down whenever there are significant clonal populations of identical lymphocytes associated with the same clonotype. The use of sequence tags overcomes this short coming and is especially useful for providing counts of lymphocytes in patients suffering from many lymphoid disorders, such as lymphomas or leukemias. In accordance with one aspect of the invention, sequence tags may be used to obtain an absolute count of lymphocytes in a sample regardless of whether there is a large dominant clone present, such as with leukemia. Such a method may be implemented with the steps: (a) obtaining a sample from an individual comprising lymphocytes; (b) attaching sequence tags to molecules of recombined nucleic acids of T-cell receptor genes or of immunoglobulin genes of the lymphocytes to form tag-molecule conjugates, wherein substantially every molecule of the tag-molecule conjugates has a unique sequence tag; (c) amplifying the tag-molecule conjugates; (d) sequencing the tag-molecule conjugates; and (e) counting the number of distinct sequence tags to determine the number of lymphocytes in the sample.

In some embodiments, sequence tags are attached to recombined nucleic acid molecules of a sample by labeling by sampling, e.g. as disclosed by Brenner et al, U.S. Pat. No. 5,846,719; Brenner et al, U.S. Pat. No. 7,537,807; Macevicz, International patent publication WO 2005/111242; and the like, which are incorporated herein by reference. In labeling by sampling, polynucleotides of a population to be labeled (or uniquely tagged) are used to sample (by attachment, linking, or the like) sequence tags of a much larger population. That is, if the population of polynucleotides has K members (including replicates of the same polynucleotide) and the population of sequence tags has N members, then N>>K. In one embodiment, the size of a population of sequence tags used with the invention is at least 10 times the size of the population of clonotypes in a sample: in another embodiment, the size of a population of sequence tags used with the invention is at least 100 times the size of the population of clonotypes in a sample; and in another embodiment, the size of a population of sequence tags used with the invention is at least 1000 times the size of the population of clonotypes in a sample. In other embodiments, a size of sequence tag population is selected so that substantially every clonotype in a sample will have a unique sequence tag whenever such clonotypes are combined with such sequence tag population, e.g. in an attachment reaction, such as a ligation reaction, amplification reaction, or the like. In some embodiments, substantially every clonotype means at least 90 percent of such clonotypes will have a unique sequence tag; in other embodiments, substantially every clonotype means at least 99 percent of such clonotypes will have a unique sequence tag; in other embodiments, substantially every clonotype means at least 99.9 percent of such clonotypes will have a unique sequence tag. In many tissue samples or biopsies the number of T cells or B cells may be up to or about 1 million cells; thus, in some embodiments of the invention employing such samples, the number of unique sequence tags employed in labeling by sampling is at least $10^8$ or in other embodiments at least $10^9$.

In such embodiments, in which up to 1 million clonotypes are labeled by sampling, large sets of sequence tags may be efficiently produced by combinatorial synthesis by reacting a mixture of all four nucleotide precursors at each addition step of a synthesis reaction, e.g. as disclosed in Church, U.S. Pat. No. 5,149,625, which is incorporated by reference. The result is a set of sequence tags having a structure of "$N_1N_2 \ldots N_k$" where each $N_i$=A, C, G or T and k is the number of nucleotides in the tags. The number of sequence tags in a set of sequence tags made by such combinatorial synthesis is $4^k$. Thus, a set of such sequence tags with k at least 14, or k in the range of about 14 to 18, is appropriate for attaching sequence tags to a $10^6$-member population of molecules by labeling by sampling.

A variety of different attachment reactions may be used to attach unique tags to substantially every clonotype in a sample. In one embodiment, such attachment is accomplished by combining a sample containing recombined nucleic acid molecules (which, in turn, comprise clonotype sequences) with a population or library of sequence tags so that members of the two populations of molecules can randomly combine and become associated or linked, e.g. covalently. In such tag attachment reactions, clonotype sequences comprise linear single or double stranded polynucleotides and sequence tags are carried by reagents such as amplification primers, such as PCR primers, ligation adaptors, circularizable probes, plasmids, or the like. Several such reagents capable of carrying sequence tag populations are disclosed in Macevicz, U.S. Pat. No. 8,137,936; Faham et al, U.S. Pat. No. 7,862,999; Landegren et al, U.S. Pat. No. 8,053,188; Unrau and Deugau, Gene, 145: 163-169 (1994); Church, U.S. Pat. No. 5,149,625; and the like, which are incorporated herein by reference.

TCRβ Repertoire Analysis

In this example, TCRβ chains are analyzed. The analysis includes amplification, sequencing, and analyzing the TCRβ sequences. One primer is complementary to a common sequence in Cβ1 and Cβ2, and there are 34 V primers capable of amplifying all 48 V segments. Cβ1 or Cβ2 differ from each other at position 10 and 14 from the J/C junction. The primer for Cβ1 and Cβ2 ends at position 16 bp and has no preference for Cβ1 or Cβ2. The 34 V primers are modified from an original set of primers disclosed in Van Dongen et al, U.S. patent publication 2006/0234234, which is incorporated herein by reference. The modified primers are disclosed in Faham et al, U.S. patent publication 2010/0151471, which is also incorporated herein by reference.

Figure 2A:
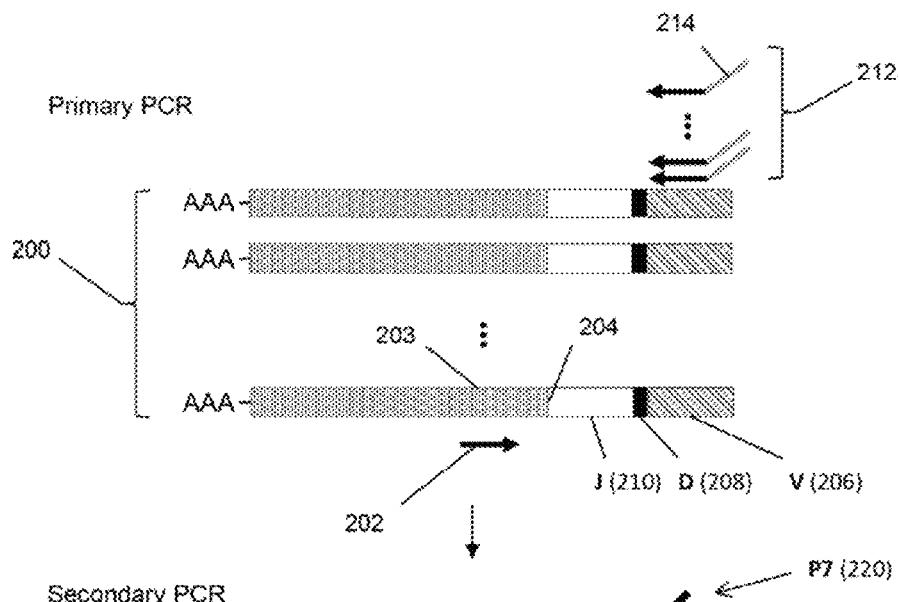
FIGS. 2A-2C show a two-staged PCR scheme for amplifying TCRβ genes.
Figure 2B:
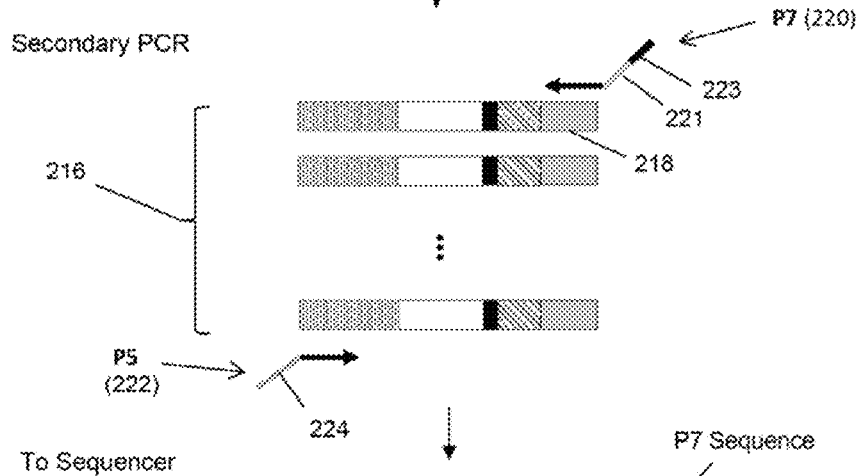

The Illumina Genome Analyzer is used to sequence the amplicon produced by the above primers. A two-stage amplification is performed on messenger RNA transcripts (200), as illustrated in FIGS. 2A-2B, the first stage employing the above primers and a second stage to add common primers for bridge amplification and sequencing. As shown in FIG. 2A, a primary PCR is performed using on one side a 20 bp printer (202) whose 3' end is 16 bases from the J/C junction (204) and which is perfectly complementary to Cβ1 (203) and the two alleles of Cβ2. In the V region (206) of RNA transcripts (200), primer set (212) is provided which contains primer sequences complementary to the different V region sequences (34 in one embodiment). Primers of set (212) also contain a non-complementary tail (214) that produces amplicon (216) having printer binding site (218) specific for P7 primers (220). After a conventional multiplex PCR, amplicon (216) is formed that contains the highly diverse portion of the J(D)V region (206, 208, and 210) of the mRNA transcripts and common printer binding sites (203 and 218) for a secondary amplification to add a sample tag (221) and primers (220 and 222) for cluster formation by bridge PCR. In the secondary PCR, on the same side of the template, a primer (222 in FIG. 2B and referred to herein as "C10-17-P5") is used that has at its 3' end the sequence of the 10 bases closest to the J/C junction, followed by 17 bp with the sequence of positions 15-31 from the J/C junction, followed by the P5 sequence (224), which plays a role in cluster formation by bridge PCR in Solexa sequencing. (When the C10-17-P5 primer (222) anneals to the template generated from the first PCR, a 4 bp loop (position 11-14) is created in the template, as the primer hybridizes to the sequence of the 10 bases closest to the J/C junction and bases at positions 15-31 from the J/C junction. The looping of positions 11-14 eliminates differential amplification of templates carrying Cβ1 or Cβ2. Sequencing is then done with a primer complementary to the sequence of the 10 bases closest to the J/C junction and bases at positions 15-31 from the J/C junction (this primer is called C"). C10-17-P5 primer can be HPLC purified in order to ensure that all the amplified material has intact ends that can be efficiently utilized in the cluster formation.)

In FIG. 2A, the length of the overhang on the V primers (212) is preferably 14 bp. The primary PCR is helped with a shorter overhang (214). Alternatively, for the sake of the secondary PCR, the overhang in the V primer is used in the primary PCR as long as possible because the secondary PCR is priming from this sequence. A minimum size of overhang (214) that supports an efficient secondary PCR was investigated. Two series of V primers (for two different V segments) with overhang sizes from 10 to 30 with 2 bp steps were made. Using the appropriate synthetic sequences, the first PCR was performed with each of the primers in the series and gel electrophoresis was performed to show that all amplified.

As illustrated in FIG. 2A, the primary PCR uses 34 different V primers (212) that anneal to V region (206) of RNA templates (200) and contain a common 14 bp overhang on the 5' tail. The 14 bp is the partial sequence of one of the Illumina sequencing primers (termed the Read 2 primer). The secondary amplification primer (220) on the same side includes P7 sequence, a tag (221), and Read 2 primer sequence (223) (this primer is called Read2_tagX_P7). The P7 sequence is used for cluster formation. Read 2 primer and its complement are used for sequencing the V segment and the tag respectively. A set of 96 of these primers with tags numbered 1 through 96 are created (see below). These primers are HPLC purified in order to ensure that all the amplified material has intact ends that can be efficiently utilized in the cluster formation.

As mentioned above, the second stage primer, C-10-17-P5 (222, FIG. 2B) has interrupted homology to the template generated in the first stage PCR. The efficiency of amplification using this primer has been validated. An alternative primer to C-10-17-P5, termed CsegP5, has perfect homology to the first stage C primer and a 5' tail carrying P5. The efficiency of using C-10-17-P5 and CsegP5 in amplifying first stage PCR templates was compared by performing real time PCR. In several replicates, it was found that PCR using the C-10-17-P5 primer had little or no difference in efficiency compared with PCR using the CsegP5 primer.

Figure 2C:
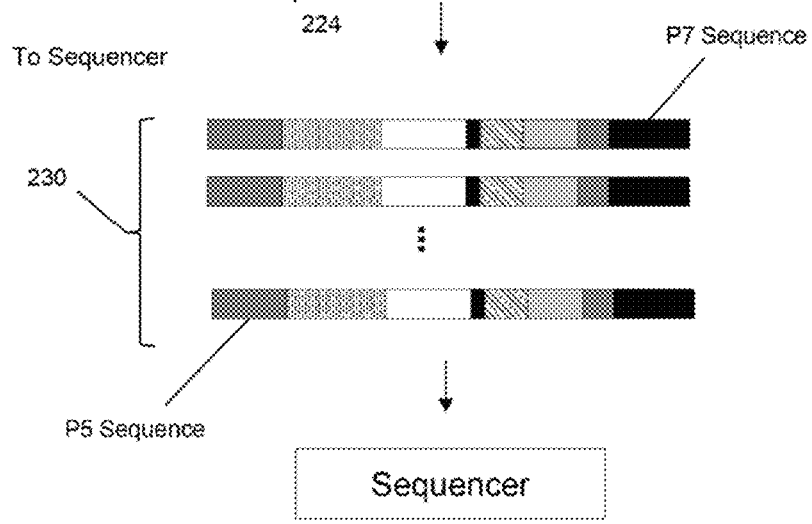

Amplicon (230) resulting from the 2-stage amplification illustrated in FIGS. 2A-2C has the structure typically used with the Illumina sequencer as shown in FIG. 2C. Two primers that anneal to the outmost part of the molecule, Illumina primers P5 and P7 are used for solid phase amplification of the molecule (cluster formation). Three sequence reads are done per molecule. The first read of 100 bp is done with the C' primer, which has a melting temperature that is appropriate for the Illumina sequencing process. The second read is 6 bp long only and is solely for the purpose of identifying the sample tag. It is generated using a tag primer provided by the manufacturer (Illumina). The final read is the Read 2 primer, also provided by the manufacturer (Illumina). Using this primer, a 100 bp read in the V segment is generated starting with the 1st PCR V primer sequence.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

DEFINITIONS

Unless otherwise specifically defined herein, terms and symbols of nucleic acid chemistry, biochemistry, genetics, and molecular biology used herein follow those of standard treatises and texts in the field, e.g. Komberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular immunology, 6$^{th}$ edition (Saunders, 2007).

"Aligning" means a method of comparing a test sequence, such as a sequence read, to one or more reference sequences to determine which reference sequence or which portion of a reference sequence is closest based on some sequence distance measure. An exemplary method of aligning nucleotide sequences is the Smith Waterman algorithm. Distance measures may include Hamming distance, Levenshtein distance, or the like. Distance measures may include a component related to the quality values of nucleotides of the sequences being compared.

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference; Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al. Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonotype" means a recombined nucleotide sequence of a T cell or B cell encoding a T cell receptor (TCR) or B cell receptor (BCR), or a portion thereof. In one aspect, a collection of all the distinct clonotypes of a population of lymphocytes of an individual is a repertoire of such population, e.g. Arstila et al. Science, 286: 958-961 (1999); Yassai et al, Immunogenetics, 61: 493-502 (2009); Kedzierska et al, Mol. Immunol., 45(3): 607-618 (2008); and the like. As used herein, "clonotype profile," or "repertoire profile," is a tabulation of clonotypes of a sample of T cells and/or B cells (such as a peripheral blood sample containing such cells) that includes substantially all of the repertoire's clonotypes and their relative abundances. "Clonotype profile," "repertoire profile," and "repertoire" are used herein interchangeably. (That is, the term "repertoire," as discussed more fully below, means a repertoire measured from a sample of lymphocytes). In one aspect of the invention, clonotypes comprise portions of an immunoglobulin heavy chain (IgH) or a TCRβ chain. In other aspects of the invention, clonotypes may be based on other recombined molecules, such as immunoglobulin light chains or TCRα chains, or portions thereof.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Pecent homologous," "percent identical," or like terms used in reference to the comparison of a reference sequence and another sequence ("comparison sequence") mean that in an optimal alignment between the two sequences, the comparison sequence is identical to the reference sequence in a number of submit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms, such as that described by Needleman and Wunsch, J. Mol. Biol., 48: 443-453 (1970)("GAP" program of Wisconsin Sequence Analysis Package, Genetics Computer Group, Madison, Wis.), or the like. Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package, Genetics Computer Group, Madison, Wis.). In other words, for example, to obtain a polynucleotide having a nucleotide sequence at least 95 percent identical to a reference nucleotide sequence, up to five percent of the nucleotides in the reference sequence may be deleted or substituted with another nucleotide, or a number of nucleotides up to five percent of the total number of nucleotides in the reference sequence may be inserted into the reference sequence.

"Flow system" means any instrument or device (i) that is capable of constraining particles or cells to move in a collinear path in a fluid stream by or through one or more detection stations which collect multiparameter data related to the particles or cells and (ii) that is capable of enumerating or sorting such particles based on the collected multiparameter data. Flow systems have a wide variety of forms and use a wide variety of techniques to achieve such functions, as exemplified by the following references that are incorporated by reference Shapiro, Practical Flow Cytometry, Fourth Edition (Wiley-Lisa, 2003), Bonner et al. Rev Sci Instruments, 43 404 (1972), Huh et al, Physiol Meas, 26 R73-98 (2005), Ateya et al, Anal Bioanal Chem, 391 1485-1498 (2008), Bohm et al, U.S. Pat. No. 7,157,274; Wang et al, U.S. Pat. No. 7,068,874, and the like. Flow systems may comprise fluidics systems having components wherein a sample fluid stream is inserted into a sheath fluid stream so that particles or cells in the sample fluid are constrained to move in a collinear path, which may take place is a cuvette, other chamber that serves as a detection station, or in a nozzle or other structure, for creating a stream-in-air jet, which may then be manipulated electrically, e.g. as with fluorescence-activated cell sorting (FACS) instruments. Flow systems, flow cytometers, and flow sorters and common applications thereof are disclosed in one or more of the following references, which are incorporated by reference; Robinson et al (Editors) Current Protocols in Cytometry (John Wiley & Sons, 2007); Shapiro, Practical Flow Cytometry, Fourth Edition (Wiley-Liss, 2003); Owens et al (Editors), Flow Cytometry Principles for Clinical Laboratory Practice: Quality Assurance for Quantitative Immunophenotyping (Wiley-Liss, 1994); Ormerod (Editor) Flow Cytometry: A Practical Approach (Oxford University Press, 2000); and the like.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al. Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: $\beta$-actin, GAPDH, $\beta_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al. Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Primer" means an oligonucleotide, either natural or synthetic that is capable, upon forming a duplex, with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Quality score" means a measure of the probability that a base assignment at a particular sequence location is correct. A variety methods are well known to those of ordinary skill for calculating quality scores for particular circumstances, such as, for bases called as a result of different sequencing chemistries, detection systems, base-calling algorithms, and so on. Generally, quality score values are monotonically related to probabilities of correct base calling. For example, a quality score, or Q, of 10 may mean that there is a 90 percent chance that a base is called correctly, a Q of 20 may mean that there is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Repertoire", or "immune repertoire", means a set of distinct recombined nucleotide sequences that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, a population of lymphocytes from which a repertoire is determined is taken from one or more tissue samples, such as one or more blood samples. A member nucleotide sequence of a repertoire is referred to herein as a "clonotype." In one aspect, clonotypes of a repertoire comprises any segment of nucleic acid common to a T cell or a B cell population which has undergone somatic recombination during the development of TCRs or BCRs, including normal or aberrant (e.g. associated with cancers) precursor molecules thereof, including, but not limited to, any of the following: an immunoglobulin heavy chain (IgH) or subsets thereof (e.g. an IgH variable region, CDR3 region, or the like), incomplete IgH molecules, an immunoglobulin light chain or subsets thereof (e.g. a variable region, CDR region, or the like), T cell receptor α chain or subsets thereof, T cell receptor β chain or subsets thereof (e.g. variable region, CDR3, V(D)J region, or the like), a CDR (including CDR1, CDR2 or CDR3, of either TCRs or BCRs, or combinations of such CDRs), V(D)J regions of either TCRs or BCRs, hypermutated regions of IgH variable regions, or the like. In one aspect, nucleic acid segments defining clonotypes of a repertoire are selected so that their diversity (i.e. the number of distinct nucleic acid sequences in the set) is large enough so that substantially every T cell or B cell or clone thereof in an individual carries a unique nucleic acid sequence of such repertoire. That is, in accordance with the invention, a practitioner may select for defining clonotypes a particular segment or region of recombined nucleic acids that encode TCRs or BCRs that do not reflect the full diversity of a population of T cells or B cells; however, preferably, clonotypes are defined so that they do reflect the diversity of the population of T cells and/or B cells from which they are derived. That is, preferably each different clone of a sample has different clonotype. (Of course, in some applications, there will be multiple copies of one or more particular clonotypes within a profile, such as in the case of samples from leukemia or lymphoma patients). In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected, tissue, or the like. In one embodiment, a repertoire comprising human TCRβ chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In another embodiment, a repertoire comprising human IgH chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In a particular embodiment, a repertoire of the invention comprises a set of nucleotide sequences encoding substantially all segments of the V(D)J region of an IgH chain. In one aspect, "substantially all" as used herein means every segment having a relative abundance of 0.001 percent or higher; or in another aspect, "substantially all" as used herein means every segment having a relative abundance of 0.0001 percent or higher. In another particular embodiment, a repertoire of the invention comprises a set of nucleotide sequences that encodes substantially all segments of the V(D)J region of a TCRβ chain. In another embodiment, a repertoire of the invention comprises a set of nucleotide sequences having lengths in the range of from 25-200 nucleotides and including segments of the V, D, and J regions of a TCRβ chain. In another embodiment, a repertoire of the invention comprises a set of nucleotide sequences having lengths in the range of from 25-200 nucleotides and including segments of the V, D, and J regions of an IgH chain. In another embodiment, a repertoire of the invention comprises a number of distinct nucleotide sequences that is substantially equivalent to the number of lymphocytes expressing a distinct IgH chain. In another embodiment, a repertoire of the invention comprises a number of distinct nucleotide sequences that is substantially equivalent to the number of lymphocytes expressing a distinct TCRβ chain. In still another embodiment, "substantially equivalent" means that with ninety-nine percent probability a repertoire of nucleotide sequences will include a nucleotide sequence encoding an IgH or TCRβ or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCRβ or portion thereof carried or expressed by every lymphocyte present at a frequency of 0.0001 percent or greater. The sets of clonotypes described in the foregoing two sentences are sometimes referred to herein as representing the "full repertoire" of IgH and/or TCRβ sequences. As mentioned above, when measuring or generating a clonotype profile (or repertoire profile), a sufficiently large sample of lymphocytes is obtained so that such profile provides a reasonably accurate representation of a repertoire for a particular application. In one aspect, samples comprising from $10^5$ to $10^7$ lymphocytes are employed, especially when obtained from peripheral blood samples of from 1-10 mL.

"Sequence read" means a sequence of nucleotides determined from a sequence or stream of data generated by a sequencing technique, which determination is made, for example, by means of base-calling software associated with the technique, e.g. base-calling software from a commercial provider of a DNA sequencing platform. A sequence read usually includes quality scores for each nucleotide in the sequence. Typically, sequence reads are made by extending a primer along a template nucleic acid, e.g. with a DNA polymerase or a DNA ligase. Data is generated by recording signals, such as optical, chemical (e.g. pH change), or electrical signals, associated with such extension. Such initial data is converted into a sequence read.

"Sequence tag" (or "tag") or "barcode" means an oligonucleotide that is attached to a polynucleotide or template molecule and is used to identify and/or track the polynucleotide or template in a reaction or a series of reactions. A sequence tag may be attached to the 3'- or 5'-end of a polynucleotide or template or it may be inserted into the interior of such polynucleotide or template to form a linear conjugate, sometimes referred to herein as a "tagged polynucleotide," or "tagged template," or "tag-polynucleotide conjugate," "tag-molecule conjugate," or the like. Sequence tags may vary widely in size and compositions; the following references, which are incorporated herein by reference, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g. via a hybridization reaction or via an enzymatic reaction, such as sequencing; whether they are labeled, e.g. with a fluorescent dye or the like; the number of distinguishable oligonucleotide tags required to unambiguously identify a set of polynucleotides, and the like, and how different must tags of a set be is order to ensure reliable identification, e.g. freedom from cross hybridisation or misidentification from sequencing errors. In one aspect, sequence tags can each have a length, within a range of from 2 to 36 nucleotides, or from 4 to 30 nucleotides, or from 8 to 20 nucleotides, or from 6 to 10 nucleotides, respectively. In one aspect, sets of sequence tags are used wherein, each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases.

"Sequence tree" means a tree data structure for representing nucleotide sequences. In one aspect, a tree data structure of the invention is a rooted directed tree comprising nodes and edges that do not include cycles, or cyclical pathways. Edges from nodes of tree data structures of the invention are usually ordered. Nodes and/or edges are structures that may contain, or be associated with, a value. Each node in a tree has zero or more child nodes, which by convention are shown below it in the tree. A node that has a child is called the child's parent node. A node has at most one parent. Nodes that do not have any children, are called leaf nodes. The topmost node in a tree is called the root node. Being the topmost node, the root node will not have parents. It is the node at which operations on the tree commonly begin (although some algorithms begin with the leaf nodes and work up ending at the root). All other nodes can be reached from it by following edges or links.

What is claimed is:

1. A method for identifying lymphocytes belonging to a functional subset that have infiltrated a solid tissue comprising:
    sorting a sample of lymphocytes from an accessible tissue of an individual into at least one functional subset;
    generating a clonotype profile for each functional subset of lymphocytes from the accessible tissue by amplifying recombined nucleic acid molecules obtained from said at least one subset to obtain a plurality of amplicons and performing high throughput sequencing of the resulting plurality of amplicons to provide a list of clonotype sequences that identify individual lymphocytes of each functional subset;
    generating at least one clonotype profile from at least one sample of the solid tissue by amplifying recombined nucleic acid molecules obtained from said at least one sample of solid tissue to obtain a plurality of amplicons and performing high throughput sequencing of the resulting plurality of amplicons to provide a list of clonotype sequences in each sample; and
    identifying lymphocytes belonging to a functional subset that have infiltrated from the accessible tissue into the solid tissue by identifying a clonotype sequence from the solid tissue that is present in the list of clonotype sequences of a functional subset from the accessible tissue, wherein said step of identifying lymphocytes further includes determining numbers of lymphocytes of each of said at least one functional subset,
    wherein one or more of the clonotype profiles for one or more of the functional subsets comprise at least 1000 clonotypes of at least 30 nucleotides.

2. The method of claim 1 wherein at least one of said at least one functional subsets of lymphocytes comprises cytotoxic T cells, helper T cells, regulatory T cells, Th1 T cells, Th2 T cells, Th9 T cells, Th17 T cells, and/or Tfh T cells.

3. The method of claim 2 wherein said step of identifying further includes determining levels and/or ratios of lymphocytes of each of said at least one functional subset.

4. The method of claim 3 wherein said solid tissue is a solid tumor.

5. The method of claim 4 wherein said at least one functional subset of lymphocytes comprise regulatory T cells and cytotoxic T cells.

6. The method of claim 5 wherein said step of identifying includes determining a ratio of levels of regulatory T cells to cytotoxic T cells in said solid tumor.

7. The method of claim 3 wherein said at least one functional subset of lymphocytes comprise at least one subset of antigen-specific T cells.

8. The method of claim 1 wherein said accessible tissue is peripheral blood, bone marrow, lymph fluid, synovial fluid, or spinal cord fluid of said individual.

9. The method of claim 8 wherein said accessible tissue is peripheral blood of said individual.

10. The method of claim 1 wherein said step of identifying further includes enumerating said lymphocytes in each of said functional subsets by counting their respective clonotypes.

11. The method of claim 1 wherein said sample of said solid tissue comprises multiple tissue samples taken from different locations in said solid tissue.

12. The method of claim 1 wherein said at least one functional subset of lymphocytes comprise helper T cells and cytotoxic T cells.

13. The method of claim 12 wherein said helper T cells are FoxP3+ regulatory T cells.

14. The method of claim 13 wherein said cytotoxic T cells are identified by a CD8$^+$ marker and wherein said regulatory T cells are identified by markers CD4$^+$, CD25$^{+(high)}$, and CD127$^{(low)}$.

15. The method of claim 14 wherein said solid tissue is a solid tumor.

16. The method of claim 1 wherein said at least one functional subset of lymphocytes are sorted into separate containers on the basis of at least one cell surface marker or intracellular marker.

17. The method of claim 16 wherein said step of sorting said at least one functional subset of lymphocytes is implemented with a fluorescence-activated cell sorter (FACS).

18. The method of claim 1 wherein each of said clonotypes of said clonotype profiles comprises a recombined portion of a T-cell receptor gene.

19. The method of claim 18 wherein each of said clonotypes of said clonotype profiles comprises at least a portion of a V(D)J region of a nucleic acid encoding a T-cell receptor β chain.

20. The method of claim 19 wherein all of said clonotype profiles comprises at least $10^6$ clonotypes.

21. The method of claim 1 wherein said solid tissue is a solid tissue affected by an autoimmune disease.

22. The method of claim 21 wherein at least one of said at least one or more functional subsets of lymphocytes is selected from cytotoxic T cells, helper T cells, regulatory T cells, Th1 T cells, Th2 T cells, Th9 T cells, Th17 T cells, and/or Tfh T cells, and wherein said step of detecting further includes determining numbers, levels, and/or ratios of lymphocytes of each of said one or more functional subsets.

23. The method of claim 22 wherein said one or more functional subsets of lymphocytes comprise regulatory T cells, Th1 T cells, Th2 T cells, Th9 T cells, Th17 T cells, Tfh T cells, and/or at least one functional subset of antigen-specific T cells.

24. The method of claim 22 wherein said solid tissue is selected from the group consisting of colon tissue, small intestine tissue, skin, connective tissue, subcutaneous tissue, lung tissue, or kidney tissue.

25. The method of claim 1 wherein said solid tissue is a normal tissue, and wherein at least one of said one or more functional subsets of lymphocytes is selected from B cells, T cells, cytotoxic T cells, helper T cells, regulatory T cells, Th1 T cells, Th2 T cells, Th9 T cells, Th17 T cells, Tfh T cells, antigen-specific B cells and antigen-specific T cells, and wherein said step of detecting further includes determining numbers, levels, and/or ratios of lymphocytes of each of said one or more functional subsets.

26. The method of claim 1 further comprising sorting a sample of lymphocytes from an accessible tissue of an individual into at least 2 functional subsets.

27. The method of claim 1 further comprising sorting a sample of lymphocytes from an accessible tissue of an individual into at least 3 functional subsets.

28. The method of claim 1 further comprising sorting a sample of lymphocytes from an accessible tissue of an individual into at least 4 functional subsets.

29. The method of claim 1 further comprising sorting a sample of lymphocytes from an accessible tissue of an individual into at least 5 functional subsets.

* * * * *